United States Patent [19]
Kaneko et al.

[11] Patent Number: 5,749,830
[45] Date of Patent: May 12, 1998

[54] FLUORESCENT ENDOSCOPE APPARATUS

[75] Inventors: Mamoru Kaneko, Hannou; Yasuhiro Ueda, Kokubunji; Sakae Takehana, Machida; Masaya Yoshihara, Hino; Masahiko Iida, Hachioji; Naruto Shinkai, Machida; Kazunari Nakamura, Hino; Nobuhiko Washizuka, Tama; Yoshinao Oaki, Hino; Katsuya Suzuki, Hachioji, all of Japan

[73] Assignee: Olympus Optical Co., Ltd., Tokyo, Japan

[21] Appl. No.: 329,909

[22] Filed: Oct. 27, 1994

[30] Foreign Application Priority Data

Dec. 3, 1993 [JP] Japan .................. 5-304428
Dec. 3, 1993 [JP] Japan .................. 5-304429
Dec. 3, 1993 [JP] Japan .................. 5-304432
Feb. 10, 1994 [JP] Japan .................. 6-016879

[51] Int. Cl.$^6$ ............................................. A61B 1/06
[52] U.S. Cl. ................ 600/160; 600/109; 600/178; 128/665
[58] Field of Search ...................... 600/109, 118, 600/160, 178, 180, 181, 182; 128/653.1, 664, 665, 659; 364/413.2

[56] References Cited

U.S. PATENT DOCUMENTS

| | | | |
|---|---|---|---|
| 4,556,057 | 12/1985 | Hiruma et al. | 128/665 |
| 4,664,520 | 5/1987 | Matsuo et al. | 356/237 |
| 4,768,513 | 9/1988 | Suzuki | 128/665 |
| 4,821,117 | 4/1989 | Sekiguchi et al. | 600/178 |
| 5,042,494 | 8/1991 | Alfano | 128/665 |
| 5,088,492 | 2/1992 | Takayama et al. | 128/659 |
| 5,092,331 | 3/1992 | Nakamura et al. | 128/665 |
| 5,143,435 | 9/1992 | Kikuchi | 600/178 |
| 5,187,572 | 2/1993 | Nakamura et al. | 600/109 |
| 5,318,024 | 6/1994 | Kittrell et al. | 128/665 |
| 5,413,108 | 5/1995 | Alfano | 128/665 |
| 5,438,989 | 8/1995 | Hochman et al. | 128/664 |
| 5,441,043 | 8/1995 | Wood et al. | 600/109 |

Primary Examiner—Richard J. Apley
Assistant Examiner—John P. Leubecker
Attorney, Agent, or Firm—Armstrong, Westerman, Hattori, McLeland & Naughton

[57] ABSTRACT

A fluorescent endoscope apparatus having: an endoscope that irradiates a subject portion to be observed with light transmitted through a light transmission device to obtain an object image of the subject portion to be observed; a normal observation light generating device for emitting normal light for performing normal light endoscope observation; a fluorescent observation light generating device for emitting excitation light for performing fluorescent light observation; an introduced-light switching device for selectively introducing, to the light transmission device of the endoscope, normal light emitted by the normal observation light generating device or excitation light emitted by the fluorescent observation light generating device; and an image sensing device for capturing a normal light image of the subject portion to be observed that can be obtained by irradiating the subject portion to be observed with normal light or excitation light or a fluorescent image that can be obtained due to irradiation with excitation light, the image sensing device being included or connected to the endoscope.

6 Claims, 52 Drawing Sheets

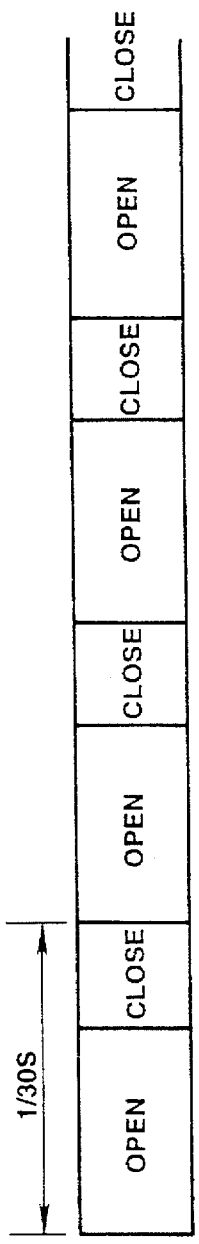
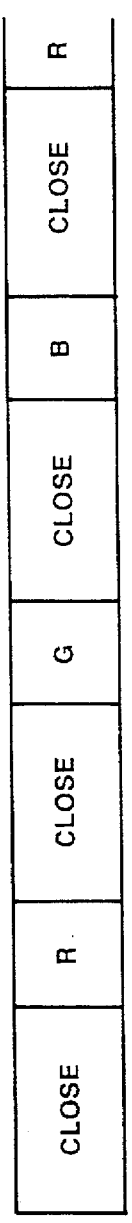
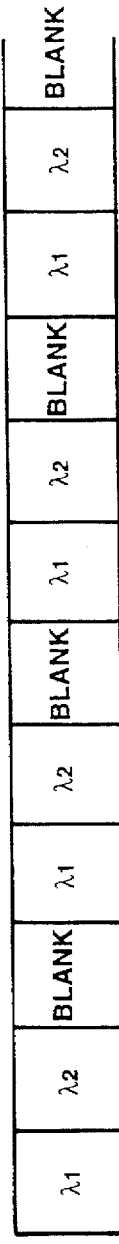
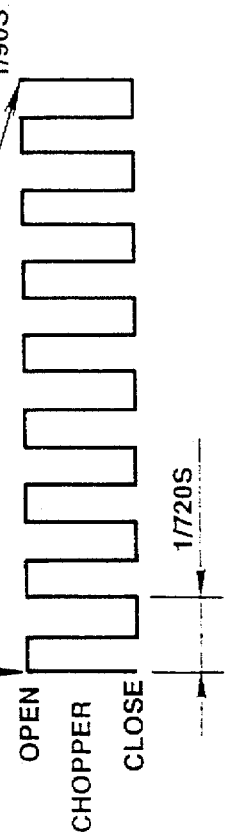
FIG.12(a) ROTATIVE SHUTTER
FIG.12(b) COLOR FILTER
FIG.12(c) ROTATIVE FILTER
FIG.12(d) CHOPPER

FIG.15
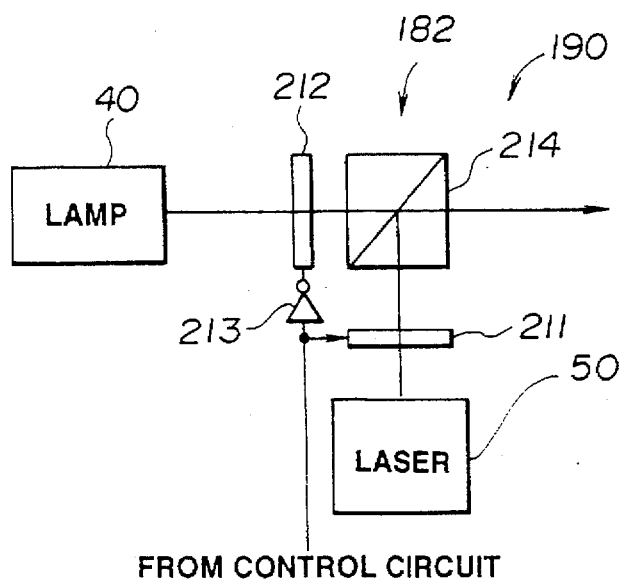
FROM CONTROL CIRCUIT
FIG.16(a)
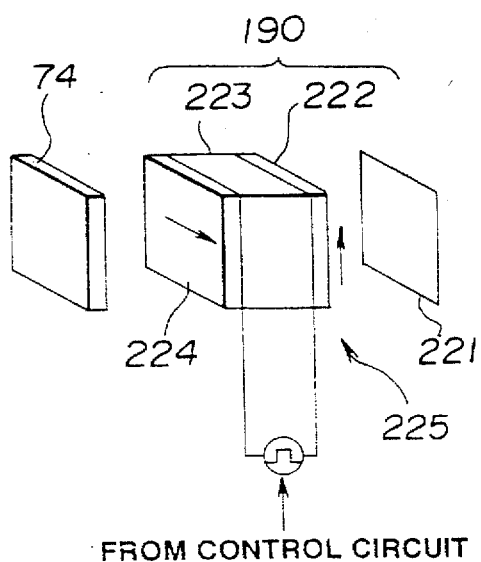
FROM CONTROL CIRCUIT
FIG.16(b)
| ON | FLUORESCENT IMAGE |
|---|---|
| OFF | NORMAL LIGHT IMAGE |

ORIGINAL IMAGE

IMAGE DIVIDED INTO
FIRST
SUB-BLOCK (2×2)

DIVIDE INTO FIRST SUB-BLOCK 2×2

UNIFY PIXELS

IMAGE PIXEL-UNIFIED
IN FIRST SUB-BLOCK

IMAGE DIVIDED INTO
SECOND
SUB-BLOCK (4×4)

DIVIDE INTO SECOND SUB-BLOCK 4×4

UNIFY PIXELS

UNIFY PIXELS IN SUB-BLOCKS 8×8, 16×16,···

IMAGE PIXEL-UNIFIED
IN SECOND SUB-BLOCK

FLUORESCENT ENDOSCOPE APPARATUS

BACKGROUND OF THE INVENTION

1. Field of the Invention

This invention relates to a fluorescent endoscope apparatus for obtaining both an observed image obtainable by irradiating an object with normal irradiating light and a fluorescent image obtainable by irradiating the object with excitation light.

2. Description of the Related Art

Recently, there has been a diagnosis technology that comprises the steps of: detecting fluorescent light spontaneously emitted by an organism or detecting fluorescent light emitted by a chemical injected into an organism as a two-dimensional image; and diagnosing degeneration of textures of the organism or a state of the disease (for example, the type of the disease or the infiltrated range), such as a cancer.

Fluorescent substances in an organism are exemplified by NADH (nicotinamide adenine nucleotide), FMN (flavin mono nucleotide) and pyridine nucleotide. The relationship between the intrinsic substances in an organism and the diseases has been clarified. If textures of an organism are irradiated with excitation light, fluorescent light having a wavelength longer than that of the excitation light is generated. Each of HpD (Hematoporphyrin), Photofrin and ALA (β-amino levulinic acid) has integrating characteristics into a cancer. By injecting any of the foregoing substances into an organism, irradiating the subject portion with excitation light and observing fluorescent light, a disease portion can be diagnosed.

Since fluorescent light generated in the organism is, however, very weak, high sensitivity photography must be performed to observe fluorescent light. As a high-sensitivity camera that is capable of performing the high-sensitivity photography, an image intensifier has been known.

Recently, a fluorescent observation apparatus for observing fluorescent light has been suggested which performs two-dimensional synchronizing detection so as to improve the sensitivity thereof.

The fluorescent observation apparatus for performing the two-dimensional synchronizing detection to improve the sensitivity has a structure that continuous laser beams are emitted by a laser beam apparatus 1, the laser beams are chopped at high speed by a chopper 2 with 1/600 sec clocks generated by a clock generator 20, the laser beams are enlarged by a concave lens 3 before a texture 4 is irradiated with the enlarged laser beams, fluorescent light emitted by the texture 4 is allowed to pass through a lens 5 and a filter 6 so that fluorescent light is captured by a CCD 7.

The filter 6 is a band-pass filter which cuts the laser beam and which permits only wavelengths greater than that of the laser beam, that is, which permits only fluorescent light to pass through. Fluorescent light is, at this time, generated in synchronization with turning on/off of excitation light so as to be detected by the CCD 7 while being chopped as described above, that is, being synchronized with the period of 1/600 sec. Detected fluorescent light is formed into an image signal by a video processor 8 and is converted into digital data by an A/D converter 9.

The multiplexor 10 is switched at the clock timing of 1/600 sec so that digital data is divided into ODD and EVEN frames, that is, digital data is divided into images formed when fluorescent light is being generated and images formed when fluorescent light is not being generated (the reverse permitted), and the divided images are stored in frame memories 11 and 12. Data items stored in the frame memories 11 and 12 are difference-calculated by a difference circuit 13 at a period of 1/300 sec (divided by clocks in a dividing circuit 14). Furthermore, the results of the difference-calculations are, about 10 times, integrated by an integrating circuit 15. Thus, noise can be canceled and a required signal can be amplified so that the S/N (the SN ratio) of the signal is improved. The signal is, then, formed into a video signal by a video processor 16 and is displayed on a monitor 17. Reference numeral 19 shown in FIG. 1 represents a two-dimensional lock-in amplifier portion for improving the S/N ratio.

U.S. Pat. No. 4,556,057 has disclosed a system comprising a diagnosing laser beam source, a curing laser beam source and a normal photographing light source, wherein the normal photographing light source is controlled in synchronization with the activation/deactivation of the diagnosing light source, fluorescent light generated due to irradiation with excitation light is captured by an image sensing apparatus having an image intensifier, returned light obtained by irradiation with irradiating light for normal observation (hereinafter abbreviated to "normal light") is captured by a normal image sensing apparatus, and an observed fluorescent image and an observed normal image are displayed on monitors which correspond to the image sensing apparatuses so that a cancer is diagnosed and cured.

As described above, it is important for the fluorescent observation to perform observation of a normal screen as well as a fluorescent image when an orientation is performed. In order to obtain both fluorescent-light image and a normal-light image, a plurality of cameras have been used or one camera has been used to perform the photography in a time-divided manner so as to obtain the two types of the images.

However, the foregoing case where the fluorescent-light image and the normal-light image are photographed by corresponding cameras involves a problem that the structure of the apparatus becomes too complicated and the size of the image sensing portion cannot be reduced.

When one camera is used to perform the photography in a time-divided manner as described above, any excessive differences between the intensity of received light from the fluorescent-light image and that from the normal-light image causes the fluorescent-light image to be darkened unsatisfactorily, halation to take place in the normal-light image which results in sticking.

Since the fluorescent light observation is performed in such a manner that excitation light in a predetermined quantity is always emitted from the light source for the fluorescent light observation to irradiate the subject portion to be observed, reflected light in an adequate quantity cannot always be obtained depending upon the state of the subject portion to be observed. In the foregoing case, a satisfactory image cannot always be obtained in the fluorescent light observation.

Since the optical system included in the endoscope comprises a plurality of optical members consisting of fibers for introducing light and a diffusion lens for irradiating the inside portion of an organism and image transmitting fibers, an objective lens and an ocular lens for transmitting an image obtained by the light irradiation to the outside of the organism, individual characteristics of the optical members, such as wavelength, dispersion and distortion cause the distribution of the fluorescent light to be irregular. In this case, there arises a problem in that whether or not the observed portion is a diseased portion cannot easily be determined.

What is worse, the conventional system has no means for simultaneously performing a diagnosis of the subject portion with fluorescent light and a laser curing treatment while observing the portion with fluorescent observation light. Therefore, it has been difficult to confirm the portion to be cured and perform the laser curing treatment while observing the portion with fluorescent light.

SUMMARY OF THE INVENTION

An object of the present invention is to provide a fluorescent endoscope apparatus which is capable of capturing both normal light image and a fluorescent light image and which has a simple structure.

Another object of the present invention is to provide a fluorescent endoscope apparatus which is capable of photographing a normal light image and a fluorescent light image by one camera thereof without a risk of generation of sticking and which has a simple structure.

Another object of the present invention is to provide a fluorescent endoscope apparatus which is capable of performing an errorless and accurate diagnosis by correcting the distribution of fluorescent light intensities.

Another object of the present invention is to provide a fluorescent endoscope apparatus capable of performing observation by integrating a normal-light camera and a fluorescent-light camera when a normal image and a fluorescent image are photographed by corresponding cameras.

Another object of the present invention is to provide a fluorescent endoscope apparatus having a function of a fluorescent observation apparatus for obtaining a fluorescent image to perform observation and diagnosis and a function of a laser curing apparatus for performing a curing laser beam treatment and capable of simultaneously performing fluorescent observation of a diseased portion or the like and laser cure.

The fluorescent endoscope apparatus according to the present invention comprises: an endoscope that irradiates a subject portion to be observed with light transmitted through light transmission means to obtain an object image of the subject portion to be observed; normal observation light generating means for emitting normal light for performing normal light endoscope observation; fluorescent observation light generating means for emitting excitation light for performing fluorescent light observation; introduced-light switching means for selectively introducing, to the light transmission means of the endoscope, normal light emitted by the normal observation light generating means or excitation light emitted by the fluorescent observation light generating means; and image sensing means for capturing a normal light image of the subject portion to be observed that can be obtained by irradiating the subject portion to be observed with normal light or excitation light or a fluorescent image that can be obtained due to irradiation with excitation light, the image sensing means being included in or connected to the endoscope.

Other and further objects, features and advantages of the invention will be appear more fully from the following description.

BRIEF DESCRIPTION OF THE DRAWINGS

FIGS. 2 to 5 illustrate a first embodiment of the present invention, where

FIG. 2 illustrates the structure of the fluorescent endoscope apparatus;

FIG. 3 is a characteristic graph which illustrates an example of the distribution of fluorescent light intensities in a subject portion to be observed in a texture of an organ;

FIG. 5 is a graph showing the relationship between red, green and blue wavelengths and wavelengths $\lambda1$ and $\lambda2$ of the filter;

FIG. 6 illustrates another structure of the rotative filter corresponding to the single-plate-type solid-state image sensing device;

FIG. 7 illustrates the structure of a fluorescent endoscope apparatus;

FIG. 12(a) illustrates timing of opening/closing of a rotative shutter;

FIG. 12(b) illustrates timing at which filters provided for a color filter are disposed on the optical path;

FIG. 12(c) illustrates timing at which filters provided for a rotative filter are disposed on the optical path;

FIG. 12(d) illustrates timing of opening/closing of a chopper;

FIG. 15 illustrates another example of the light source selection means of the introduced-light switching apparatus;

FIG. 16(a) illustrates the specific structure of a wavelength selection means;

FIG. 16(b) is a table for showing the types of images respectively allowed to pass through when a liquid crystal filter is turned on and the same is turned off;

FIG. 32 illustrates the operation to be performed when an image conversion table is made in the fluorescent endoscope apparatus, in which

DETAILED DESCRIPTION OF THE PREFERRED EMBODIMENTS

Referring to FIGS. 2 to 5, a first embodiment of the present invention will now be described.

Figure 1:
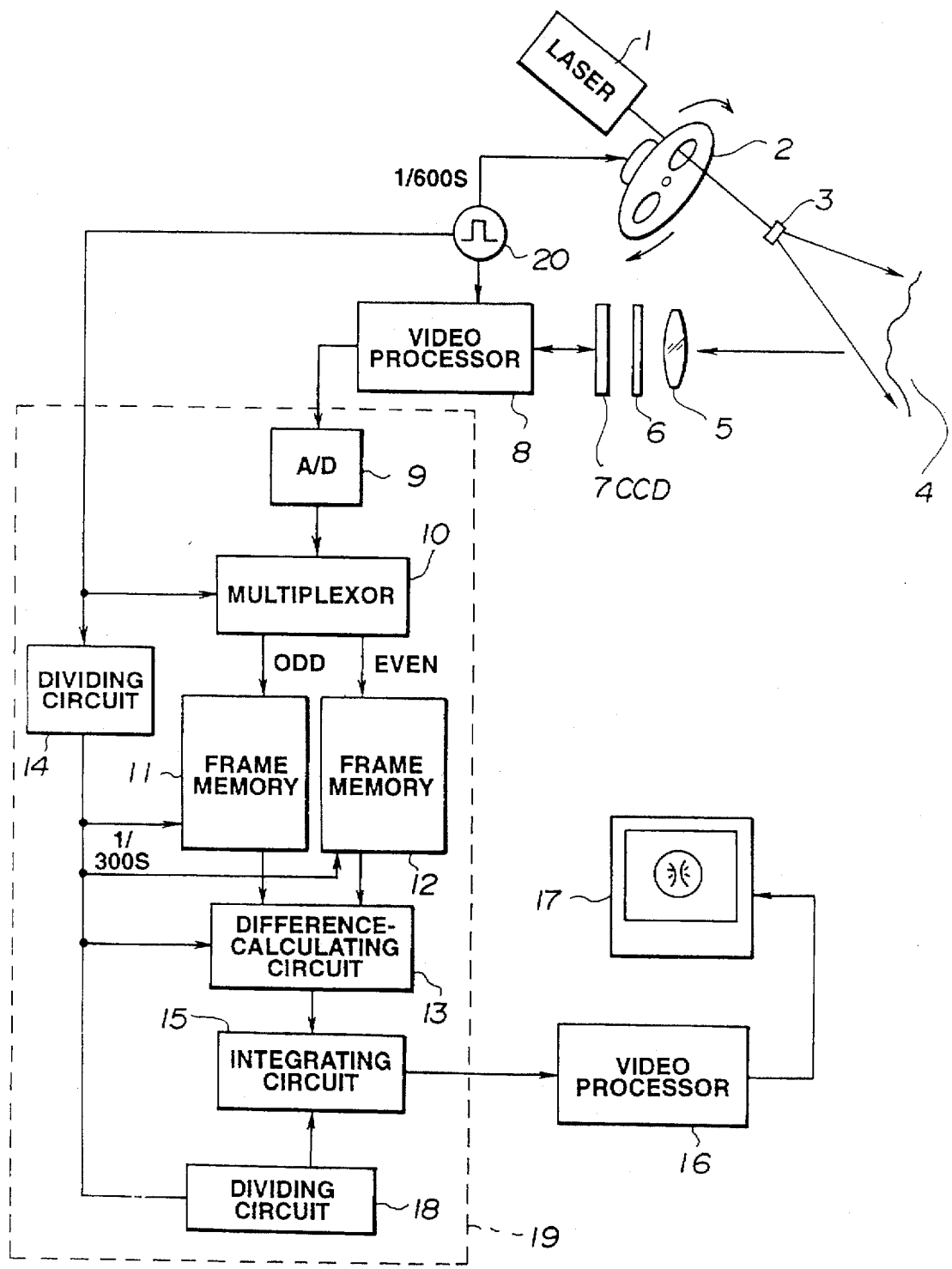
FIG. 1 is a schematic view which illustrates the overall structure of a conventional fluorescent endoscope apparatus.
Figure 2:
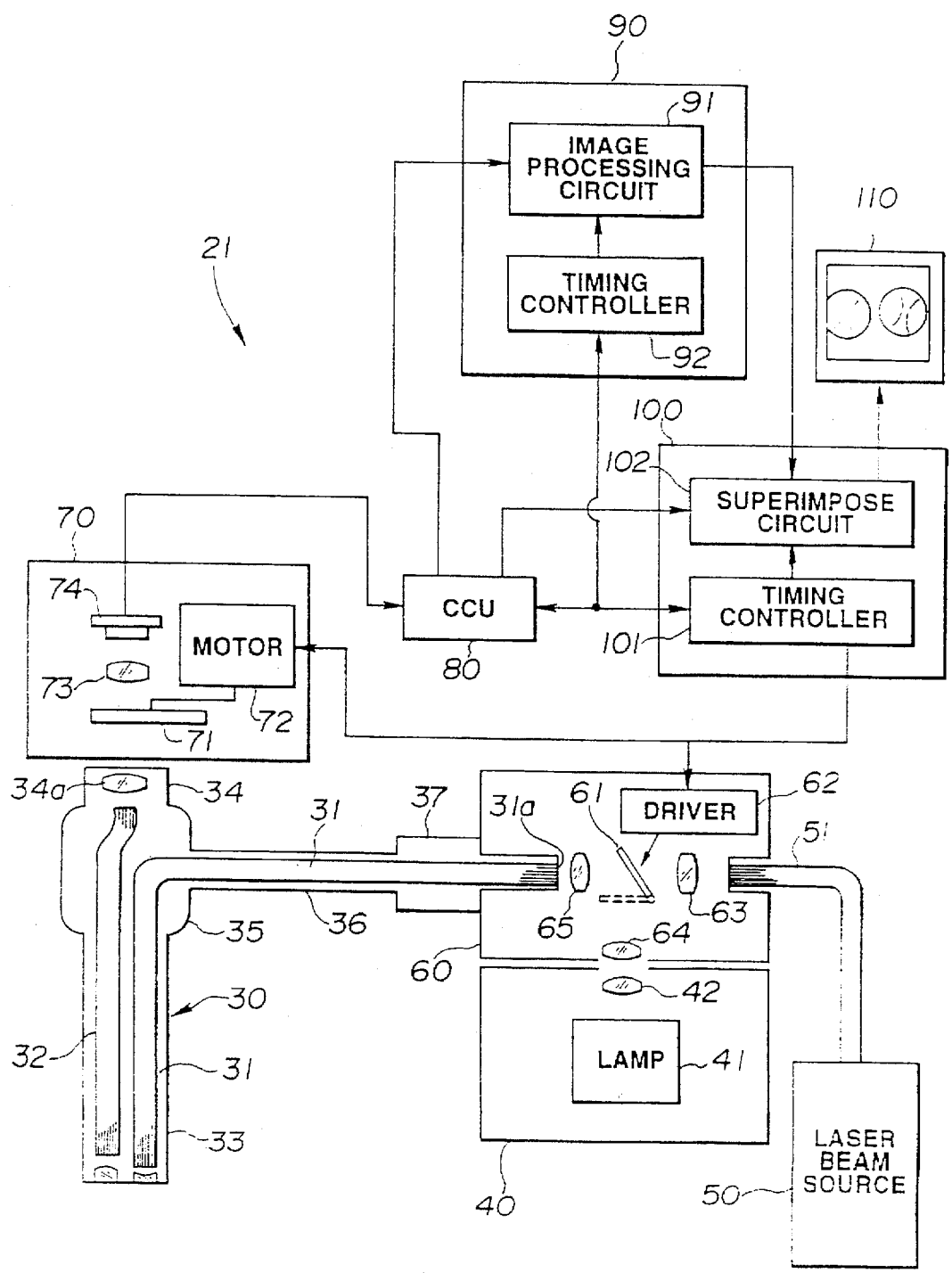

As shown in FIG. 2, a fluorescent endoscope apparatus 21 according to this embodiment comprises: an optical-type endoscope 30 having an insertion portion 33 which includes a light guide 31 serving as a light transmitting means for transmitting light emitted by a light source of an observing light generating means and an image guide 32 serving as an image transmitting means for transmitting an image obtained by irradiating a portion to be observed with light; a normal observation light source apparatus 40 serving as a normal observing light generating means having an irradiating lamp 41 such as a xenon lamp for generating normal light with which the endoscope 30 performs the normal endoscope observation; a fluorescent observing light source apparatus 50 serving as a fluorescent observing light generating means employing, for example, He—Cd laser for generating excitation light having wavelength λ0 (for example, λ0=350 nm to 500 nm) for the purpose of performing fluorescent light observation; an introduced-light switching apparatus 60 having a switching mirror 61 and a driver 62 for operating the switching mirror 61, the switching mirror 61 serving as an introduced-light switching means for selectively introducing, into the light guide 31 of the endoscope 30, normal observing light emitted by the normal observing light source apparatus 40 or excitation light λ0 emitted by the fluorescent observing light source apparatus 50; an external camera 70 detachably attached to an ocular portion 34 of the endoscope 30, the ocular portion 34 having an ocular lens 34a; a camera control unit (hereinafter abbreviated to a "CCU") 80 for obtaining an observed normal image signal of an image of the subject portion to be observed which has been formed with normal light by the external camera 70; a fluorescent image processing apparatus 90 that calculates a fluorescent image transmitted through the CCU 80, photographed by the external camera 70 and obtained due to irradiation of the subject portion to be observed with excitation light so as to obtain a fluorescent observation image signal; a control unit 100 for controlling the driver 62 for rotating the switching mirror 61 of the introduced-light switching apparatus 60 and a motor 72 for rotating a rotative filter 71, to be described later, of the external camera 70, the control unit 100 further controlling image signal outputs from the CCU 80 and the fluorescent image processing apparatus 90; and a monitor 110 serving as a display means for simultaneously or in a time-divided manner, switching and displaying the observed normal image signal and the observed fluorescent image signal.

The endoscope 30 has a structure that the image guide 32 included in the insertion portion 33 is extended to the ocular portion 34. On the other hand, the light guide 31 is extended to a control portion 35, the light guide 31 being allowed to pass through a universal cord 36 extending from the side portion of the control portion 35 so as to be connected to the introduced-light switching apparatus 60 through a light guide connector 37 disposed at an end of the universal cord 36, the end being an end adjacent to an operator.

The switching mirror 61 of the introduced-light switching apparatus 60 can be switched arbitrarily by the driver 62 disposed in an introduced-light switching adapter. The switching mirror 61 is disposed at a position at which normal observing light emitted by the normal observation light source apparatus 40 and excitation light λ0 emitted by the fluorescent observation light source apparatus 50 and transmitted through a transmitting light guide 51 perpendicularly intersect with each other, the switching mirror 61 being attached while being inclined by an angular degree of 45° from the optical path for normal observation light.

The driver 62 switches the switching mirror 61 to a position designated by a continuous line or a position designated by a dashed line in response to a switching signal supplied from the control unit 100. That is, when the switching mirror 61 is at the position designated by the dashed line, excitation light λ0 emitted by the fluorescent observation light source apparatus 50 is allowed to pass through an optical lens 63 so as to be converged to an end surface 31a of the light guide 31 of the endoscope 30. When the switching mirror 61 is at the position designated by the continuous line, normal observation light emitted by the normal observation light source apparatus 40 is allowed to pass through optical lenses 42 and 64 and is reflected by the switching mirror 61, the normal observation light then being allowed to pass through an optical lens 65 so as to be converted to the end surface 31a of the light guide 31 of the endoscope 30. Light thus-converged to the end surface 31a of the light guide 31 is allowed to pass through the light guide 31 so that the subject portion to be observed is irradiated with the normal observation light.

Figure 3:
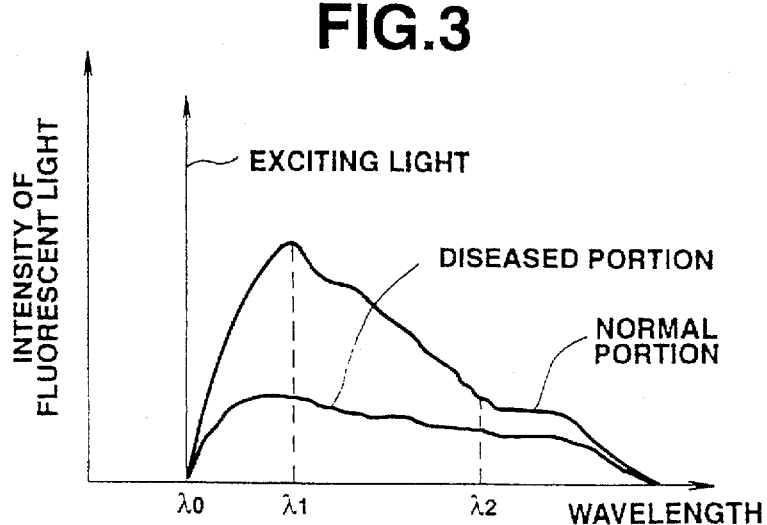

When the subject portion to be observed is irradiated with, for example, excitation light having a wavelength of λ0 (λ0=442 nm in this embodiment), the fluorescent characteristics are attained such that intensities of a wavelength band greater than the wavelength of excitation light are distributed as shown in FIG. 3. In particular, wavelength λ1 (λ1=480 nm to 520 nm in this embodiment) causes the intensity of fluorescent light from a normal portion to be intensified and causes the same from a diseased portion to be lowered. Furthermore, illustrated wavelengths λ1 and λ2 (λ2=630 nm or longer in this embodiment) cause the intensity of fluorescent light to be different between a normal portion and a diseased portion. Therefore, irradiation of the subject portion to be observed with excitation light λ0 and calculations of the ratio of or difference between the intensities of fluorescent light from image signals of fluorescent images with wavelengths λ1 and λ2 enable whether or not the subject portion to be observed is normal and video data, with which fluorescent diagnosis can be performed, to be generated in accordance with the result of the discrimination.

As shown in FIG. 2, the external camera 70 comprises a solid-state image sensing device 74 serving as an image sensing means for forming, through an optical system 73, an image transmitted through the image guide 32, a rotative filter 71 having a plurality of filters constituting an image selection means for selectively forming, on the solid-state image sensing device 74, the observed image obtained with normal observation light and the fluorescent image obtained with excitation light λ0 that have been transmitted through the image guide 32 of the endoscope 30, and a motor 72 for rotating the rotative filter 71.

Figure 4A:
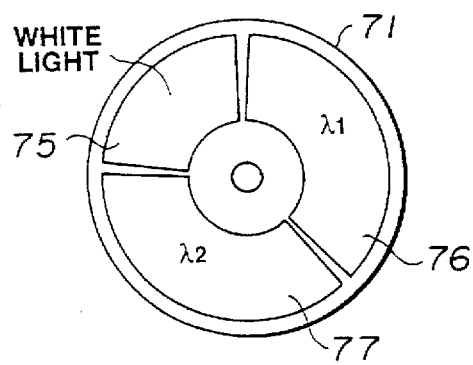
FIG. 4(a) illustrates the structure of a rotative filter corresponding to a single-plate-type solid-state image sensing device.

The rotative filter 71 is, as shown in FIG. 4(a), a rotative filter arranged to act in a case where the image sensing means is a solid-state image sensing device 74 adapted to a single-plate color method. In order to obtain a color endoscope image, the rotative filter 71 has a filter 75 disposed in about ¼ region of the overall filter region of the rotative filter 71, the filter 75 being arranged to permit white light to pass through. In the residual portion, that is, about ¾ filter region, a filter 76 for permitting fluorescent light having the wavelength λ1 and a filter 77 for permitting fluorescent light having the wavelength λ2 are disposed while respectively having ½ regions.

Figure 5:
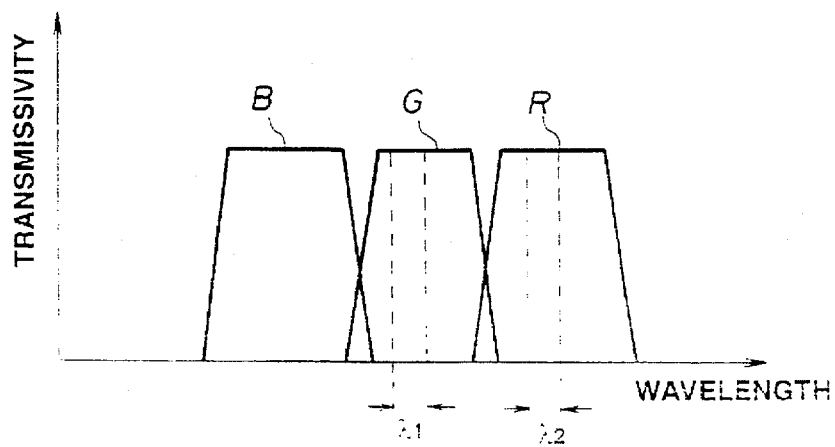

Since weak fluorescent light is detected to generate the image signal of the fluorescent image, the filters 76 and 77 have the largest possible aperture areas. The timing for reading the solid-state image sensing device 74 is controlled by the CCU 80. Note that the reading timing can be controlled by a timing controller 101 (to be described later) of the control unit 100. The rotative filter 71 is disposed on an optical path for the solid-state image sensing device 74 and the image guide 32. As the solid-state image sensing device 74, a high-sensitive image sensing device, such as a charge modulation device, charge-coupled device, static induced transistor or metal oxide semiconductor is employed. As shown in FIG. 5, the wavelength λ1 is set to a blue bandwidth among the red, green blue bandwidths and the wavelength λ2 is set to a red bandwidth.

As shown in FIG. 2, the control unit 100 comprises the timing controller 101 serving as a control means for controlling the driver 62 for switching the switching mirror 61 of the introduced-light switching apparatus 60 and the motor 72 for rotating the rotative filter 71 of the external camera 70. The timing controller 101 synchronizes, with each other, light for irradiating the subject portion to be observed through the introduced-light switching apparatus 60 and an observed image allowed to pass through the rotative filter 71 to be formed on the solid-state image sensing device 74. Moreover, the timing of the image processing operation performed by the CCU 80, the processing timing in a superimpose circuit 102 controlled by the timing controller 101 and the processing timing in the image processing circuit 91 controlled by a timing controller 92 of the fluorescent image processing apparatus 90 are synchronized with each other.

The operation of the fluorescent endoscope apparatus having the foregoing structure will now be described.

Initially, the endoscope 30 is inserted into the subject portion to be observed. Since no fluorescent image is required at this time, only the image formed with the normal light irradiation is required to be displayed on the monitor 110. Therefore, the timing controller 101 is controlled to fix the switching mirror 61 in the introduced-light switching apparatus 60 at the position designated by the continuous line so that only normal light emitted by the normal observation light source apparatus 40 is introduced into the light guide 31 of the endoscope 30. Furthermore, the filter 75 for white light for permitting normal light to pass through is disposed on the optical pass, the filter 75 being selected from the filters of the rotative filter 71 disposed between the image guide 32 and the solid-state image sensing device 74. Thus, an image obtained due to the normal light irradiation is formed on the solid-state image sensing device 74. While observing the normal image displayed on the monitor 110, the endoscope 30 is inserted into the subject portion to be observed.

When the endoscope 30 has reached the subject portion to be observed, the timing controller 101 is controlled to rotate the rotative filter 71 in the external camera 70 at, for example, 60 Hz. In synchronization with the revolutions of the rotative filter 71, the switching mirror 61 in the introduced-light switching apparatus 60 is operated.

Since the rotative filter 71 comprises the filter 75 for permitting normal light to pass through and the filters 76 and 77 for respectively permitting wavelengths λ1 and λ2 to pass through in such a manner that the ratio of the filter for white light and the filters for fluorescent light is 1:3, the commencement of the rotations of the rotative filter 71 at 60 Hz causes, during one rotation of the rotative filter 71, the filter 75 for normal light to be positioned for ¼×1/60 sec with respect to the image sensing surface of the solid-state image sensing device 74 and the filters 76 and 77 for fluorescent light to be positioned for ¾×1/60 sec with respect to the image sensing surface of the solid-state image sensing device 74. In synchronization with the rotation of the rotative filter 71, the switching mirror 61 in the introduced-light switching apparatus 60 is operated. That is, normal light emitted by the normal observation light source apparatus 40 is introduced into the light guide 31 of the endoscope 30 for ¼×1/60 sec. Excitation light emitted by the fluorescent observation light source apparatus 50 is introduced into the light guide 31 of the endoscope 30 for ¾×1/60 sec.

Normal light emitted by the normal observation light source apparatus 40 is allowed to pass through the light guide 31 of the endoscope 30 so that the subject portion to be observed is irradiated with normal light. As a result, light is reflected by the subject portion to be observed. Reflected light is transmitted through the image guide 32 of the endoscope 30 and allowed to pass through the filter 75 of the rotative filter 71 disposed in the external camera 70. Thus, a normal image is formed on the solid-state image sensing device 74 before it is converted into an electrical signal. Excitation light emitted by the fluorescent observation light source apparatus 50 is allowed to pass through the light guide 31 of the endoscope 30 so that the subject portion to be observed is irradiated with the excitation light. Thus, fluorescent light is generated by the subject portion to be observed. Thus-generated fluorescent light is transmitted through the image guide 32 of the endoscope 30 and is allowed to pass through the filters 76 and 77 for the wavelengths λ1 and λ2 of the rotative filter 71 disposed in the external camera 70. As a result, a fluorescent image is formed on the solid-state image sensing device 74, and the image is converted into an electrical signal.

The electrical signals of the normal image that has been photoelectrically converted by the solid-state image sensing device 74 and the fluorescent image obtained due to the irradiation with excitation light are transmitted to the CCU 80. The CCU 80 image-processes only the electrical signal of the normal image obtained due to the irradiation with normal light so that the electrical signal is formed into observed normal image data.

The electrical signal of the fluorescent image obtained due to the irradiation with excitation light λ0 is transmitted to an image processing circuit 91 in the fluorescent image processing apparatus 90 through the CCU 80. In the image processing circuit 91, electrical signals obtained by photoelectrically converting the fluorescent image having the wavelength λ1 and allowed to pass through the filter 76 and the fluorescent image having the wavelength λ2 and allowed to pass through the filter 77 are computed so that it is determined whether or not the subject portion is a diseased portion. If a determination has been made that the subject portion is a diseased portion due to the computation, an image process, for example, color change, is performed to identify the region having a possibility of the disease.

The normal observation image data processed by the CCU 80 and the fluorescent image data processed by the image processing circuit 91 are displayed on the monitor 110 through the superimpose circuit 102 of the control unit 100.

The fluorescent image processing apparatus 90 causes the timing controller 101 to control and synchronize, with each other, the timing for the CCU 80 to read the solid-state image sensing device 74 and the signal processing timing. Therefore, only the fluorescent images in the bands of the wavelengths λ1 and λ2 are received by the image processing circuit 91, the two images respectively stored in a frame memory that stores the image of the wavelength λ1 and in a frame memory that stores the image of the wavelength λ2 are subjected to a calculation in a calculating circuit for obtaining the difference. Then, a determination is made whether or not the value obtained due to the difference process is less than a predetermined value. If a region the value of which is smaller than the predetermined value is present, a color signal for coloring the region so as to easily be identified is transmitted through the superimpose circuit 102 so that the region having the possibility of disease is, by means of color, distinguished from the normal image.

Furthermore, the normal image processed by the CCU 80 and the fluorescent image subjected to the pseudo-coloring process are displayed on the monitor 110 while being overlapped.

Although the filter 75 for white light is provided for the rotative filter 71, the filter 75 may be omitted but a throughhole for allowing a normal image to pass through may be employed.

Since the wavelengths λ1 and λ2 are arbitrarily set in order to distinguish healthy portions and a diseased portion, it is preferable that the wavelength bands be selected with reference to the characteristic graph shown in FIG. 3 so that the diseased portion and the healthy portion can be distinguished sufficiently. The setting according to this embodiment is not limited to that shown in FIG. 5 in which the wavelength λ1 is included in the green bandwidth among red, green and blue bandwidths and the wavelength λ2 is included in the red bandwidth. The wavelengths may be set to other bandwidths. Accordingly, the sampling wavelengths are not limited to the two places, that is, the wavelengths λ1 and λ2. They may be set to three or more places, such as wavelengths λ1, λ2, λ3 and so forth.

As described above, this embodiment has an arrangement where the external camera having one image sensing device is attached to the ocular portion of the endoscope, and an endoscope image obtainable by the irradiation with light emitted by the normal observation light source apparatus or the fluorescent observation light source apparatus is captured. Thus, both the normal image and the fluorescent image can be displayed on a single monitor without changing the camera. As a result, two functions of excellent orientation and sensitive fluorescent observation can be provided. Thus, precise diagnosis and observation can be performed.

Since a usual fiber-type optical endoscope can be used as the foregoing endoscope, compatibility with the conventional endoscope system can be realized.

Only by interposing the introduced-light switching adapter, normal light emitted by the normal observation light source apparatus and excitation light emitted by the fluorescent observation light source apparatus can be switched. Furthermore, the image sensing portion of one external camera having the image selection means and the signal processing system can commonly be used as the ocular portion of the endoscope. Therefore, the apparatuses corresponding to the two images can be realized with low cost.

In order to obtain a fluorescent image that exhibits further excellent sensitivity with the foregoing structure, the mosaic filter disposed on the image sensing surface of the solid-state image sensing device 74 adapted to the single-plate color method may be disposed in the wavelength region in a manner such that a plurality of filters for different wavelength bands overlap with one another. In the foregoing case, signals can be obtained from pixels of the two filters having the overlapped wavelength bands. Therefore, the sensitivity of a weak fluorescent image can be improved.

Figure 4B:
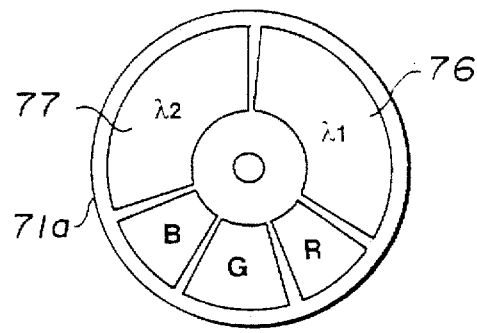
FIG. 4(b) illustrates the structure of a rotative filter that corresponds to a solid-state image sensing device for white and black image.

The rotative filter 71 is made to be a rotative filter 71a having an arrangement as shown in FIG. 4(b) in which the filters 76 and 77 for permitting fluorescent images having the wavelengths λ1 and λ2 to pass through are respectively disposed in ⅓ regions of the overall filter region. Furthermore, a filter for red light (designated by R in FIG. 4(b), a filter for green light (designated by G) and a filter for blue light (designated by B) are respectively disposed in ⅓ regions. Thus, a white and black solid-state image sensing device 74 corresponds to the rotative filter 71a so that the resolution can be improved as compared with the structure using the solid-plate color solid-state image sensing device. The foregoing red, green and blue filters are combined with each other so that a color image is captured.

Figure 6:
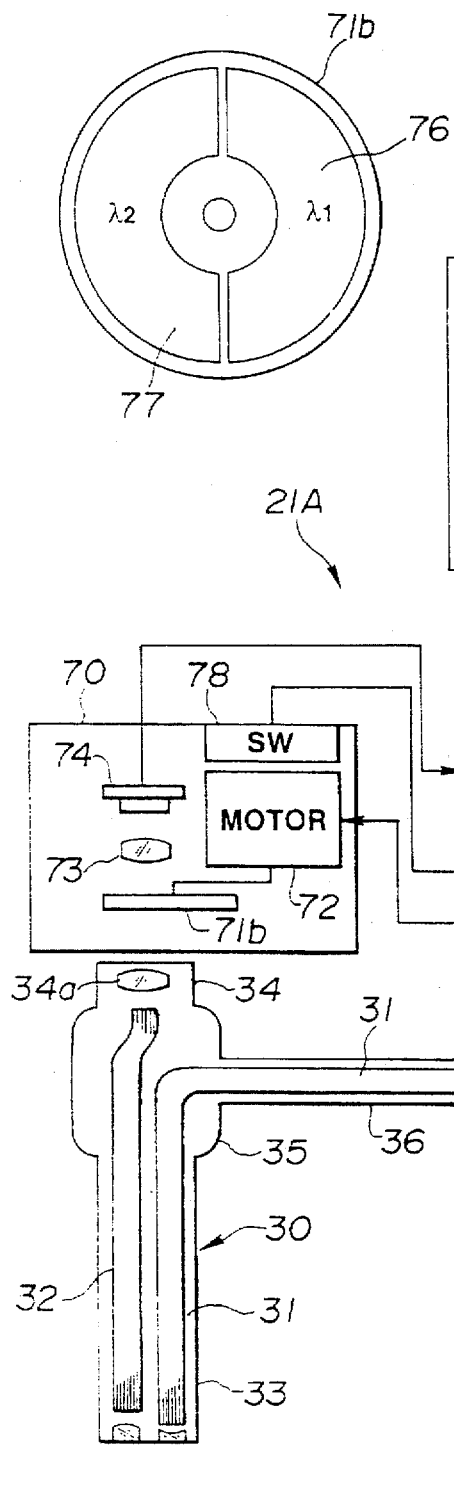
FIGS. 6 and 7 illustrate a modification of the first embodiment, where

A modification of the first embodiment will now be described with reference to FIGS. 6 and 7.

Figure 7:
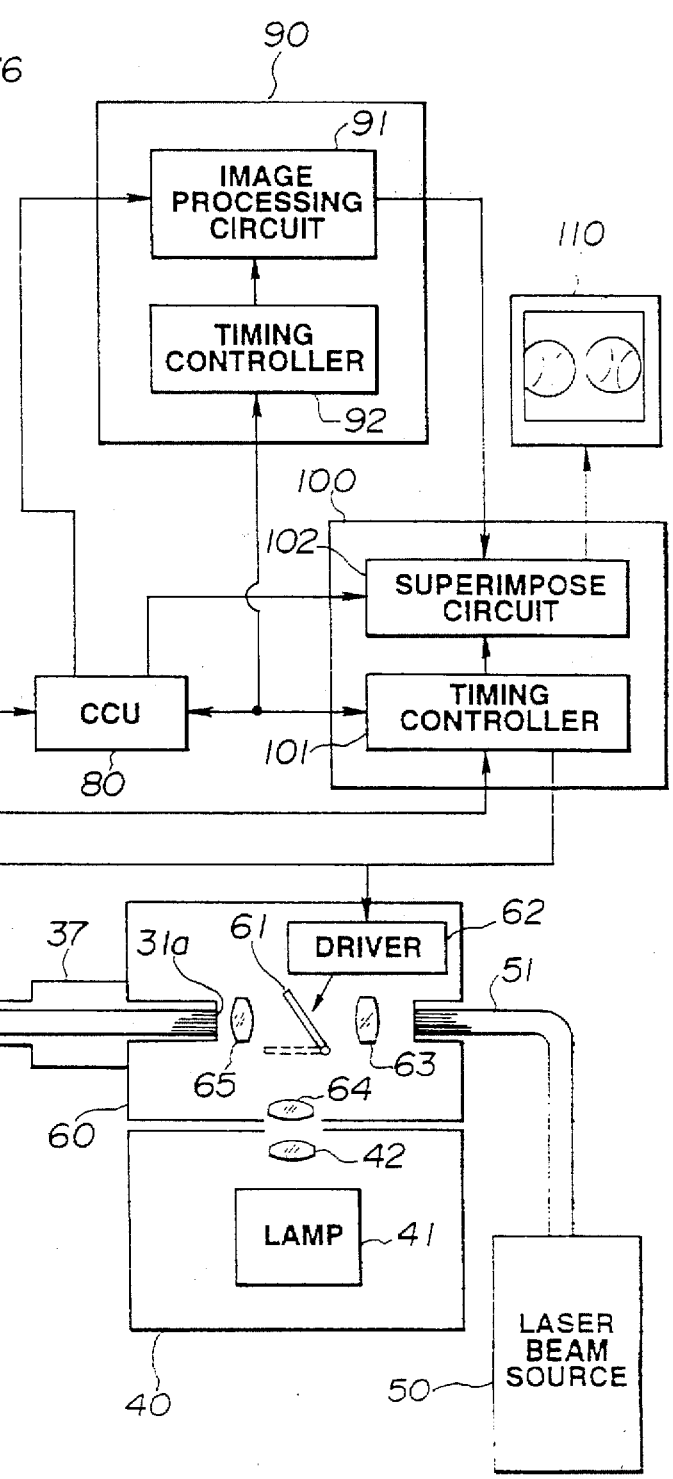

As shown in FIG. 7, a fluorescent endoscope apparatus 21A according to this modification comprises a rotative filter 71b in place of the rotative filter 71 according to the first embodiment. The rotative filter 71b is disposed on an optical path between the ocular portion 34 of the endoscope 30 and the solid-state image sensing device 74, the rotative filter 71b, as shown in FIG. 6, having the filters 76 and 77 for fluorescent light having wavelengths λ1 and λ2 that are disposed in ½ regions of the overall filter region. In addition to the structure according to the first embodiment, a fluorescent observing switch 78 is provided for the external camera 70. A attachable/detachable structure is constituted such that switching on/off of the fluorescent observing switch 78 moves the rotative filter 71b on the optical path between the ocular portion 34 of the endoscope 30 and the solid-state image sensing device 74 in directions designated by arrows. That is, the rotative filter 71b can be, by an attaching/detaching means (not shown), attached/detached to and from the optical path between the ocular portion 34 of the endoscope 30 and the solid-state image sensing device 74. The attaching/detaching means constitutes the image selection means and comprises, for example, a stage for supporting a motor 72 rotatively connected to the rotative filter 71b and a motor for moving the stage. The other structures and operations are similar to those of the first embodiment and common elements are given the same reference numerals and their descriptions are omitted.

The operation of the fluorescent endoscope apparatus 21A will now be described.

The fluorescent endoscope apparatus 21 A is in a normal light observation state when the fluorescent observing switch 78 is switched off. In this state the rotative filter 71b for fluorescent light is removed from the optical path that connects the solid-state image sensing device 74 and the ocular portion 34 to each other and therefore an image obtainable due to the normal light irradiation is formed on the solid-state image sensing device 74. When the fluorescent observing switch 78 provided for the external camera 70 is switched on, the rotative filter 71b for fluorescent light is inserted into the optical path that connects the solid-state image sensing device 74 and the ocular portion 34 to each other. The rotative filter 71b starts rotating so that the fluorescent observation state is realized in which an endoscope image formed with normal light in a state immediately before the fluorescent observing switch 78 is switched on is frozen and displayed on the monitor 110. Furthermore, the fluorescent image is superimposed on the frozen image to be displayed on the monitor 110.

Thus, the normal observation state or the fluorescent observation state of the external camera 70 can easily be selected by simply switching on/off the fluorescent observing switch 78.

The time required to read the image formed on the solid-state image sensing device can arbitrarily be controlled by the timing controller. Therefore, when an image formed due to the normal light irradiation and having excellent sensitivity is formed on the solid-state image sensing device 74, the signal of the solid-state image sensing device 74 is read, for example, every 1/60 second. If a fluorescent image having low sensitivity is formed on the solid-state image sensing device 74, the signal is read, for example, each second. Thus, a fluorescent image having excellent sensitivity can be obtained.

By combining the solid-state image sensing device having excellent sensitivity and the speeds of an electronic shutter, a fluorescent image can be captured with excellent sensitivity. The other effects are similar to those obtainable from the first embodiment.

A modification of the introduced-light switching apparatus will now be described.

As shown in FIGS. 2 and 7, the introduced-light switching apparatus 60 comprises the switching mirror 61 and the driver 62 for rotating the switching mirror 61 to switch light to be introduced into the light guide 31 of the endoscope 30. However, the structure of the introduced-light switching apparatus is not limited to the structure above. It may be constituted as follows.

Figure 8:
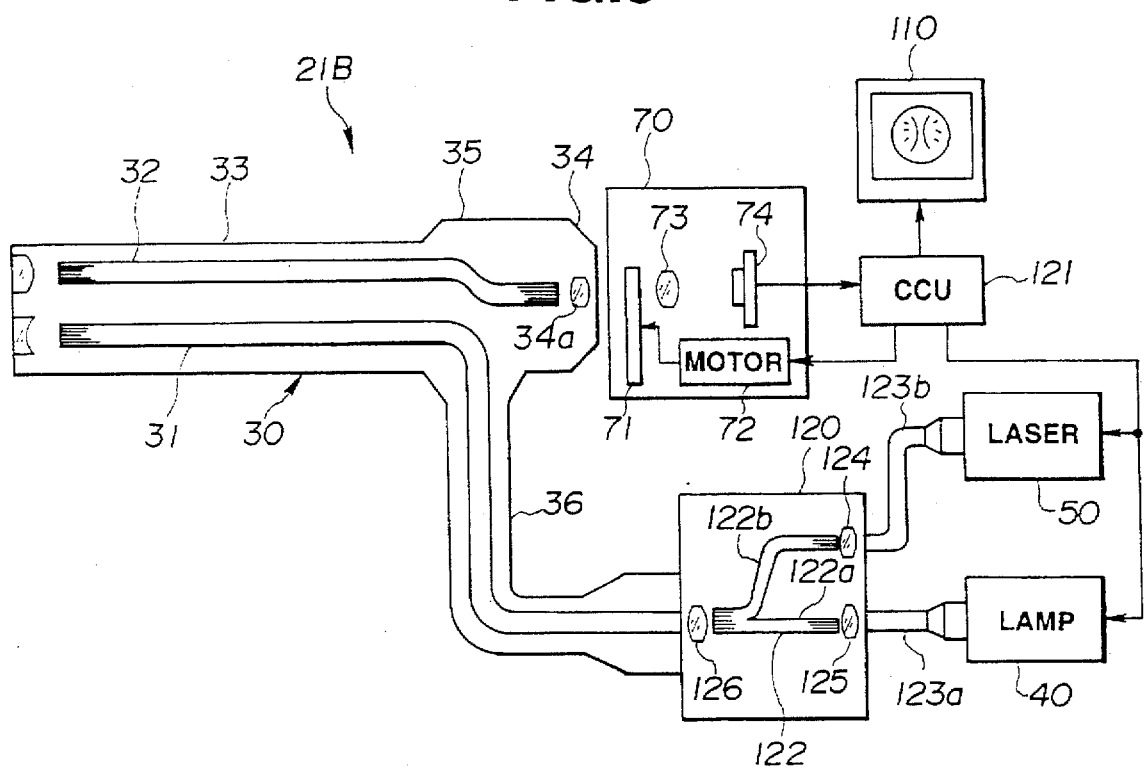
FIG. 8 is a schematic view which illustrates the structure of a fluorescent endoscope apparatus having an introduced-light switching apparatus having another structure.

As shown in FIG. 8, a fluorescent endoscope apparatus 21B according to this modification has another structure in place of the foregoing structure in which the introduced-light switching apparatus 60 that operates the switching mirror 61 so as to switch normal light emitted by the normal observation light source apparatus 40 and excitation light emitted by the fluorescent observation light source apparatus 50. The structure of this modification has an arrangement where the light source apparatuses for respectively emitting excitation light and normal light are activated/deactivated to introduce light from the respective light source apparatuses into either of branched light guides. Thus, light is supplied to the light guide 31 passing through the endoscope 30.

The introduced-light switching means of the fluorescent endoscope apparatus 21B comprises: a CCU 121; the normal observation light source apparatus 40 and the fluorescent observation light source apparatus 50 that are turned on/off by the CCU 121; and an introduced-light switching apparatus 120 including one light guide cable 122 which is, in the portion adjacent to the light source, branched into a normal light introducing light guide 122a and a fluorescent light introducing light guide 122b.

The introduced-light switching apparatus 120 has a light guide cord 123a extending from the introduced-light switching apparatus 120 so as to be connected to the normal observation light source apparatus 40 and a light guide cord 123b extending from the same so as to be connected to the fluorescent observation light source apparatus 50. Light transmitted through the light guide cords 123a and 123b is converged onto the end surfaces of the normal light introducing light guide 122a and the fluorescent light introducing light guide 122b by disposing optical lenses 124 and 125. An optical lens 126 for converging light onto the light guide 31 of the endoscope 30 is disposed.

The CCU 121 according to this modification has the functions of the CCU 80, the fluorescent image processing apparatus 90 and the control unit 100 so as to control the motor 72 and activation/deactivation of the normal observation light source apparatus 40 and the fluorescent observation light source apparatus 50 in synchronization with the motor 72. The structure of the connector attached to the light guide cord 123a adjacent to the operator has a similar structure to that of the connector of a light source apparatus for use in a usual endoscope apparatus. The other structures are the same as the foregoing embodiment. Therefore, the same elements are given the same reference numerals and their descriptions are omitted here.

The operation of the thus-constituted fluorescent endoscope apparatus 21B will now be described.

When observation with normal light is performed, only the normal observation light source apparatus 40 is required to be turned on. When the fluorescent observation with excitation light is performed, only the fluorescent observation light source apparatus 50 is required to be turned on. When the observation is performed with both normal light and excitation light, the CCU 121 is caused to control the respective light source apparatuses to introduce, in a time-divided manner, light into the light guide 31 in the endoscope 30 through the light guide 122 having the normal light introducing light guide 122a and the fluorescent light introducing light guide 122b. Then, signals of the images are processed by the CCU 121 so that the normal image or the fluorescent image is displayed on the monitor 110.

By electrically controlling switching of normal light and excitation light as described above, switching can be performed at high speed as compared with the structure in which mechanical control is performed. Furthermore, the size of the fluorescent endoscope apparatus can be reduced. Since known endoscopes and light source apparatuses can be used in this embodiment, the structure of the fluorescent endoscope apparatus can be constituted with low cost. The other operations and effects are similar to those obtainable from the foregoing embodiment.

Figure 9:
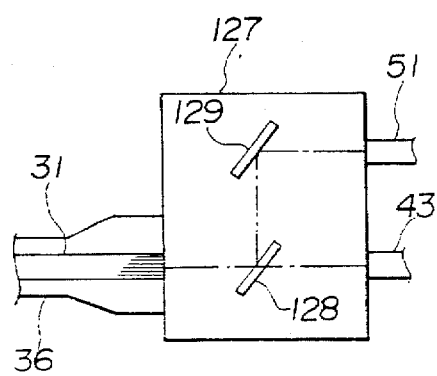
FIG. 9 is a schematic view which illustrates another structure of the introduced-light switching apparatus.

As an alternative to the light guide 122 having the branched portion adjacent to the light source and disposed in the introduced-light switching apparatus 120, an introduced-light switching apparatus 127 having a dichroic mirror 128 and a reflecting mirror 129 is constituted as shown in FIG. 9. The dichroic mirror 128 is disposed at an angle of 45 degrees made from an optical axis that connects the light guide 31 and the light guide cord 123a to each other. The reflecting mirror 129 is disposed to run parallel to the dichroic mirror 128. Therefore, normal light emitted through the light guide cord 123a is allowed to pass through the dichroic mirror 182 and is introduced into the light guide 31 in the endoscope. Excitation light emitted through the light guide cord 123b is reflected by the reflecting mirror 129 and is introduced into the dichroic mirror 128. Then, light is again reflected by the dichroic mirror 128 and is introduced into the light guide 31 in the endoscope. The other structures and effects are similar to those obtainable from the embodiment shown in FIG. 8 and therefore their descriptions are omitted here.

Figure 10:
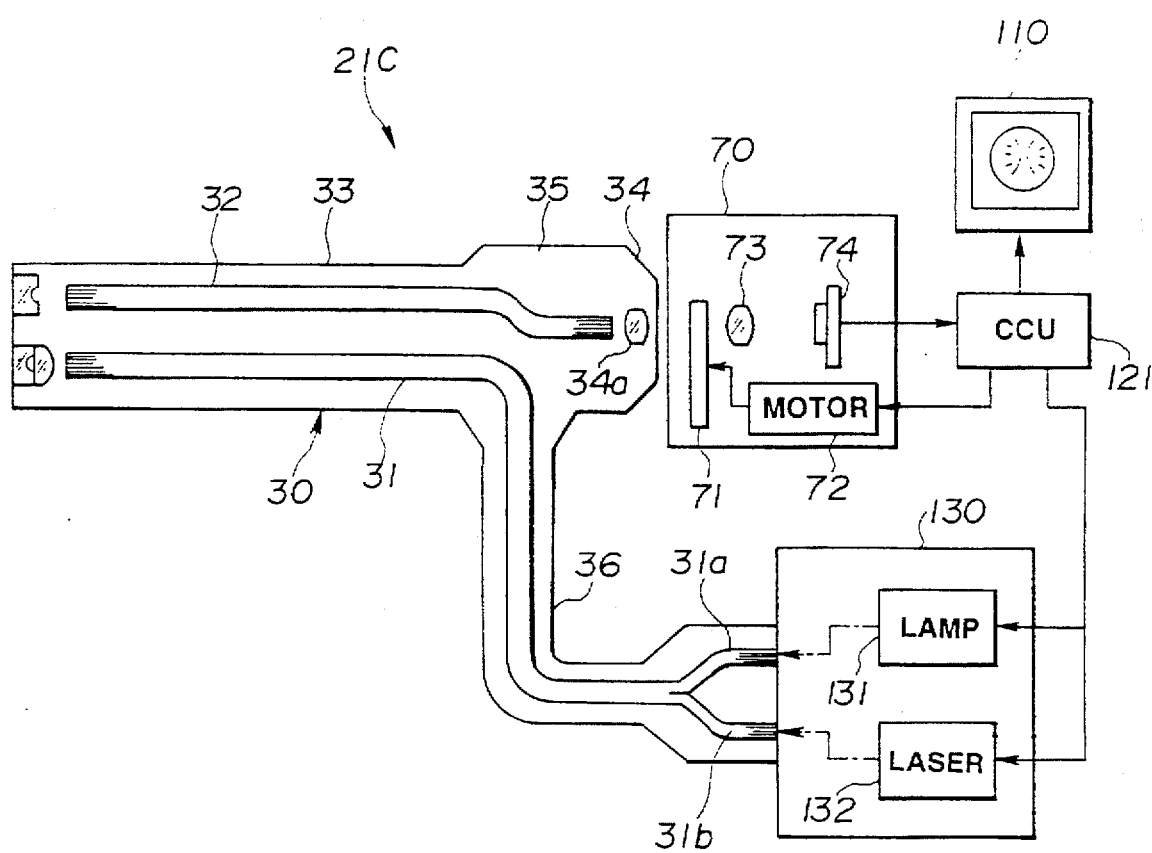
FIG. 10 is a schematic view which illustrates the structure of a fluorescent endoscope apparatus having no introduced-light switching apparatus.

A fluorescent endoscope apparatus 21C, as shown in FIG. 10, comprises a light source apparatus 130 including a normal observation lamp 131 and a fluorescent observation laser unit 132 that can be turned on and off by the CCU 121. The light guide 31 passing through the universal cord 36 extending from the side surface of the endoscope 30 is branched into two light guides 31a and 31b which are connected to face the normal observation lamp 131 and the fluorescent observation laser unit 132. Thus, no adapter is required to introduce normal light and excitation light into the light guide 31 of the endoscope 30. The other structures, operations and effects are similar to those obtainable from the embodiment shown in FIG. 8 and therefore their descriptions are omitted.

A fluorescent endoscope apparatus will now be described, with is capable of improving the sensitivity with respect to fluorescent light and photographing the fluorescent image and the normal image by one camera without a risk of sticking.

Figure 11:
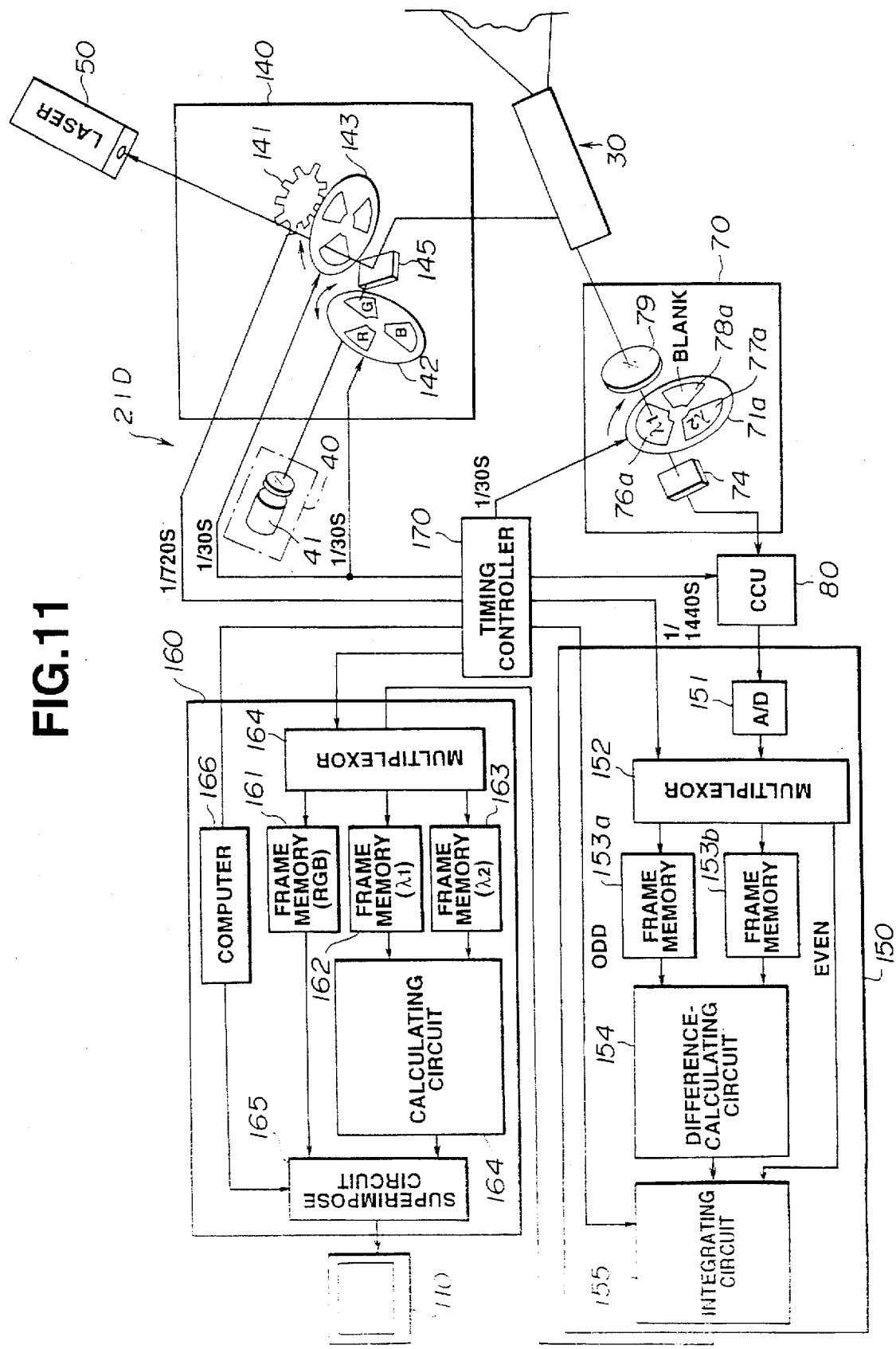
FIG. 11 illustrates a fluorescent endoscope apparatus having a two-dimensional lock-in amplifier.

This modification is an applicable example of the fluorescent endoscope apparatus according to the first embodiment and its modification. In order to improve the sensitivity of the fluorescent endoscope apparatus 21D with respect to the fluorescent image, the introduced-light switching apparatus has another structure as shown in FIG. 11. As a novel means for improving the sensitivity, a two-dimensional lock-in amplifier 150 is disposed which amplifies the image photographed by the external camera 70 so as to improve the S/N ratio. An image photographed by the external camera 70 is processed once by the two-dimensional lock-in amplifier 150 before it is transmitted to an image processing apparatus 160. Note that the introduced-light switching apparatus 140, the external camera 70, the two-dimensional lock-in amplifier 150 and the image processing apparatus 160 are synchronously controlled by a timing controller 170.

The structure of the fluorescent endoscope apparatus 21D will now be described.

The introduced-light switching apparatus 140 has a chopper 141 disposed on an optical path for excitation light emitted by the fluorescent observation light source apparatus 50. The chopper 141 is rotated in such a manner that tooth-like portions formed on the periphery of a light-shielding disc are so disposed as to cause excitation light to be turned on and off at a period of, for example, 1/720 sec. The introduced-light switching apparatus 140 comprising a color filter 142 having red, blue and green filter portions is disposed on the optical path for normal light emitted by the lamp 41 of the normal observation light source apparatus 40. The color filter 142 that is rotated at, for example 1/30 sec, a rotative shutter 143 which is disposed on the optical path for excitation light and which is rotated at 1/30 sec in synchronization with the color filter 142 to pass through or shield excitation light, and a dichroic mirror 145 disposed while being inclined by an angular degree of 45° from the optical path for normal light and positioned on the optical path for excitation light so as to reflect only excitation light. Thus, excitation light and normal light are supplied to a light guide (not shown) of the endoscope 30.

The timing of each of the chopper 141, the rotative shutter 143, the color filter 142 and the rotative filter 71a will now be described with reference to FIGS. 12(a) to 12(d).

As illustrated, the rotative shutter 143 and the color filter 142 are alternately opened. The rotative filter 71a is rotated in synchronization with the rotative shutter 143 and the color filter 142. That is, when the rotative shutter 143 is opened and therefore the subject portion to be observed is irradiated with excitation light, λ1 and λ2 filters 76a and 77a of the rotative filter 71a are sequentially disposed on the optical path which is observed by the external camera 70. When the subject portion to be observed is sequentially irradiated with normal light (red light, green light and blue light) transmitted through the color filter 142, a filter-less portion 78a of the rotative filter 71a is disposed on the observation optical path. Reference numeral 79 represents an objective lens for forming, on the solid-state image sensing device 74, an image of the subject portion to be observed.

More specifically, the rotative shutter 143 is opened for two thirds of the period of 1/30 sec so that excitation light is allowed to pass through the rotative shutter 143. Since the light shielding portion is disposed to face the color filter 142 in the foregoing open period, red light, green light and blue light are shielded. On the other hand, excitation light is turned on and off by the chopper 141 so as to be formed into pulses that pass through the rotative shutter 143. Excitation light allowed to pass through the rotative shutter 143 is reflected by the dichroic mirror 145 so as to be introduced to the subject portion to be observed.

The remaining third of the period of 1/30 sec for the rotative shutter 143 is a period in which excitation light is shielded. In the foregoing shielded period, the red, green and blue filters of the color filter 142 are sequentially disposed on the optical path. In this embodiment, for example, the red filter is disposed so that red light among red light, green light and blue light is supplied before it is allowed to pass through the dichroic mirror 145 so as to be introduced into the subject portion to be observed. Green light is then supplied at the next period, and then blue light is supplied at the next period.

That is, pulse-formed excitation light and any of red light, green light and blue light are, in a time-divided manner, introduced from the introduced-light switching apparatus 140 into the subject portion to be observed.

On the optical path for the external camera 70, the rotative filter 71a is disposed that is rotated at 1/30 sec in synchronization with the color filter 142 and the rotative shutter 143 to allow to pass through fluorescent images respectively having the two types of wavelengths λ1 and λ2 and a normal image.

Therefore, wavelength components of fluorescent light emitted by the subject portion to be observed, which are allowed to pass through the rotative filter 71a, reach the solid-state image sensing device 74 so that a fluorescent image is formed. That is, the rotative filter 71a causes the fluorescent images having the wavelengths λ1 and λ2 to be captured for each 1/90 sec because the λ1 and λ2 filters are sequentially disposed on the image capturing optical path as shown in FIG. 12(c). Light, for example, red light, reflected by the subject portion to be observed is allowed to pass through the rotative filter 71a for 1/90 sec so that a red image is formed on the solid-state image sensing device 74.

As shown in FIG. 12(c), the opened portion of the rotative filter 71a is disposed on the image capturing optical path in the period in which the red image is formed. At the same timing in the next period, irradiation and image sensing with green light are performed and then those with blue light are performed. That is, the photographing operation is performed by the external camera 70 in a time-division manner to correspond to excitation light and normal light in a time-division manner. The image formed on the imaging surface of the solid-state image sensing device 74 is photo-electrically converted and is transmitted to the CCU 80.

The CCU 80 and the rotative filter 71a are controlled by the timing controller 170 so that the CCU 80 generates image signals for a single frame at a period of 1/1440 sec, which is half of 1/720 sec.

The two-dimensional lock-in amplifier 150 comprises: an A/D converter 151 for converting the image signal into digital data; a multiplexor 152 for distributing image data to a frame memory (ODD) 153a and a frame memory (EVEN) 153b for each frame to correspond to turning on and off of excitation light that passes through the chopper 141 in synchronization with the timing controller 170; a difference-calculating circuit 154 for difference-calculating the frame memory (ODD) 153a and the frame memory (EVEN) 153b so as to cancel noise components for the purpose of improving the S/N ratio; and an integrating circuit 155 that integrates (in such a manner that the same image portions are respectively accumulated) images from which noise components have been canceled so as to improve the S/N ratio and amplify the image. The normal image is not allowed to pass through the frame memories 153a and 153b and the difference-calculating circuit 154 but it is directly received by the integrating circuit 155.

The image processing apparatus 160 comprises: a multiplexor 164 for distributing normal and fluorescent image data amplified by the two-dimensional lock-in amplifier 150 to a normal image storing frame memory (consisting of red, green and blue frame memories) 161, a λ1-image storing frame memory 162 and a λ2-image storing frame memory 163 in synchronization with the timing controller 170; a calculating circuit 164 that calculates the λ1-image storing frame memory 162 and the λ2-image storing frame memory 163 in order to clarify the characteristics of the texture in accordance with the fluorescent image; a superimpose circuit 165 for synthesizing the image in the normal image storing frame memory 161 and that in the calculating circuit 164; and a computer 166 for controlling the superimpose circuit 165 and the timing controller 170.

The other structures are the same as those of the first embodiment and the modification. The same elements are given the same reference numerals and their descriptions are omitted here.

The operation of the fluorescent endoscope apparatus 21D will now be described.

Excitation light emitted by the fluorescent observation light source apparatus 50 and normal light emitted by the normal observation light source apparatus 40 are respectively supplied to the introduced-light switching apparatus 140. Thus, excitation light formed into pulses at a period of, for example, 1/720 sec, and observing light (red, green and blue light) at a period of, for example, 1/30 sec are, in a time-division manner, alternately introduced into the light guide 31 of the endoscope 30 so that the subject portion to be observed is irradiated with light.

The wavelength components of fluorescent light obtained from excitation light used to irradiate the subject portion to be observed that have passed through the λ1 and λ2 filters of the rotative filter 71a reach the solid-state image sensing device 74 because the foregoing filters are sequentially disposed on the optical path as shown in FIG. 12(c). Thus, fluorescent images having the wavelengths λ1 and λ2 are captured. On the other hand, red, green and blue irradiation light beams reflected by the subject portion to be observed are allowed to pass through the rotative filter 71a and are imaged on the solid-state image sensing device 74. In the foregoing period, the opened portion of the rotative filter 71a is disposed in the image capturing optical path as shown in FIG. 12(c). That is, the solid-state image sensing device 74 captures the fluorescent image and the normal image in a time-division manner to correspond to excitation light and normal light applied in the time-division manner.

As described above, the portions of the fluorescent images that have the wavelengths λ1 and λ2 and the normal image are, by the common solid-state image sensing device 74, converted into image signals at the period of 1/1440 sec, which is the half of the foregoing period of 1/720 sec, that is, in synchronization with turning on and off of excitation light. Each of red, green and blue irradiation light beams is continuously applied for each 1/90 sec in such a manner that the corresponding images are repeatedly read at the period of 1/90 sec to 1/1440 sec.

The image signal that has been photoelectrically converted by the solid-state image sensing device 74 is supplied to the two-dimensional lock-in amplifier 150 so that its S/N ratio is improved and the signal level is amplified. In particular, the fluorescent image is subjected to a difference-calculating process in the difference circuit 154 in a manner such that the differences between light images and dark images formed due to turning on and off are processed. Thus, the influence of noise that is not related to turning on and off and that of 1/f noise which becomes critical by low frequency waves can significantly be eliminated. Therefore, weak image signals of a fluorescent image can be formed into fluorescent image signals exhibiting excellent S/N ratio.

Therefore, the fluorescent image signal transmitted by the difference circuit 154 can be set to a level free from excessive imbalance as compared with the level of an image signal obtained in a normal observation.

The thus-amplified image signals are divided into the fluorescent image and the normal image by the image processing apparatus 160 so that the respective images are converted into image data suitable to be displayed. Then, the images are synthesized by the superimpose circuit 165 so as to be displayed on the monitor 110.

The ratio of the fluorescent intensity of the wavelengths λ1 and λ2 is obtained at this time to discriminate whether or not the ratio is greater than a predetermined value. If the ratio of the fluorescent intensities is greater than the predetermined value, two images captured with the wavelengths λ1 and λ2 are added. The result of the addition is transmitted to the superimpose circuit 165 so that the fluorescent image is superimposed so as to be positioned together with the normal image. Thus, the two images are displayed on the monitor 110. If the ratio is smaller than the predetermined value, a similar display may, of course, be performed while displaying the region smaller than the predetermined value in a color that can easily be identified. Furthermore, a function may be provided which selectively displays the normal image and an image of either of the wavelengths or another function may be provided with which the fluorescent images of the two types of the wavelengths are displayed side by side or two types of fluorescent images are displayed as an image of a mixture of red and green.

By capturing the fluorescent image obtained by irradiating a subject portion to be observed with light and the normal image by using the common solid-state image sensing device 74 and by supplying the result of the image capturing operation to the two-dimensional lock-in amplifier 150, level imbalance between the fluorescent image signal and the normal image signal can be eliminated satisfactorily. Therefore, a necessity of providing a circuit for considerably increasing the gain in order to raise the level of the fluorescent image for a position in the signal processing system can be eliminated. Furthermore, problems of halation and sticking that takes place frequently in the normal image portion can be overcome and the two types of images can be displayed. The other operations and effects are similar to those obtainable from the first embodiment.

Since the brightness (the intensity) of fluorescence is changed due to the intensity of excitation light, the type of a fluorescent material and the efficiency of fluorescence generation, it is more effective to change the amplifying ratio by changing the number of the integrating operations performed by the integrating circuit 155 or by performing a process using a digital window (the number of bits increases due to the number of the integrating operations and the gain is changed by the portion of the bit from which the data is taken by cutting).

Since the fluorescent image is very dark as compared with the normal image, the quantity of fluorescence is changed due to the difference in the excitation wavelength, that in the intensity of fluorescence, that between spontaneous fluorescence and fluorescence realized by a chemical and the type of the chemical. Accordingly, there is a desire for a structure which is capable of satisfactorily displaying the two types of images even if the brightness of the fluorescent image is changed and thus the ratio of the brightness is changed with respect to that of the normal image.

Referring to FIGS. 13 to 17, an example which is capable of improving the S/N ratio and the sensitivity will now be described.

Figure 13:
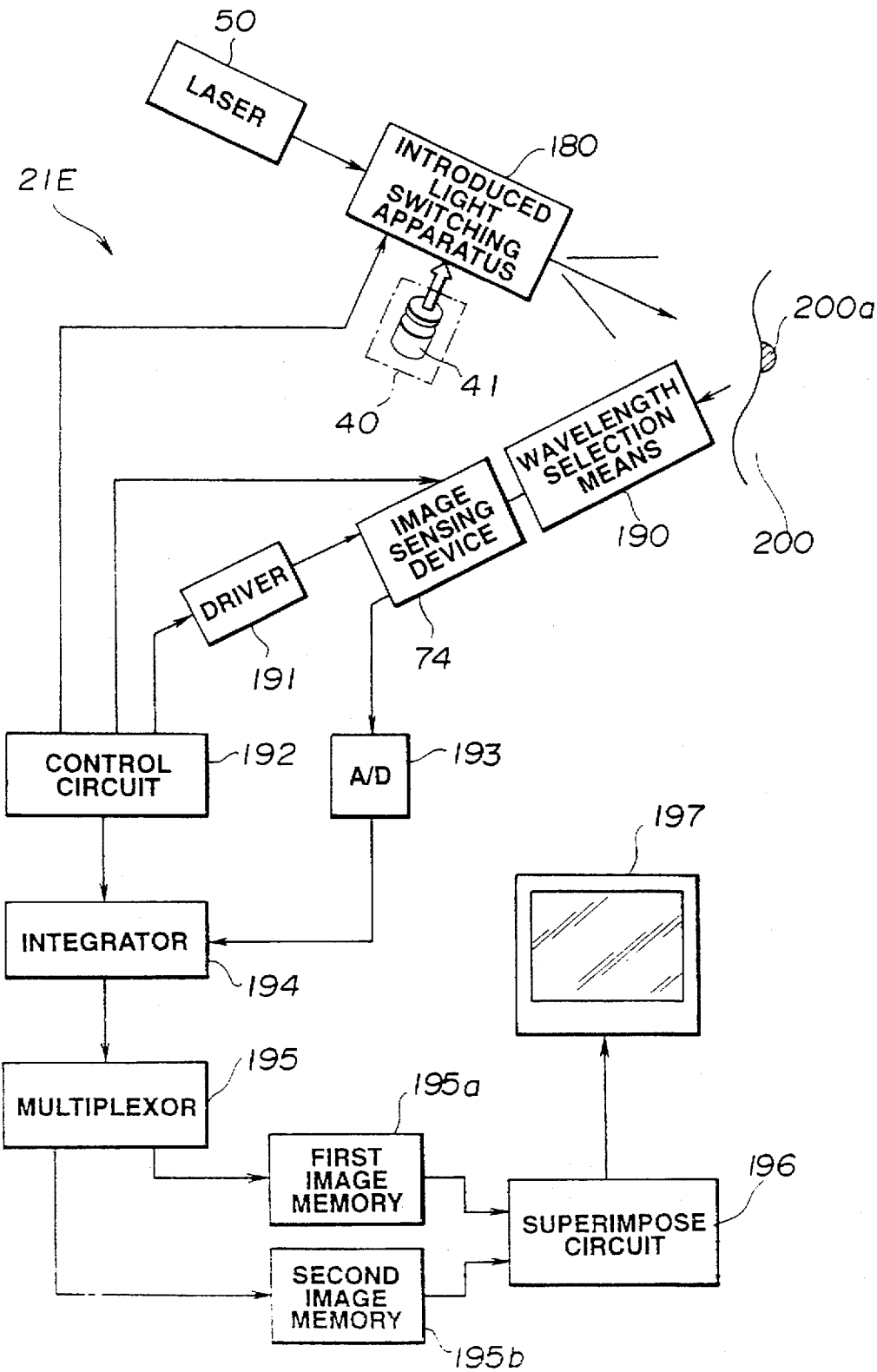
FIG. 13 illustrates a modification of the fluorescent endoscope apparatus shown in FIG.

A fluorescent endoscope apparatus 21E according to this example, as shown in FIG. 13, comprises: the fluorescent observation light source apparatus 50 for emitting excitation light; the normal observation light source apparatus 40 for emitting normal light; an introduced-light switching apparatus 180 for arbitrarily selecting excitation light or normal light; the image sensing device 74 for irradiating a subject portion to be observed with each light to capture reflected light or fluorescent light; a wavelength selection means 190 for selecting reflected light or fluorescent light; a driver 191 for operating the sensing device 74 at high speed, for example, from 30 to 2000 frames/sec; a control circuit 192 for synchronously controlling the introduced-light switching apparatus 140, the wavelength selection means 190 and the driver 191; an A/D converter 193 for converting data obtained by the image sensing device 74 into digital data; an integrator 194 for integrating the digital data; a multiplexor 195 for distributing a fluorescent image obtained due to the excitation light irradiation and a normal image to a first image memory 195a and a second image memory 195b, a superimpose circuit 196 for synthesizing images in the image memories 195a and 195b; and a monitor 197 for displaying the images.

Figure 14A:
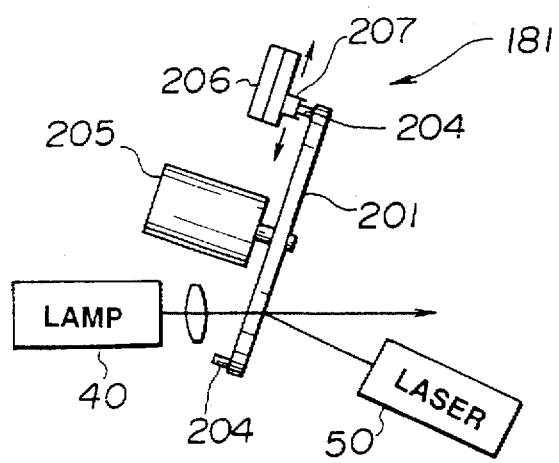
FIG. 14(a) is a side view which illustrates an example of a light source selection means of an introduced-light switching apparatus.
Figure 14B:
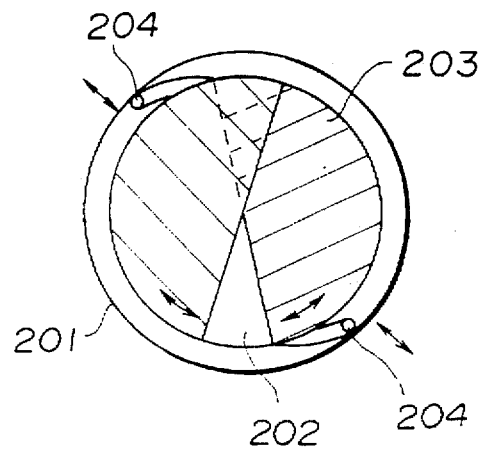
FIG. 14(b) is a front view which illustrates the light source selection means shown in FIG. 14(a)

FIG. 14 illustrates an example of the introduced-light switching apparatus 181. As shown in FIG. 14(a), the surface of a rotative plate 201 makes a predetermined angle from the optical axis to make the optical axis of the fluorescent observation light source apparatus 50 and that of the normal observation light source apparatus 40 coincide with each other. The rotative plate 201, as shown in FIG. 14(b), comprises a transmissive window 202 for permitting light to pass through and a reflecting mirror 203 for reflecting light, each of which is operated in synchronization with a projection portion 204 so that the angle of opening of the transmissive window 202 is changed.

That is, by moving the projection portion 204 by means of a groove 207 formed in a microstage 206 while rotating the rotative plate 201 by a stepping motor 205 to change the angle of opening so as to change the quantity of opening of the transmissive window 202, the ratio of excitation light to normal light can be changed. After the ratio has been set to an appropriate value, the groove 207 is retracted so that a state where the projection portion 204 cannot be introduced is realized.

FIG. 15 illustrates another introduced-light switching apparatus 182 comprising electronic shutters 211 and 212 disposed in front of the fluorescent observation light source apparatus 50 and the normal observation light source apparatus 40. An inversion circuit 213 is added to the electronic shutters 211 and 212. When either the electronic shutter 211 or electronic shutter 212 is inversely controlled, light is alternately emitted. The light beams allowed to pass through the electronic shutter are introduced into the same optical path through a dichroic mirror 214.

FIG. 16 illustrates a specific example of the wavelength selection means 190. As shown in FIG. 16(a), the wavelength selection means 190 comprises a cut filter 221 for cutting excitation light, a polarizing plate 222, a TN cell 223, and a liquid crystal filter 225 incorporating a color polarizing plate 224. As shown in FIG. 16(b), the liquid crystal filter 225 allows fluorescent light having the wavelength $\lambda 1$ or $\lambda 2$ that corresponds to the wavelength characteristics of the color polarizing plate which is turned on to pass through so as to introduce fluorescent light to the image sensing device 74 when the liquid crystal filter 225 is activated. When the liquid crystal filter 225 is deactivated, it allows light of all wavelength regions to pass through so as to introduce normal light into the image sensing device 74.

The operation of the thus-constituted fluorescent endoscope apparatus 21E will now be described.

Initially, excitation light emitted by the fluorescent observation light source apparatus 50 or normal light emitted by the normal observation light source apparatus 40 is selected by the introduced-light switching apparatus 180 and the selected light is applied to a subject portion 200 to be observed. Thus, fluorescent light or reflected light is generated in the vicinity of a diseased portion 200a in the subject portion 200 to be observed. The wavelength selection means 190, which is operated in synchronization with the introduced-light switching apparatus 180, selects a fluorescent image having the wavelengths $\lambda 1$ and $\lambda 2$ and a normal image from fluorescent light or reflected light. The selected images are formed on the image sensing device 74.

Then, an electrical signal formed on the image sensing device 74 and photoelectrically converted is converted by the A/D converter 193. Then, the digital data is integrated by the integrator 194 in accordance with the brightness of the fluorescent and normal images. The fluorescent image is distributed to the first image memory 195a, while the normal image is distributed to the second image memory 195b so as to be synthesized by the superimpose circuit 196 before the synthesized image is displayed on the monitor 197.

Figure 17:
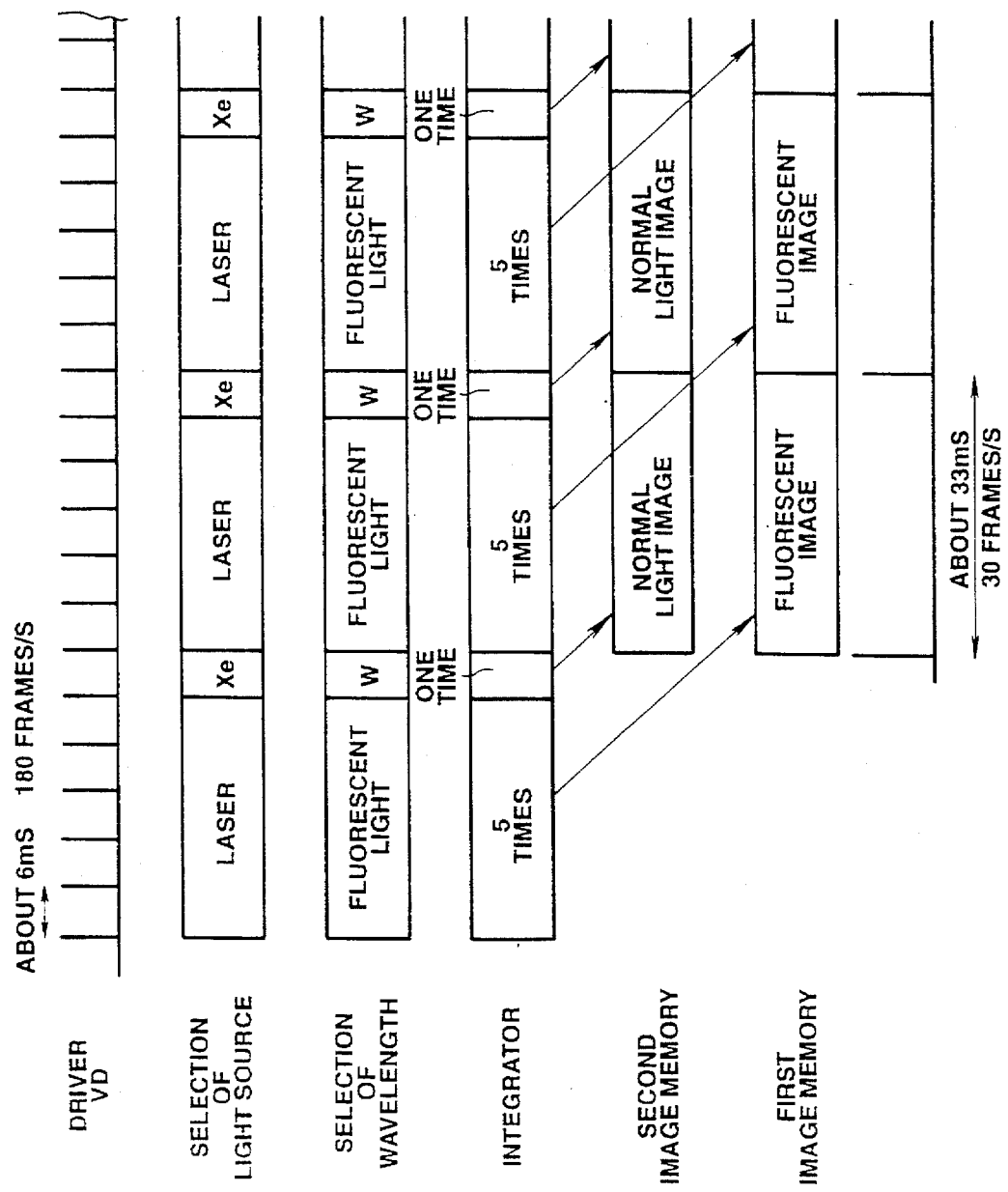
FIG. 17 is a timing chart explanatory of the operation.

At this time, the image sensing device 74 is operated at high speed of, for example, 180 frames/sec as shown in FIG. 17. If the sensitivity of the fluorescent image with respect to the observed image is raised by 5 times, the rate of time in which excitation light (expressed with "laser") is applied and time in which normal light (expressed with "Xe") is applied is made to be 5:1. Furthermore, the fluorescent images for five frames are integrated with respect to normal images for one frame to correspond to the ratio of time set as described above. Thus, the sensitivity of the fluorescent image can be improved. Symbol W represents an image formed by normal light.

As described above, both fluorescent image and the normal image can satisfactorily be displayed even if the brightness of the fluorescent image is changed. Furthermore, the S/N ratio can be improved by combining the two-dimensional lock-in amplifier 150.

A second embodiment of the present invention will now be described with reference to FIG. 18.

As contrasted with the first embodiment in which one camera is attached to the ocular portion of the endoscope to photograph the normal image and the fluorescent image, a fluorescent endoscope apparatus according to this embodiment has an arrangement where a camera switch apparatus is attached to the ocular portion of the endoscope. Furthermore, a camera for normal light for photographing a normal image and a camera for fluorescent light for photographing a fluorescent image obtainable due to the excitation light irradiation are attached to the camera switch means so that both normal image and the fluorescent image are observed.

Figure 18:
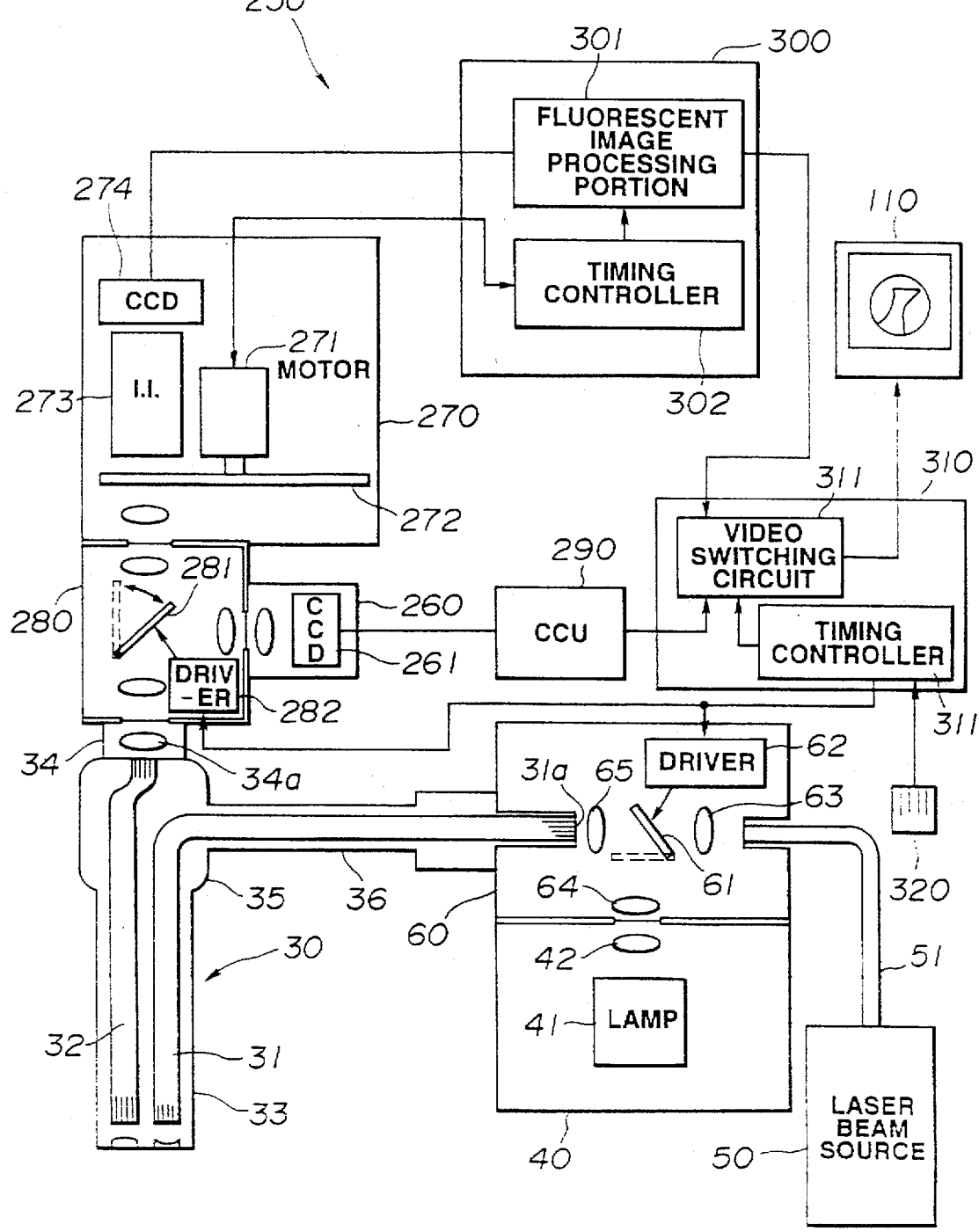
FIG. 18 illustrates the structure of a fluorescent endoscope apparatus according to a second embodiment of the present invention.

As shown in FIG. 18, a fluorescent endoscope apparatus 250 comprises: the fluorescent observation light source apparatus 50; a normal observation light source apparatus 40; the introduced-light switching apparatus 60 for selectively switching light beams respectively emitted by the foregoing light source apparatuses to the light guide of the endoscope 30; a normal observation camera 260 for photographing an image formed by normal light emitted by the normal observation light source apparatus 40; a fluorescent observation camera 270 for photographing a fluorescent image obtained by excitation light emitted by the fluorescent observation light source apparatus 50; a camera switch unit 280 for selectively switching the optical axis of the normal image or that of the fluorescent image obtained due to the excitation light irradiation, each of which is transmitted through the image guide 32 of the endoscope 30, to the optical axis of the normal observation camera 260 or that of the fluorescent observation camera 270; a CCU 290 for generating a normal image signal of the normal image photographed by the normal observation camera 260; a fluorescent image processing portion 300 having a fluorescent image processing portion 301 for generating a fluorescent image signal of the fluorescent image obtainable due to the excitation light irradiation and photographed by the fluorescent observation camera 270 and a timing controller 302 for controlling the rotation of a motor 271 of the fluorescent observation camera 270 to control the timing of a filter 272; and an observed-image control unit 310 having a video switch circuit 311 for switching between simultaneous display and time-division display of the fluorescent image signal and the normal image signal on the monitor 110.

The monitor 110 is connected to the image output terminal of the observed-image control unit 310.

The normal observation camera 260 has a CCD 261 to capture the normal image obtained by the endoscope 30.

The fluorescent observation camera 270 has a filter 272 which is rotated by the motor 271 and which allows the fluorescent component to pass through, an image intensifier (hereinafter abbreviated to "I.I.") 273 for amplifying the fluorescent image and a CCD 274 for capturing the fluorescent image. Thus, the fluorescent observation camera 270 photographs the fluorescent image of the subject portion to be observed that has been obtained by the endoscope 30. The filter 272 has a structure similar to that of the filter shown in FIG. 6 and comprises at least one type of a band-pass filter for permitting light in a wavelength band greater than excitation light λ0 to pass through. The filter 272 has a disc-like shape having, for example, two filters for permitting λ1 and λ2 band light beams to pass through. The filter 272 is rotated so that the light beams in the two bands are allowed to pass through the filter 272.

The camera switch unit 280, to which the normal observation camera 260 and the fluorescent observation camera 270 are connected, includes a switching mirror 281 for introducing the image obtained by the endoscope 30 to the fluorescent observation camera 270 or the normal observation camera 260, and a driver 282 for rotating the switching mirror 281.

The observed-image control unit 310 has a timing controller 311 for controlling the drivers 62 and 282 of the introduced-light switching apparatus 60 and the camera switch unit 280 to control the switching timing of the switching mirrors 61 and 281.

A foot switch 320 is connected to the observed-image control unit 310 so that the drivers 62, 282 and the video switch circuit 311 are switched in accordance with an instruction of switching issued from the foot switch 320.

When observation is performed with the fluorescent endoscope apparatus 250 according to this embodiment, the foot switch 320 is operated to switch the introduced-light switching apparatus 60 and the drivers 62 and 282 of the camera switch unit 280 to select the fluorescent light observation or the normal light observation.

When the fluorescent light observation is performed, the drivers 62 and 282 of the introduced-light switching apparatus 60 and the camera switch unit 280 are switched to the fluorescent observation light source apparatus and to the fluorescent observation camera. Thus, the subject portion to be observed is irradiated with excitation light emitted by the fluorescent observation light source apparatus 50. A fluorescent image obtained due to the irradiation with excitation light is, through the filter 272 of the fluorescent-light camera 270, amplified by the image intensifier (I.I.) 273 to about 10,000 times before it is captured by the CCD 274. A fluorescent image signal is generated by the fluorescent image processing apparatus so that a fluorescent image is displayed on the monitor 110.

When the normal endoscope observation is performed, the drivers 62 and 282 of the introduced-light switching apparatus 60 and the camera switch unit 280 are switched to the normal observation light source apparatus and the normal-light camera so that the subject portion to be observed is irradiated with normal light emitted by the normal observation light source apparatus 40. A normal image is, then, captured by the CCD 261 of the normal observation camera 260. Then, the CCU 290 generates a normal image signal and the observed normal image is displayed on the monitor 110. Elements similar to those according to the first embodiment are given the same reference numerals and their descriptions are omitted here.

By attaching the camera switch unit to the endoscope and by attaching the normal observation camera and the fluorescent observation camera to the camera switch unit as described above, the fluorescent observation using excitation light and the normal light observation can easily be switched.

Furthermore, the simple operation of the foot switch enables switching between the fluorescent light observation using excitation light and the normal light observation to be performed easily. The other operations and effects are the same as those of the first embodiment.

The switch for switching between the fluorescent light observation using excitation light and the normal observation using normal light is not limited to the foot switch. Other types of switches may be employed.

A light-quantity control means will now be described which always irradiates the subject portion to be observed with excitation light in an adequate quantity to perform optimum fluorescent observation with the fluorescent endoscope apparatus according to the first and second embodiments.

Figure 19:
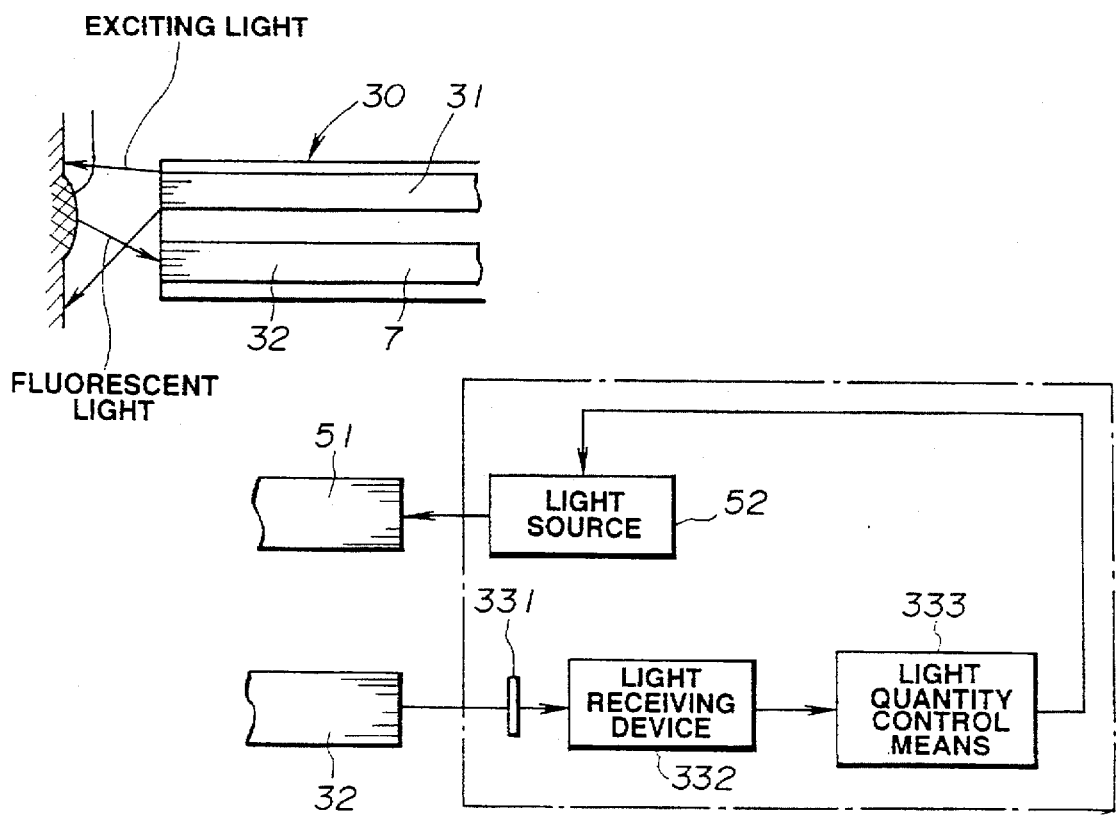
FIG. 19 illustrates an essential portion of the fluorescent endoscope apparatus for controlling the light quantity.

For example, an end of the light guide cable 51 is connected to the fluorescent observation light source apparatus 50. An incidental end of the light guide cable 51 is, as shown in FIG. 19, disposed at the emission end of the laser 52. The light quantity of the laser 52 is controlled by the structure arranged as illustrated.

That is, a blocking filter (for example, a 442nm cut filter that removes wavelength band 350 nm to 500 nm) 331 and a light receiving device 332 comprising a photodiode are disposed in the ocular portion of the image guide 32 included in the endoscope 30. The light receiving device 332 receives the fluorescent component of light reflected by the subject portion to be observed. The light receiving device 332 is connected to the light-quantity control means 333 so that the quantity of light reflected by the subject portion to be observed is detected in accordance with the output from the light receiving device 332, the detected value being then transmitted to the light-quantity control means 333. The light-quantity control means 333 is connected to the laser 52 to transmit, to the laser 52, a control signal in accordance with the quantity of reflected light received by the light-quantity control means 333. Thus, the quantity of light to be emitted by the laser 52 is controlled so that the output from the light receiving device 332 is a predetermined quantity.

The specific configuration and structure of the light receiving device 332 and the light-quantity control means 333 for controlling the quantity of light will now be described with reference to FIG. 20.

Figure 20:
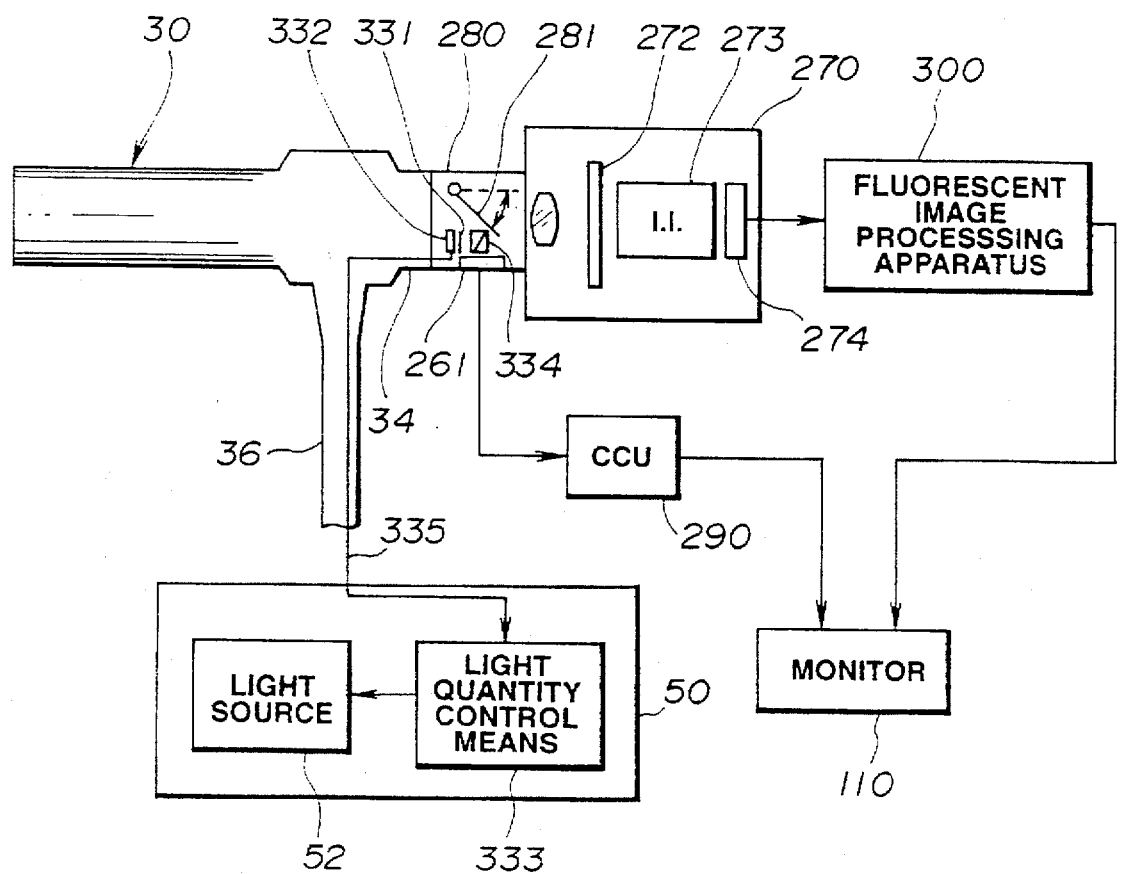
FIG. 20 illustrates an example in which a light-quantity control means is provided for the fluorescent endoscope apparatus.

As shown in FIG. 20, the camera switch unit 280 has a switching mirror 281 for performing switching between the normal image and the fluorescent image obtained by the endoscope 30. Furthermore, the CCD 261 for capturing a normal endoscope image through a light dividing device 334, such as a prism, the filter 331 and the light receiving device 332 are disposed on the side of the switching mirror 281. The light receiving device 332 is, through a signal line 335 passing through the universal cord 36, connected to the light-quantity control means 333 disposed in the fluorescent observation light source apparatus 50 so as to transmit a control signal corresponding to the quantity of reflected light to the laser 52.

When the fluorescent light observation is performed, the subject portion to be observed is, through a light guide (not shown) of the endoscope 30, irradiated with excitation light generated by the laser 52 of the fluorescent observation light source apparatus 50. Thus, the subject portion to be observed generates fluorescent light longer than excitation light in response to irradiating excitation light. Thus-generated fluorescent light is allowed to pass through the image guide in the endoscope 30 to be made incident upon the camera switch unit 280 so as to be captured by the CCD 274 through the I.I. 273. Then, the captured signal photoelectrically converted by the CCD 274 is processed by the fluorescent image processing apparatus 300 so that the photography signal is displayed on the monitor 110 as the observed fluorescent image. At this time, light reflected by the subject portion to be observed is received by the light receiving device 332 which then transmits, to the light-quantity control means, an output signal corresponding to the received quantity of fluorescent light. That is, the light-quantity control means 333 reads the output signal from the light receiving device 332 to detect the quantity of fluorescent light and transmits a control signal with which the output (irradiating light) from the light source is controlled so as to always make the quantity of the fluorescent light to be a predetermined value, for example, a constant value. Thus, the quantity of light emitted by the laser 52 is controlled.

By providing the light receiving device for controlling the quantity of light for the camera switch unit as described above, the quantity of fluorescent light obtained from the subject portion to be observed is read so that the quantity of light emission from the light source can be adjusted to obtain reflected light in a predetermined quantity even if the state of the subject portion to be observed is changed. As a result, the subject portion to be observed can always be irradiated with excitation light in an adequate quantity to correspond to the state of the subject portion to be observed. Therefore, fluorescent light can be satisfactorily obtained from the subject portion to be observed regardless of the state of the subject portion to be observed and a fluorescent light observation image, with which a desired diagnosis can be performed, can be obtained.

Figure 21:
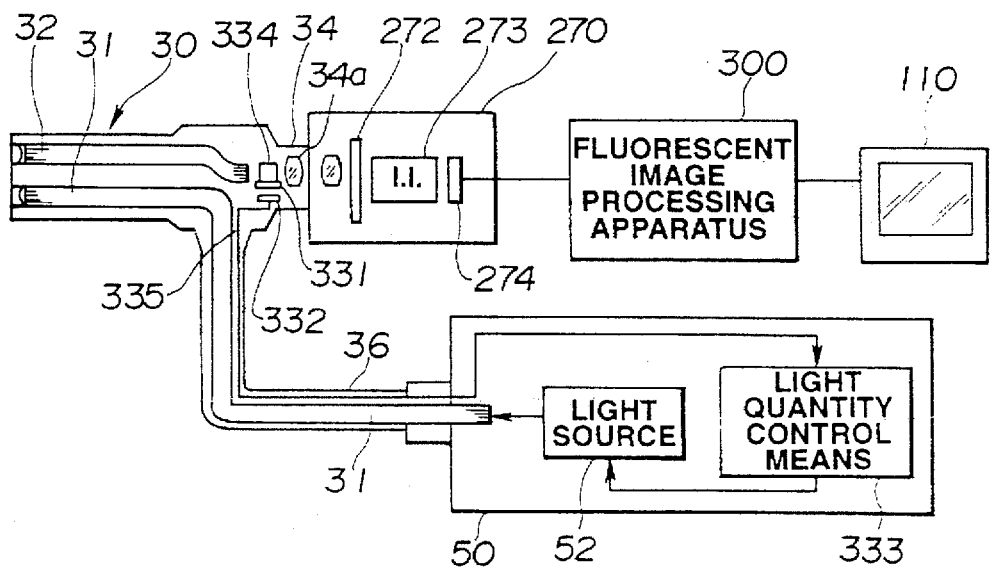
FIG. 21 illustrates an example in which the light-quantity control means is provided for an endoscope of the fluorescent endoscope apparatus.

Note that a structure as shown in FIG. 21 may be employed in which the light dividing device 334 is disposed in the optical path connecting, with each other, the end of the image guide 32 disposed in the ocular portion 34 in the base portion of the insertion portion of the endoscope 30 and the optical lens 34a of the ocular portion 34. Thus, the light dividing device 334 causes a portion of the fluorescent image that transmits through the image guide 32 to be received by the light receiving device 332 through the filter 331. Furthermore, the signal line 335 extending from the light receiving device 332 is connected to the light-quantity control means 333 provided for the fluorescent observation light source apparatus 50.

By causing the fluorescent endoscope apparatus according to the first embodiment to employ the fluorescent observation light source apparatus 50 having the light-quantity control means 333, a similar control can be performed.

An example will now be described which makes uniform the dispersion of the intensity distribution of fluorescent light occurring due to the characteristics of the lens, the fiber and so forth included by the endoscope and thus enables further accurate diagnosis to be performed.

Figure 22:
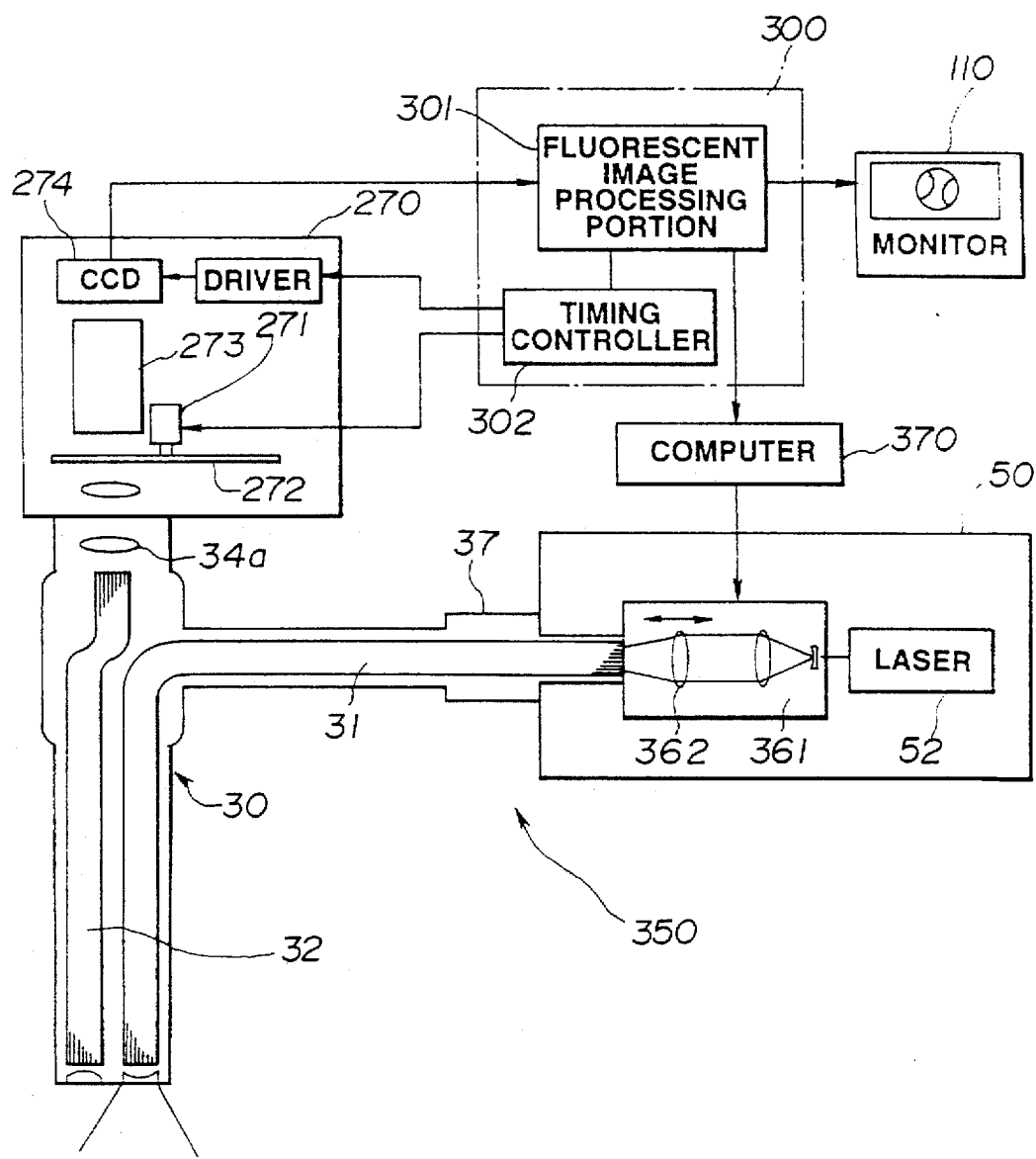
FIG. 22 illustrates a specific example of the light-quantity control means.

As shown in FIG. 22, an endoscope apparatus 350 for the fluorescent observation according to this example comprises the fluorescent observation light source apparatus 50 for generating excitation light, the endoscope 30 for irradiating a subject portion to be observed with excitation light emitted by the fluorescent observation light source apparatus 50 to detect and transmit fluorescent light, the fluorescent observation camera 270 for photographing the fluorescent image at high sensitivity to convert it into an electrical signal, the fluorescent image processing apparatus 300 for processing the image obtained by the fluorescent observation camera 270 to obtain the distribution of the intensities of fluorescent light and to perform inter-image calculation, and a computer 370 for controlling a light-distribution adjustment means 360 included in the fluorescent observation light source apparatus 50 in accordance with the obtained distribution of the intensities of fluorescent light.

Initially, excitation light is generated by the laser 52 included in the fluorescent observation light source apparatus 50. Excitation light is, through the light-distribution adjustment means 360, introduced into the light guide 31 of the endoscope 30. The light-distribution adjustment means 360 comprises a beam expander portion 361 and a converging lens 362 which is able to move in the direction of the optical axis. By moving the converging lens 362, the distribution of excitation light can be changed. The position of the converging lens 362 is adequately controlled by the computer 370.

Excitation light passing through the light guide 31 of the endoscope 30 is used to irradiate the subject portion to be observed. Fluorescent light generated by the subject portion to be observed is allowed to pass through the image guide 32 and the ocular lens 34a so that fluorescent light is made incident on the fluorescent observation camera 270. The fluorescent image made incident on the fluorescent observation camera 270 is allowed to pass through the rotative filter 272 and the I.I. 273 and then it is captured by the CCD 274.

The fluorescent image obtained by the CCD 274 is supplied to the fluorescent image processing portion 301 so that inter-image calculation for each wavelength band is performed. A pseudo-color image corresponding to the results of the foregoing calculations is displayed on the monitor 110. On the other hand, the distribution of the intensities of the fluorescent image is analyzed by the computer 370 to control the position of the converging lens 362 of the fluorescent observation light source apparatus 50 in order to make the distribution uniform. The adjustment of the light distribution is previously performed at a standard observation position before the endoscope observation is performed, the result of the adjustment being held during the inspection with the endoscope.

Since the distribution of light emitted by the light source can be changed in accordance with the fluorescent image as described above, an excellent fluorescent image can be obtained even if the endoscope is changed and thus the optical characteristics are changed.

Use of an 8 μm or thicker element in the image fiber will enable further stable diagnosis to be performed using fluorescent light without decay of red wavelength longer than 600 nm.

Figure 23:
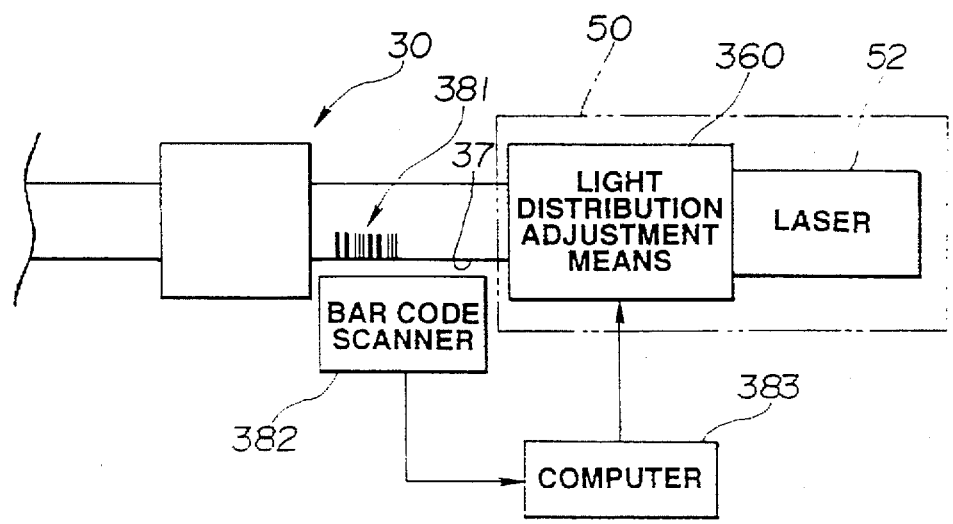
FIG. 23 illustrates the relationship between a light distributing means and the endoscope.

Furthermore, a bar code 381 having the type of the endoscope 30 or data of light distribution of the same written thereon is, as shown in FIG. 23, provided for the light guide receiver connector 37 of the endoscope 30 shown in FIG. 22. In addition, the fluorescent endoscope apparatus comprises a bar code scanner 382 for reading the bar code 381 and a computer 383 for controlling the light-distribution adjustment means 360 that changes the light distribution to obtain an optimum fluorescent image in accordance with data of the bar code 381. When the light guide connector receiver 37 of the endoscope 30 is inserted into the fluorescent observation light source apparatus 50, the bar code 381 including the type or the light distribution data of the endoscope 30 is read by the bar code scanner 382. In accordance with the result of reading, the computer 383 controls the light-distribution adjustment means 360. Thus, the type of the endoscope is previously detected and the light distribution suitable for the type of the endoscope is made. As a result, an optimum light distribution can be realized without a necessity of previously performing light distribution adjustment with respect to the subject portion to be observed.

The light distribution adjustment means is not limited to the type described above. The following structure may be employed. Another example will now be described with reference to FIGS. 24(a)–24(b).

Figure 24A:
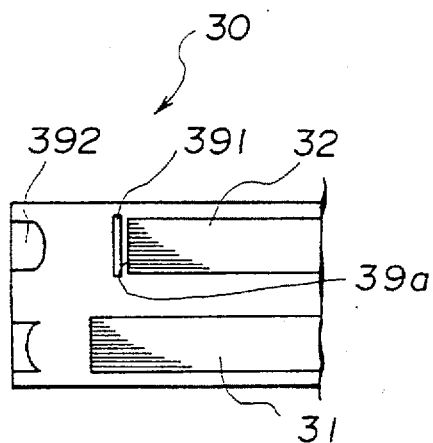
FIG. 24(a) illustrates an endoscope including an optical filter having an absorption distribution.

In this embodiment, an optical filter 391 serving as a light distribution adjustment means and having an absorption distribution is, as shown in FIG. 24(a), disposed in front of the leading surface 32a of the image guide 32 of the endoscope 30 in such a manner that the distribution of the intensities of fluorescent light is made to be uniform. The other structures are similar to those shown in FIG. 22 and therefore only different portions will now be described.

Figure 24B:
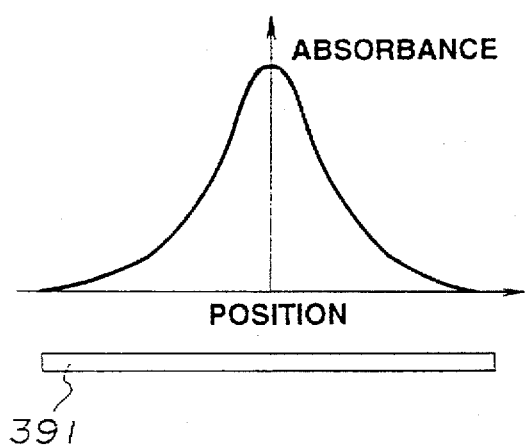
FIG. 24(b) is a characteristic graph of the absorbance of the optical filter.

The optical filter 391 has a high absorbance at the central portion thereof and the absorbance is lowered toward the periphery thereof as shown in FIG. 24(b).

If a fluorescent image is formed on the end surface of the image guide 32 through an objective optical system 392, the optical filter 391 disposed in front of the image guide 32 causes the fluorescent image to be formed in such a manner that its periphery is made brighter than the central portion.

On the other hand, the normal image tends such that the periphery is darker than the central portion. If distortion correction of the objective optical system 392 is performed, also the periphery is easily made to be darker. Since the incident light beam is inclined by 3° to 6° in the periphery of the end surface of the image guide 32 as compared with the central portion, the peripheral portion is similarly made to be darker. That is, the optical filter 391 as shown in FIG. 24(b) is previously disposed in front of the image guide 32 so that the light distribution can be made to be uniform.

The optical filter 391 may have wavelength characteristics. For example, a filter having a specific absorbance distribution with respect to only light of 600 nm wavelength or longer and a filter having a specific absorbance distribution with respect to only light having wavelengths from 480 nm to 520 nm may be combined. As an alternative to this, either of the foregoing filters may be used. Thus, correction for each wavelength can be performed. The optical filter 391 may be provided in the vicinity of the ocular portion.

The disposition of the optical filter having the absorbance distribution in the endoscope eliminates the necessity of using a special light distribution adjustment means. Therefore, a fluorescent endoscope apparatus having a light distribution adjustment means can be constituted with a reduced cost.

Another example will now be described with reference to FIG. 25.

In this embodiment, a correction table corresponding to each wavelength to be detected is disposed to correct the distribution of the intensities of fluorescent light for each wavelength to be detected. Thus, a fluorescent endoscope apparatus which is capable of precisely performing diagnosis is provided according to this embodiment.

Figure 25:
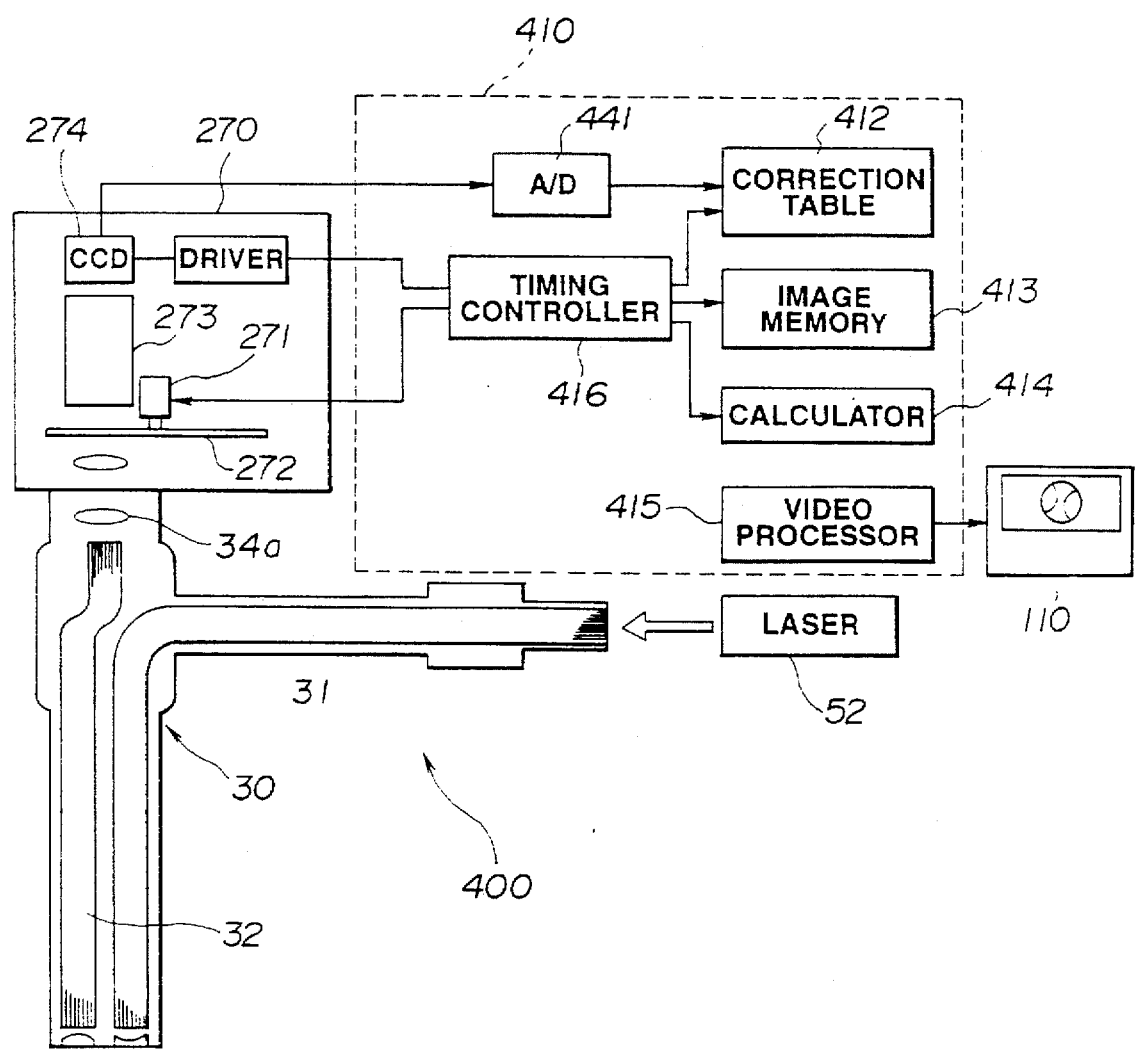
FIG. 25 illustrates a fluorescent endoscope apparatus for correcting the fluorescent light intensity distribution.

As shown in FIG. 25, a fluorescent endoscope apparatus 400 comprises an image processing apparatus 410 for processing a fluorescent image obtained by directly introducing irradiating light emitted by the laser 52 into the light guide 31. The image processing apparatus 410 is constituted by an A/D converter 411 for converting a video signal supplied from the CCD 274 into digital data, a correction table 412 for correcting the fluorescent image for each wavelength, an image memory 413 for storing images, a calculator 414 for calculating each image data, a video processor 415 for making a diseased portion to be an image (for example, a pseudo-color image) that can easily be recognized in accordance with the result of the calculation, and a timing controller 416 for controlling the timing of the motor 271, the correction table 412, the image memory 413 and the calculator 414 for dividing the fluorescent image into each wavelength before it is processed. The other structures are the same as those shown in FIG. 22. The same elements are given the same reference numerals and their descriptions are omitted here.

The fluorescent endoscope apparatus 400 according to this example has an arrangement that excitation light generated by the laser 52 is directly introduced into the light guide 31, and fluorescent light generated from excitation light is subjected to a correction of the distribution of the intensities of fluorescent light to be performed in the image processing apparatus 410. The corrected data is displayed on the monitor 110.

Initially, the A/D converter 411 converts the signal obtained by the CCD 274 into digital data. The digital data of the image is corrected by the correction table 412 for each wavelength. The correction coefficient is feedback-adjusted in such a manner that the distribution of fluorescent light for each wavelength is previously obtained in a standard subject portion to be observed and the obtained distribution is made to be uniform. The corrected data is, for each wavelength, stored in the image memory 413. Then, the calculator 414 calculates the difference of the ratio between the wavelengths, the results being then converted into an image signal in a pseudo-color by the video processor 415 before it is displayed on the monitor 110. Since the correction for each wavelength to be detected can be performed, the accuracy in diagnosis can be improved.

Figure 26:
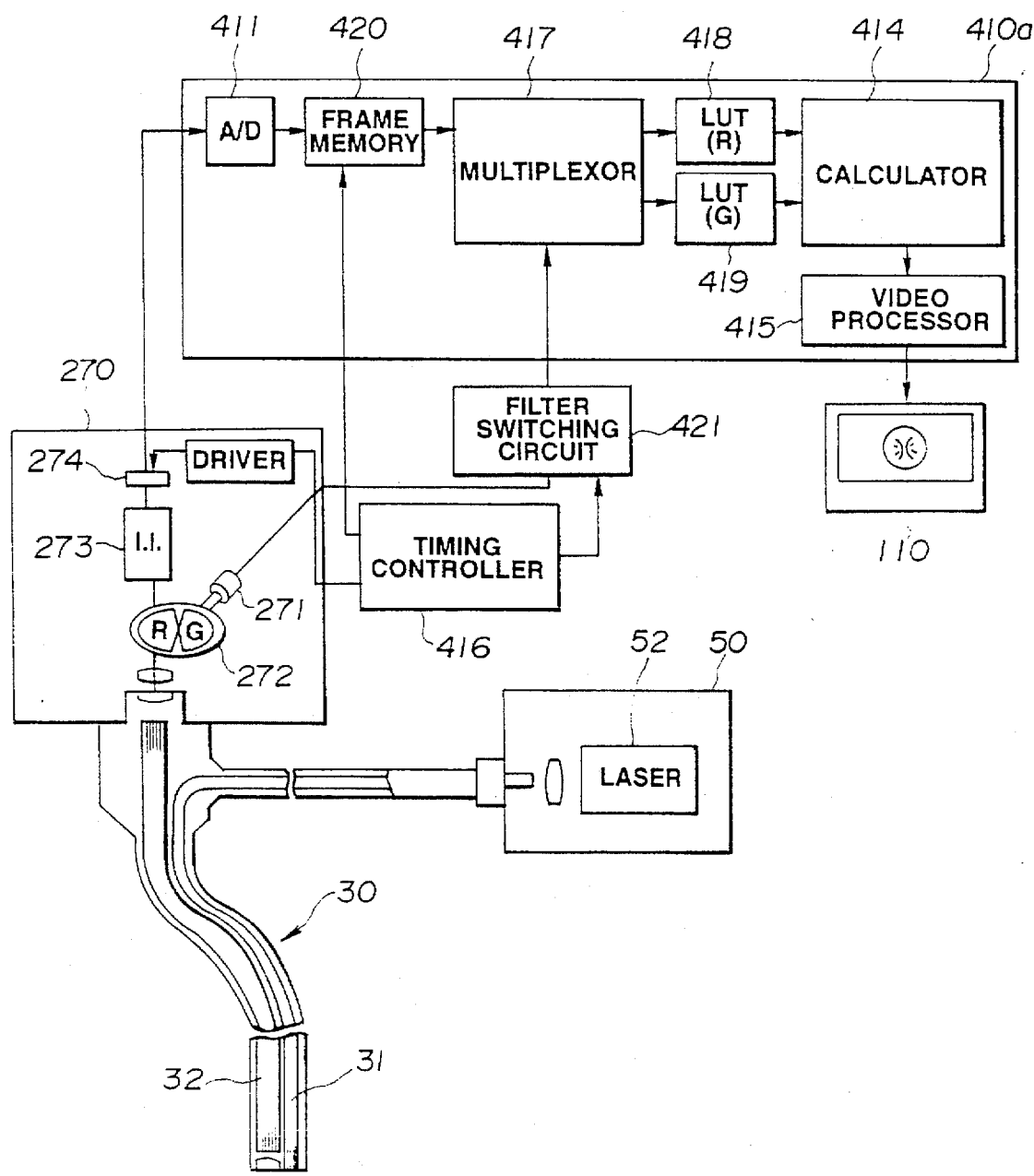
FIG. 26 illustrates a modification of FIG. 25.

A fluorescent endoscope apparatus 401 according to a modification to the example shown in FIG. 25 is shown in FIG. 26. The image processing apparatus 410a has an arrangement that digital data supplied from the A/D converter 411 is stored in a frame memory 420. Fluorescent light image data is, for each red, green data and through a multiplexor 417, corrected by using lookup tables (hereinafter abbreviated to an "LUT") LUT (R) 418 and LUT (G) 419 (R'=f1 (R), G'=f2 (G) where f1 and f2 are correction functions). The multiplexor 417, in response to the timing controller 416, causes a filter switching portion 421 to perform switching between the LUT (R) 418 and the LUT (G) 419 in synchronization with the rotative filter 272.

Figure 27:
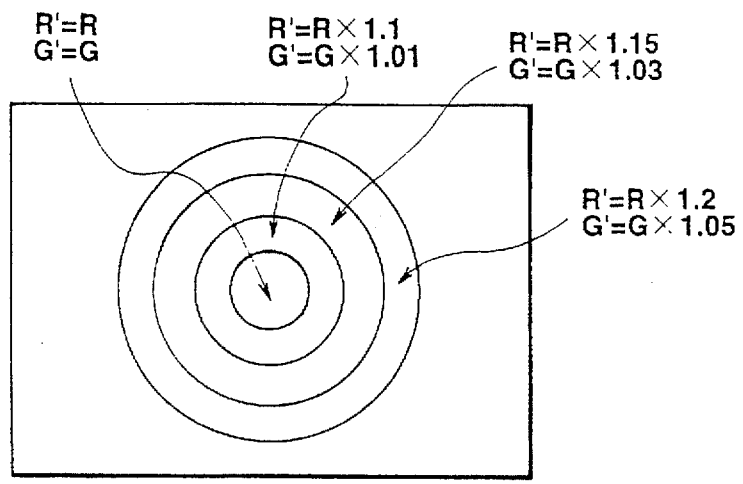
FIG. 27 illustrates an example of correction to be performed with a lookup table.

The LUT (R) 418 and the LUT (G) correct data in such a manner that data is changed in a circular and stepped manner for example as shown in FIG. 27. That is, the correction proceeds from the innermost portion toward the outermost portion such that (R'=R, G'=G), (R'=R×1.1, G'=G×1.01), (R'=R×1.15, G'=G×1.03), (R'=R×1.2, G'=G× 1.05).

An example of the structure of a fluorescent endoscope apparatus will now be described which is capable of reducing the size of the means for amplifying a fluorescent image and reducing the size of the fluorescent observation camera.

Figure 28:
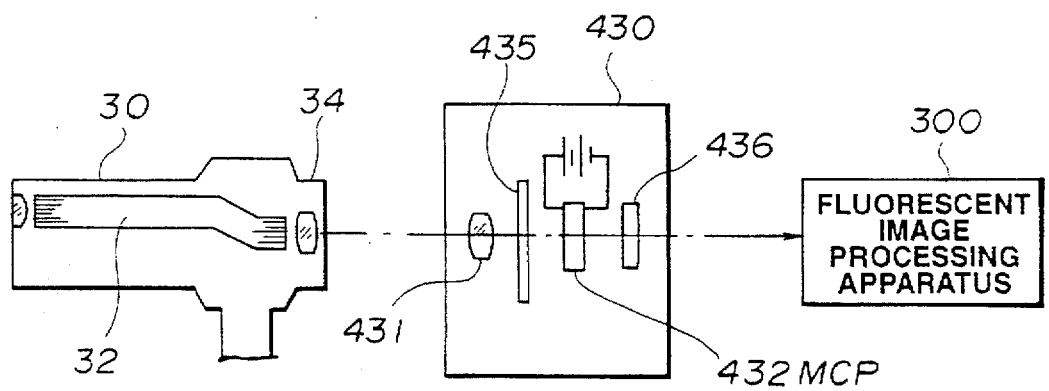
FIG. 28 illustrates a fluorescent light amplifying means of a fluorescent-light camera.
Figure 29:
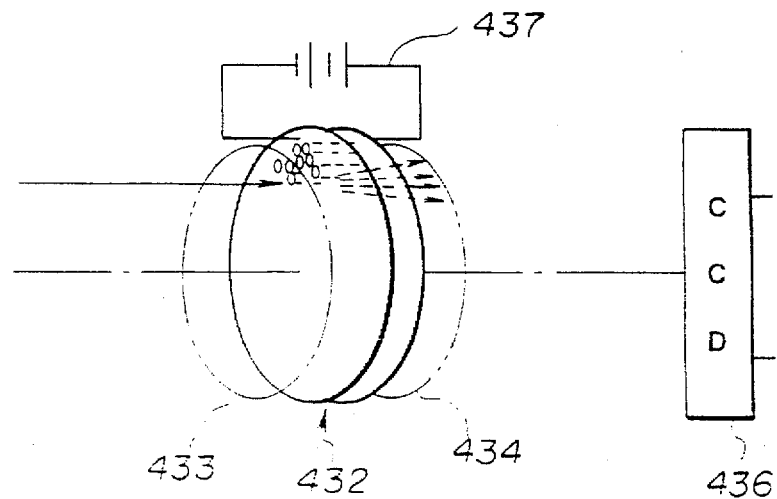
FIG. 29 illustrates the structure of an MCP which is a fluorescent image amplifying means.

FIGS. 28 and 29 illustrate an example of the structure of the fluorescent endoscope apparatus having the means for amplifying the fluorescent image, the size of which is reduced. FIG. 28 illustrates the schematic structure of a portion including the fluorescent observation camera. FIG. 29 illustrates the schematic structure and the operation of an MCP serving as the means for amplifying a fluorescent image.

A fluorescent observation camera 430, which is connected to the ocular portion 34 of the endoscope 30 when the fluorescent observation is performed, comprises an objective lens 431, a filter 435 for permitting a fluorescent component to pass through, an MCP (Micro Channel Plate also called, for example, a proximity and converging type MCP-I.I.) serving as the amplifying means for amplifying the fluorescent image that has passed through the filter 435, and a CCD 436 for capturing an output image from the MCP 432. Thus, a photography signal is transmitted to the fluorescent image processing apparatus 300.

An image obtained by irradiating the subject portion to be observed with light and transmitted through the image guide in the endoscope 30 is allowed to pass through the objective lens 431 of the fluorescent observation camera 430. Then, the excitation light component is removed from the image by the filter 435 and the image is made incident on the MCP 432. The MCP 432 has a multiplicity of small diameter channels formed in a thin plate as shown in FIG. 29 and comprises a photoelectric surface 433 and a fluorescent surface 434 on the two longitudinal ends thereof.

Light made incident on the MCP 432 is allowed to pass through the photoelectric surface 433 and caused to generate electrons in each channel of the MCP 432. When a predetermined voltage 437 is applied to the electrodes on the two sides, it is amplified and amplified light is transmitted through the fluorescent surface 434. Light of the fluorescent image made incident on the MCP 432 is amplified from 1,000 to 10,000 times before it is made incident on the CCD 436.

Therefore, the MCP 432 amplifies the weak fluorescent image of the subject portion to be observed so that the fluorescent image is formed into a visible ray image that can be captured by the CCD 436. The MCP 432 has a size significantly smaller than a usual I.I. and exhibits flux image multiplication equivalent to a cascade-type I.I. Thus, it is possible to obtain light of desired intensity from weak fluorescent light while occupying only a small space. In the CCD 436, the fluorescent image is photoelectrically converted into an electric signal so as to be transmitted to the fluorescent image processing apparatus 300 as a photography signal. Thus, the photography signal is signal-processed so that an observed fluorescent image is displayed on the monitor.

Since the foregoing disposition of the MCP serving as the means for amplifying the fluorescent image for the fluorescent camera in front of the CCD in place of the I.I. as described above, the size of the means for amplifying the fluorescent image can be reduced. Thus, the size and weight of the fluorescent observation camera can be reduced. As a result, when the fluorescent observation camera is attached to the ocular portion of the endoscope, the need for using a means for supporting a camera can be eliminated and the fluorescent observation camera or the control portion can be held and operated. Therefore, the operationality at the time of performing the fluorescent light observation can be improved. The structure in which the MCP is disposed in the vicinity of the control portion of the endoscope near the operator and the filter and the MCP and the CCD are disposed adjacently to the light emission end of the image guide enables a fluorescent image having a desired brightness to be obtained by the endoscope. Thus, the size of the apparatus can be reduced and the operationality can further be improved.

A fluorescent image involves distortion of the image mainly in the periphery thereof such that the intensity of fluorescent light is weakened in the periphery thereof, thus causing the periphery of the fluorescent image to be darkened. That is, even if an object having completely uniform spatial fluorescent characteristics is captured, a portion, the S/N ratio of which deteriorates, is generated due to distortion of the fluorescent image that causes the difference in the intensity of fluorescent light to arise. As a result, when a distinction between a healthy portion and a diseased portion is performed, an error will take place in the diagnosis using fluorescent light in a portion having unsatisfactory S/N ratio. The following example is intended to overcome the foregoing problem.

Figure 30:
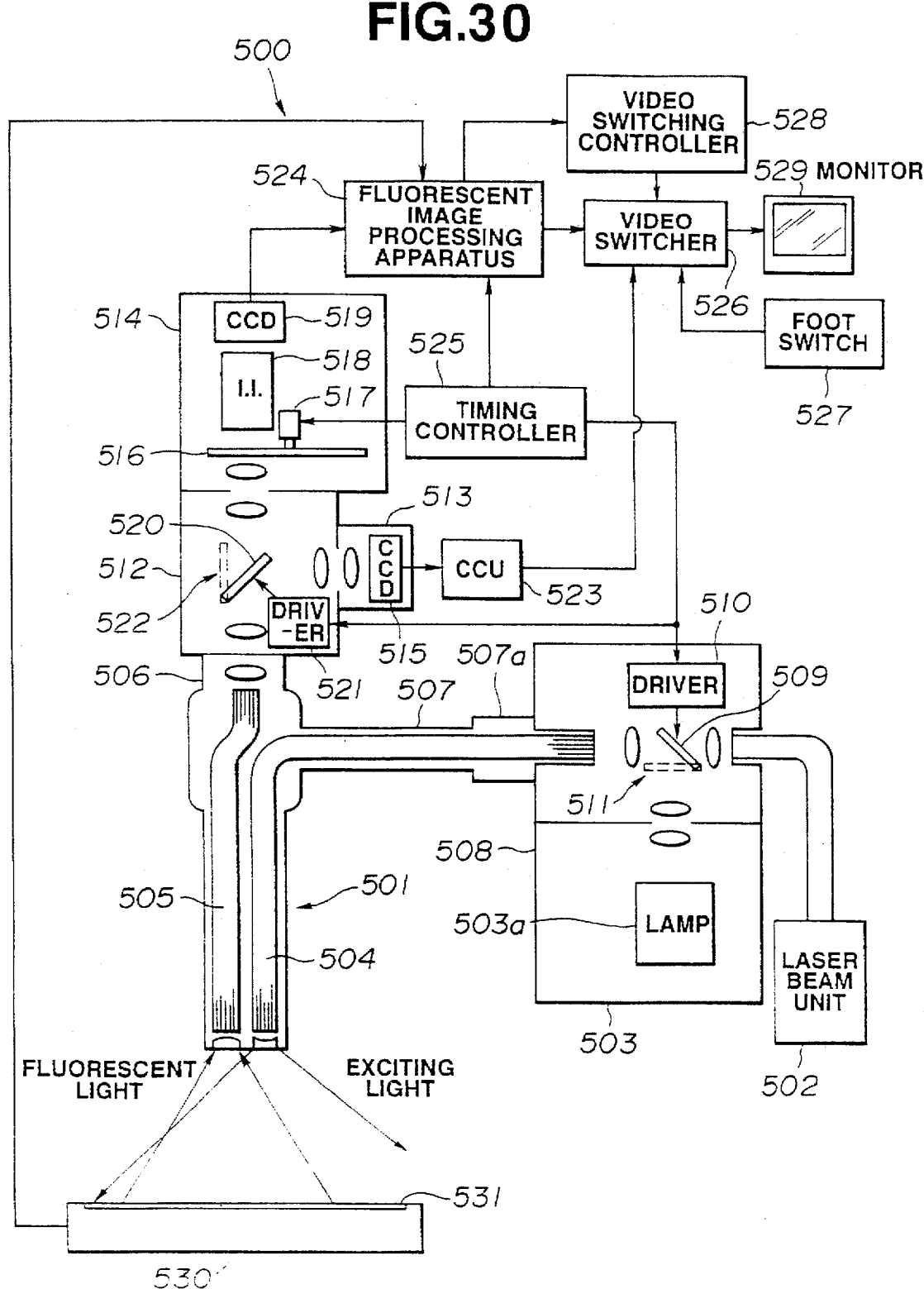
FIG. 30 illustrates a fluorescent endoscope apparatus capable of improving the S/N ratio.
Figure 31:
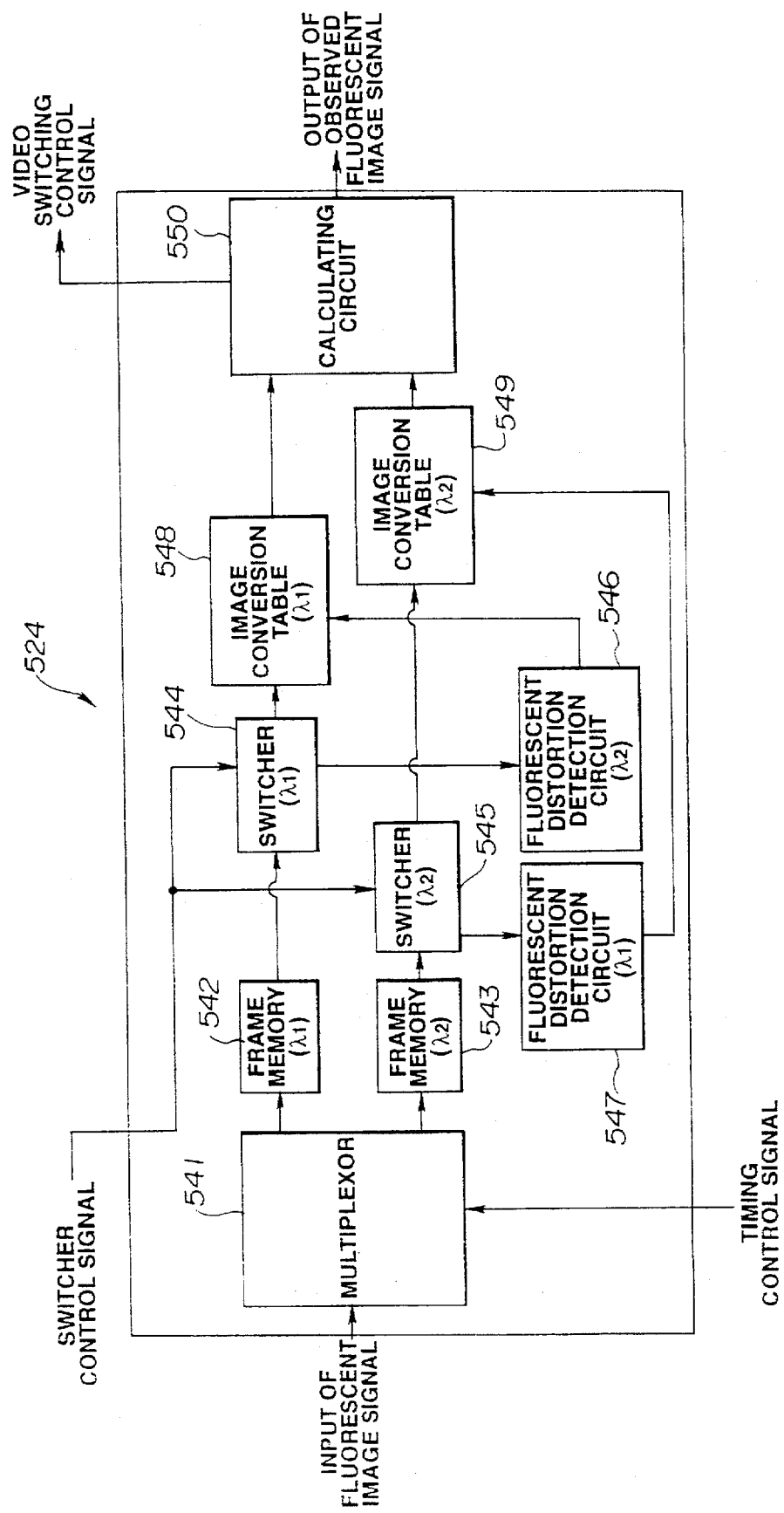
FIG. 31 is a block diagram which illustrates a fluorescent endoscope apparatus.

As shown in FIGS. 30 to 32, a fluorescent endoscope apparatus 500 according to this example comprises an endoscope 501 for introducing excitation light into a subject portion to be observed and forming an image of fluorescent light emitted by the subject portion to be observed. The fluorescent endoscope apparatus 500 further comprises a fluorescent observation light source apparatus 502 for generating excitation light and a normal observation light source apparatus 503 having a lamp 503a, such as a xenon lamp, for generating normal light.

A light guide 504 for transmitting light emitted by the fluorescent observation light source apparatus 502 or the normal observation light source apparatus 503 and an image guide 505 for transmitting an observed image to an ocular portion 506 are inserted into the endoscope 501. The light guide 504 is inserted into a universal cord 507 to extend to a light guide connector 507a disposed at an end of the universal cord 507.

The fluorescent observation light source apparatus 502 and the normal observation light source apparatus 503 are connected to an introduced-light switching apparatus 508 for switching light to be introduced into the endoscope 501. The light guide connector 507a of the endoscope 501 is connected to the introduced-light switching apparatus 508. Thus, excitation light emitted by the fluorescent observation light source apparatus 502 or normal light emitted by the normal observation light source apparatus 503 is, through the introduced-light switching apparatus 508, introduced into the light guide 504 of the endoscope 501.

The introduced-light switching apparatus 508 comprises a movable mirror 509 disposed in an optical path for light emitted by each light source apparatus and a driver 510 for operating the movable mirror 509. By selectively switching the movable mirror 509, excitation light or normal light can be introduced to the rear end surface of the light guide 504.

A camera switch unit 512 is connected to the ocular portion 506 of the endoscope 501. A normal-light camera 513 and a fluorescent-light camera 514 are connected to the camera switch unit 512. Thus, each photographing means is able to photograph a normal image and a fluorescent image.

The normal-light camera 513 has a CCD 515 which serves as an imaging optical system to capture an image of a subject portion to be observed which has been irradiated with normal light emitted by the normal observation light source apparatus 503. The fluorescent-light camera 514 comprises a drive motor 517 for rotating the rotative filter 516, an I.I. 518 for amplifying an image which has transmitted through the rotative filter 516, and a CCD 519 for capturing an output image from the I.I. 518 so as to capture a fluorescent image of the subject portion to be observed that can be obtained by irradiating the same with excitation light emitted by the fluorescent observation light source apparatus 502.

The rotative filter 516 has a band-pass filter of a type, for example, λ1=480 nm to 520 nm and a band-pass filter of a type, for example, λ2=630 nm or longer, the rotative filter 516 being formed into a disc-like shape. When the rotative filter 516 is rotated, the foregoing filters are sequentially inserted into the optical path so that a fluorescent component in each band is allowed to pass through.

The camera switch unit 512 comprises a movable mirror 520 disposed in the optical path for the image transmitted to the ocular portion 506 of the endoscope 501 and a driver 521 for operating the movable mirror 520. By selectively changing the movable mirror 520, an image of an object obtained by the endoscope 501 can be introduced into the normal-light camera 513 or the fluorescent-light camera 514.

A CCU 523 is connected to the normal-light camera 513 to receive a photography signal, which is the output from the CCD 515. The photography signal is signal-processed by the CCU 523 so that an observed normal image signal is generated. A fluorescent image processing apparatus 524 is connected to the fluorescent-light camera 514 to receive a photography signal supplied by the CCD 519 so that the photography signal is processed in the fluorescent image processing apparatus 524. Thus, a fluorescent image signal is generated.

A timing controller 525 for controlling each operation timing is provided so as to transmit a timing signal to each of the driver 510 for the introduced-light switching apparatus 508, the driver 521 for the camera switch unit 512, the drive motor 517 for the rotative filter 516 and the fluorescent image processing apparatus 524.

The CCU 523 and the fluorescent image processing apparatus 524 are connected to a video switcher 526 so that the observed normal image signal, which is the output from the CCU 523, and a fluorescent image signal, which is the output from the fluorescent image processing apparatus 524, are selectively switched by the video switcher 526. A foot switch 527 for manually controlling switching of the image and a video switching controller 528 for automatically controlling switching of the image in accordance with the results of calculations performed by the fluorescent image processing apparatus are connected to the video switcher 526. A monitor 529 is connected to the output terminal of the video switcher 526 so that the fluorescent image signal or the normal image signal selected by the video switcher 526 is supplied to the monitor 529. Thus, the fluorescent image or the normal image is displayed on the monitor 529.

The fluorescent endoscope apparatus 500 comprises a fluorescent light distortion detection apparatus 530 for use when a correction quantity is set for the fluorescent image processing apparatus 524, the fluorescent endoscope apparatus 500 being connected to the fluorescent image processing apparatus 524. The fluorescent light distortion detection apparatus 530 has a distortion detection fluorescent plate (hereinafter called a "fluorescent plate") having fluorescent characteristics that are completely uniform two-dimensionally with respect to the irradiation with excitation light so that the fluorescent light distortion detection apparatus 530 detects the irradiation with the excitation light to transmits a control signal to the fluorescent image processing apparatus 524.

When observation is performed with the fluorescent endoscope apparatus 500 according to example, the timing controller 525 transmits a timing control signal to instruct the introduced-light switching apparatus 508 and camera switch unit 512 to switch the light source and the camera so that the fluorescent light observation or the normal observation is selected. At this time, the timing controller 525 synchronizes the process to be performed in the fluorescent image processing apparatus 524 with the operations of the movable mirror 509 of the introduced-light switching apparatus 508, the movable mirror 520 of the camera switch unit 512 and the rotative filter 516 of the fluorescent-light camera 514.

When normal light observation is performed, the movable mirrors 509 and 520 are moved to the position designated by a continuous line shown in FIG. 30. As a result, normal light is introduced from the normal observation light source apparatus 503 into the light guide 504 of the endoscope 501 through the introduced-light switching apparatus 508 so that the subject portion to be observed is irradiated with normal light. An image obtained from the irradiation of normal light emitted by the lamp 503a is allowed to pass through the image guide 505 and the camera switch unit 512 so as to be introduced into the normal-light camera 513 so that the image is photographed. A photography signal of the normal image captured by the CCD 515 is signal-processed by the CCU 523 so that it is, as an observed normal image signal, transmitted to the video switcher 526.

When the fluorescent light observation is performed, the movable mirrors 509 and 520 are moved to the position designated by the dashed line shown in FIG. 30. As a result, excitation light emitted by the fluorescent observation light source apparatus 502 is introduced into the light guide 504 of the endoscope 501 through the introduced-light switching apparatus 508 so that the subject portion to be observed is irradiated with excitation light. A fluorescent image obtained due to the irradiation with excitation light is allowed to pass through the image guide 505 and the camera switch unit 512 so as to be introduced into the fluorescent-light camera 514 so that the fluorescent image is photographed. In the fluorescent-light camera 514, the fluorescent components in the wavelength bands λ1 and λ2 are filtered by the rotative filter 516, and the fluorescent image is amplified by the I.I. 518 and the fluorescent image is captured by the CCD 519. The photography signal of the fluorescent image captured by the CCD 519 is signal-processed by the fluorescent image processing apparatus 524 and it is, as the observed fluorescent image signal, transmitted to the video switcher 526.

In this embodiment, the timing controller 525 performs switching between the normal light observation and the fluorescent light observation at high speed. As a result, both observed normal image signal and the observed fluorescent image signal are always transmitted to the video switcher 526.

As a method of displaying the observed normal image and the observed fluorescent image that have been received by the video switcher 526 on the monitor 529, the image is selectively switched in accordance with an instruction issued from the foot switch 528 to display either image. Another method may be employed in which the video switch controller 528 controls the switching of the image to display the fluorescent image in accordance with the results of the calculations performed by the fluorescent image processing apparatus 524 if a diseased portion, such as a cancer, is detected. Another method may be employed in which the video switcher 526 synthesizes the observed fluorescent image and the observed normal image to superimpose and display the two images or to synthesize the two images so as to be displayed.

FIG. 31 illustrates the detailed structure of the fluorescent image processing apparatus 524 to describe the structure and operation of the fluorescent image processing apparatus 524.

The fluorescent image processing apparatus 524 has a signal input portion that comprises a multiplexor 541. The multiplexor 541 transmits the supplied fluorescent image signal to a frame memory 542 for the wavelength λ1 and a frame memory 543 for the wavelength λ2 while switching the receiving portion in accordance with the fluorescent components in the wavelength band λ1 and λ2. That is, the frame memory (λ1) 542 and the frame memory (λ2) 543 store corresponding fluorescent image signals having wavelengths λ1 and λ2.

The multiplexor 541 receives the timing control signal supplied from the timing controller 525 so as to synchronize the timing of the fluorescent image signals having the wavelengths λ1 and λ2 with the switching timing of the multiplexor.

A switcher (λ1) 544 and a switcher (λ2) 545 for switching the portion for receiving the signals are disposed in the rear of the frame memory (λ1) 542 and the frame memory (λ2) 543. Fluorescent light distortion detection apparatus circuits 546 and 547 and image conversion tables 548 and 549 for the wavelengths λ1 and λ2 are connected to the corresponding switchers 544 and 545.

The fluorescent light distortion detection circuits 546 and 547 subject the standard signal level of the fluorescent image signal obtainable when the fluorescent light distortion detection apparatus 530 is irradiated with excitation light to a comparison with a predetermined value to detect the distortion of the fluorescent image. In accordance with the result of the detection, the fluorescent light distortion detection circuit 546 and 457 transmit correction-value setting signals to image conversion tables 548 and 549 so that the respective image conversion tables 548 and 549 for correcting the signal levels of the fluorescent image signals are made.

The output terminals of the image conversion tables 548 and 549 are connected to a calculating circuit 550 so that the fluorescent image signals corrected by the image conversion tables 548 and 549 are subjected to a predetermined calculation in the calculating circuit 550 so as to be transmitted as observed fluorescent images.

When the fluorescent light observation is performed, the texture of an organism is irradiated with violet light having a wavelength λ0=442 nm formed due to the irradiation with excitation light emitted by the fluorescent observation light source apparatus 502 so that spontaneous fluorescent light having a wavelength longer than 442 nm is generated. The thus-formed fluorescent images are, in the fluorescent-light camera 514, separated and filtered by the rotative filter 516 into two wavelength regions consisting of λ1=480 to 520 nm and λ2=630 nm or longer so that λ1 and λ2 fluorescent images are sequentially photographed. The sensitivity of fluorescent light in the visible region that can be obtained due to excitation light of ultraviolet light is intense in a normal portion but the same is weak in a diseased portion, such as a cancer. In particular, the sensitivity of fluorescent light having the wavelength λ1=480 to 520 nm is intense in a normal portion by a degree significantly different from the intensity in the diseased portion.

Accordingly, the calculating circuit 550 calculates, for example, the ratio or the difference between the intensities of fluorescent light having the wavelengths λ1 and λ2 to generate an observed fluorescent image signal with which the state of the texture of an organism can be distinguished.

In order to prevent deterioration in the S/N ratio due to weakening of the intensity of fluorescent light in the periphery of the observed fluorescent image, the fluorescent light distortion detection apparatus 530 is used to make the image conversion tables 548 and 549 of the fluorescent image processing apparatus 524 so as to set the correction quantity. Thus, the fluorescent image signal is corrected.

The operation to be performed when the image conversion tables 548 and 549 are made will now be described.

When the correction quantity of the fluorescent image signal is set, the fluorescent plate 531 of the fluorescent light distortion detection apparatus 530 is irradiated with excitation light emitted by the fluorescent observation light source apparatus 502. A fluorescent image signal obtained by photographing the fluorescent image of the fluorescent plate 531 by the fluorescent-light camera 514 through the endoscope 501 is transmitted to the fluorescent image processing apparatus 524. Since the fluorescent plate 531 has, in the wavelength of fluorescent light to be used, completely uniform fluorescent characteristics two-dimensionally with respect to the irradiation with excitation light, a fluorescent image, the fluorescent intensity of which is two-dimensionally constant, can be obtained. On the basis of the fluorescent image serving as a standard, the fluorescent image processing apparatus 524 makes the image conversion tables 548 and 549 that two-dimensionally convert the image signal in such a manner that the level of the fluorescent image signal is two-dimensionally constant.

When the fluorescent light distortion detection apparatus 530 detects the irradiation with excitation light, the fluorescent light distortion detection apparatus 530 supplies switcher control signals to the switchers 544 and 545 of the fluorescent image processing apparatus 524 to switch the switchers 544 and 545 to transmit the fluorescent image signals stored in the frame memories 542 and 543 to the fluorescent light distortion detection circuits 546 and 547. In accordance with the results of the detection performed by the fluorescent light distortion detection circuit 546 and 547, the image conversion tables 548 and 549 are made and stored. Thus, the correction quantity of each fluorescent image signal is set.

A specific example of algorithm for making the image conversion tables by the fluorescent light distortion detection circuits 546 and 547 will now be described. In order to simply draw the structure, FIG. 32 shows only 8×8 pixels.

Figure 32A:
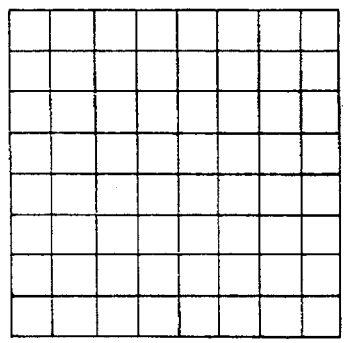
FIG. 32(a) illustrates an original image.
Figure 32B:
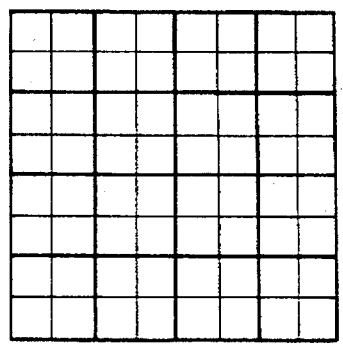
FIG. 32(b) illustrates an image in which 2×2 pixels have been made to be one unit.

Initially, first step is performed in such a manner that a fluorescent image obtained by photographing the fluorescent plate 531 irradiated with excitation light is subjected to the following process in which an original image shown in FIG. 32(a) is divided into first sub-blocks each of which is composed of 2×2 pixels as shown in FIG. 32(b).

Figure 32C:
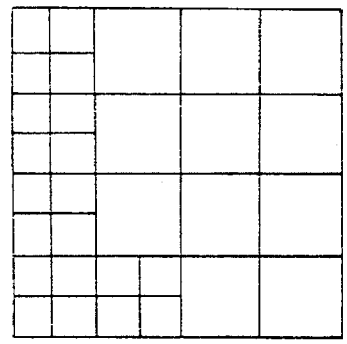
FIG. 32(c) illustrates an image in which unification to 2×2 pixels has been performed.

In second step, an accumulated value of brightness (accumulated value of signal intensities) of the fluorescent image signal in each first sub-block is obtained. The obtained value is compared with a predetermined threshold T1. If the value of the accumulated brightness is smaller than the threshold T1, four pixels (2×2) in the first sub-block are assumed to be one pixel as shown in FIG. 32(c). An accumulated value of the brightness obtained by accumulating the signal intensities of the four pixels in the sub-block is used as the brightness of the pixel. An operation of assuming the plurality of pixels in the divided sub-block to be one pixel and making the accumulated value of the brightness of the sub-block to be the brightness of the pixel is called pixel unification. As a result of the pixel unification, the signal level of the brightness of the pixels assumed to be the one pixel is about four times that of the original pixel.

That is, if a fluorescent image signal, which is obtained by photographing the standard fluorescent image, has a signal level (intensity of fluorescent light) which is the brightness of each pixel and which is lower than a predetermined level, an assumption is made that the intensity of fluorescent light of the pixel is too weak and distortion has been detected that causes the S/N ratio to deteriorate. Thus, the pixel unification in which a plurality of pixels are assumed to be one pixel is performed. In this example, the upper right portion of each section of FIG. 32 corresponds to the periphery, while the lower left portion corresponds to the pixel in the central portion. Since the pixel corresponding to the periphery has low brightness, the pixel unification is performed. FIG. 32(c) shows that 11 first sub-blocks are subjected to the pixel unification.

Figure 32D:
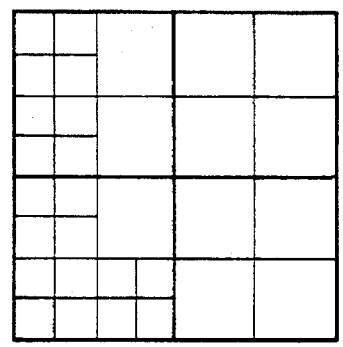
FIG. 32(d) illustrates an image in which 4×4 pixels have been made to be one unit.

In third step, the images subjected to the pixel unification as shown in FIG. 32(c) are divided into second sub-blocks each consisting of 4×4 pixels as shown in FIG. 32(d).

Figure 32E:
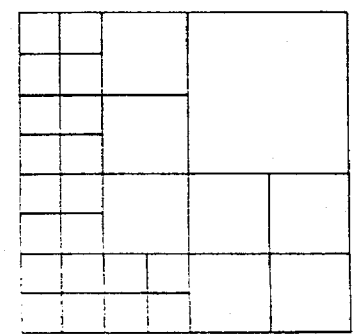
FIG. 32(e) illustrates an image in which unification to 4×4 pixels has been performed.

In fourth step, in only a case where all of four first sub-blocks in each second sub-block are assumed to be one pixel due to the pixel unification operation, the accumulated value of the brightness of the fluorescent image signals of the four pixels is obtained, the obtained value being then compared with a predetermined threshold T2. If the accumulated value of the brightness is less than the threshold T2, the four pixels (the first sub-block is composed of 2×2 pixels, that is, 4×4 pixels) in the second sub-block are assumed to be one pixel as shown in FIG. 32(e). Then, the signal unification is performed in which the accumulated value of the brightness obtained by accumulating the signal intensities in the foregoing sub-block is made to be the brightness of the pixel. FIG. 32(e) shows that the one second sub-block is subjected to the pixel unification.

In ensuing steps, pixel unification operations similar to the above are repeated such that third sub-blocks each consisting of 8×8 pixels are subjected to the same, fourth sub-blocks each consisting of 16×16 pixels are subjected similarly. When the process reaches a sub-block having a predetermined size or when no subject of the pixel unification is present, the foregoing pixel unification operation is completed.

As a result of the foregoing operation, the number of pixels to be unified is determined while monitoring the light intensity of each pixel in a case where the standard fluorescent image is actually photographed. The obtained state of pixel unification is the contents of the image conversion tables. In the example shown in FIG. 32, the state of unification shown in FIG. 32(e) is the image conversion table. The fluorescent light distortion detection circuits 546 and 547 subject the λ1 and λ2 fluorescent image signals to the pixel unification operations to make and store the image conversion tables 548 and 549.

When fluorescent observation and diagnosis are actually performed, the fluorescent image signals supplied to the fluorescent image processing apparatus 524 and stored in the frame memories 542 and 543 in the foregoing apparatus are directly supplied from the switchers 544 and 545 to the image conversion tables 548 and 549. When the fluorescent image signals are supplied to the image conversion tables 548 and 549, the pixel unification is immediately performed in the image conversion tables 548 and 549 so that the image signals are two-dimensionally converted. Thus, the brightness level at a predetermined position in each fluorescent image signal is corrected. The fluorescent image signals are corrected in the image conversion tables 548 and 549, and then they are subjected to a predetermined calculation in the calculating circuit 550. As a result, the fluorescent image signals are, as final observed fluorescent image signals, transmitted to the video switcher 526.

In accordance with the result of the calculation performed by the calculating circuit 550, a video switching control signal is, at this time, transmitted to the video switching controller 528. If a diseased portion, such as a cancer, is detected, the video switcher 526 can automatically be switched due to the control performed by the video controller 528 to display the fluorescent image.

Another method may be employed to make the image conversion tables in which the pixel unification is not limited to the division into the square sub-blocks but division into rectangular or oblong blocks. Another method may be employed in which the region division is performed in units of pixels as an alternative to the block units to determine the region for unifying pixels in an arbitrary shape to correspond to the state of the fluorescent image.

A portion of the standard fluorescent image obtained by photographing the fluorescent plate 531 and having a low signal level causes the signal level to be low in a case where a fluorescent image of a subject portion to be observed is photographed actually. Thus, the S/N ratio deteriorates. By subjecting the portion having unsatisfactory S/N ratio, such as the periphery of an image, to the pixel unification, that is, a spatial integration operation of image signals, the brightness of a dark portion having a low signal level can be raised and thus the S/N ratio can be improved. Namely, image signals having a constant signal level can be obtained in the overall portion of a standard fluorescent image by raising the signal level of the portion having a low fluorescent intensity. Thus, the brightness can be made to be uniform by the correction.

Although the spatial integration operation of the image signals deteriorates the resolution of the image by the degree corresponding to the integrating operation, the precise determination of the range of diseased portion is not so important for the fluorescent image diagnosis as compared with the importance of preventing missing of a diseased portion. Therefore, the structure of this example in which the image signals are subjected to the spatial integration operation causes an effect of preventing an error in the fluorescent diagnosis to be obtained by improving the SIN ratio of the fluorescent image as compared with a disadvantage that the accuracy of determining the diseased range deteriorates due to the deterioration in the resolution. As a result, the fluorescent diagnosing performance can significantly be improved when the fluorescent observation is performed so that an error in the fluorescent diagnosis is prevented.

An example structure of a fluorescent endoscope apparatus 500A having two excitation light source apparatuses to serve as the light source for the fluorescent diagnosis will now be described.

When fluorescent observation is performed, the following two methods have been mainly performed: a method according to the example shown in FIG. 30 and having an arrangement that the texture of an organism is irradiated with violet excitation light to observe an image of spontaneous fluorescent emitted by the texture; and a method in which a fluorescent substance, such as hematoporphyrin or photophyrin, having an integrating characteristic is injected into cancer textures of an organism and the cancer texture is irradiated with red excitation light having a wavelength of, for example, about 600 nm so that a fluorescent image emitting light having a wavelength longer than 600 nm is observed.

The fluorescent endoscope apparatus 500A according to this example comprises two fluorescent observation light source apparatuses to perform the two types of fluorescent observation operations.

The endoscope 501 has a structure similar to that according to the example shown in FIG. 30 such that a first introduced-light switching apparatus 561 for switching irradiating light between light of a lamp for performing the normal observation and excitation light for use to perform the fluorescent observation is connected to the connector disposed at the end of the universal cord 507 through which the light guide 504 is inserted. The normal observation light source apparatus 503 having the lamp 503a for emitting white normal light for the normal observation and a second introduced-light switching apparatus 562 for switching two types of excitation light beams are connected to the first introduced-light switching apparatus 561. A first fluorescent observation light source apparatus 565 having a first excitation laser 565a for emitting violet excitation light for observing spontaneous fluorescent light and a second fluorescent observation light source apparatus 566 having a second excitation laser 566a for emitting, for example, red, excitation light having a wavelength that excites the fluorescent substance are connected to the second introduced-light switching apparatus 562.

A camera switch unit and a camera (not shown) are connected to the ocular portion 506 of the endoscope 501 so as to photograph both normal image and a fluorescent image similarly to the example shown in FIG. 30.

The first introduced-light switching apparatus 561 and the second introduced-light switching apparatus 562 have corresponding movable mirrors 563 and 564. Thus, irradiating light to be supplied to the light guide 504 of the endoscope 501 can be switched.

When the normal endoscope observation is performed with the fluorescent endoscope apparatus 500A, the movable mirror 563 of the first introduced-light switching apparatus 561 is switched to the position designated by a continuous line shown in the drawing to introduce normal light emitted by the normal observation light source apparatus 503 into the light guide 504 of the endoscope 501. Thus, a normal image can be obtained.

When the fluorescent observation is performed, the movable mirror 563 of the first introduced-light switching apparatus 561 is switched to the position designated by a dashed line shown in the drawing. Thus, excitation light emitted by the first fluorescent observation light source apparatus 565 or the second fluorescent observation light source apparatus 566 is introduced into the light guide 504 of the endoscope 501 so that a fluorescent image is obtained.

Figure 33:
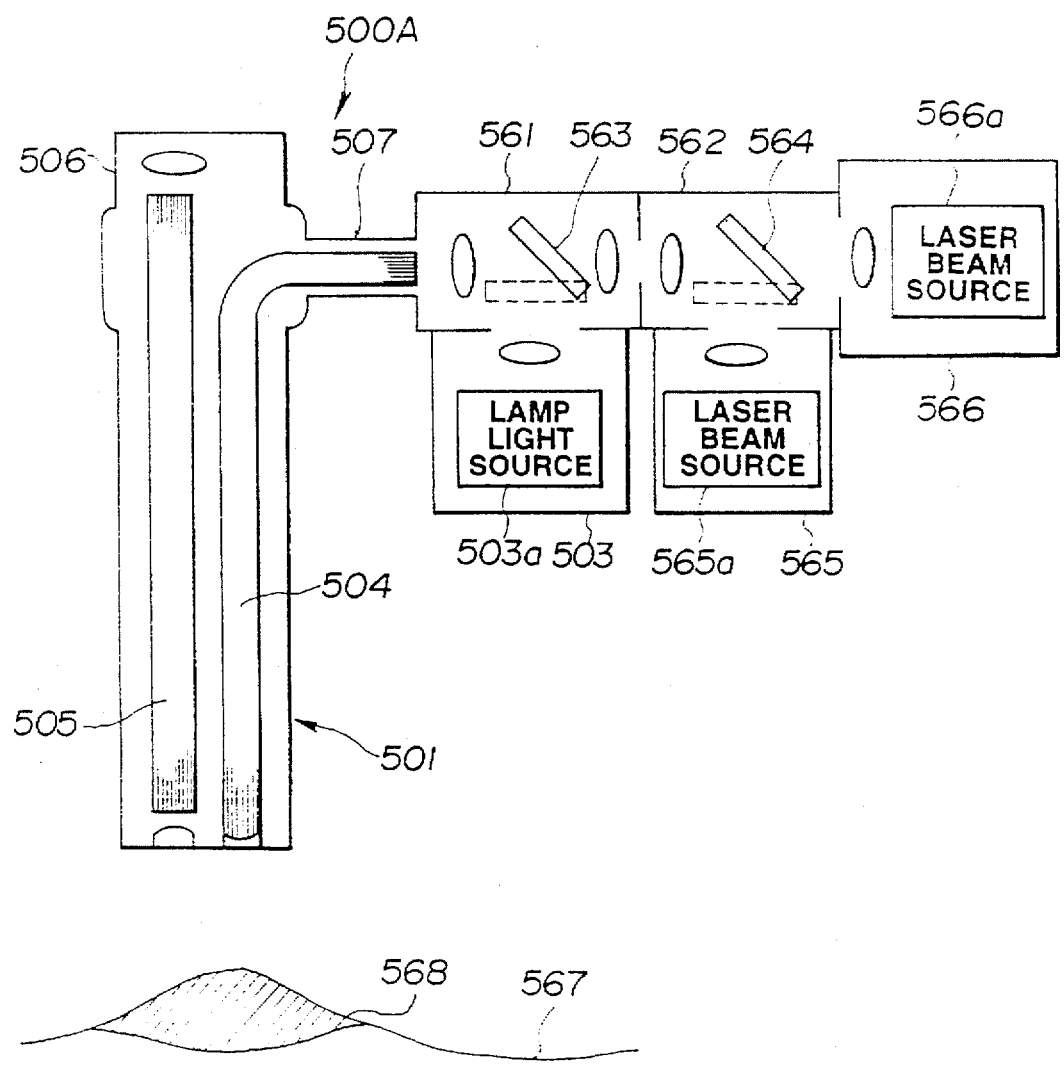
FIG. 33 illustrates a fluorescent endoscope apparatus having two fluorescent observation light source apparatuses.

In a case where the fluorescent substance is accumulated in a cancer or the like to observe a fluorescent image, the fluorescent substance is injected into a texture 567 of an organism in such a manner that the fluorescent substance is concentrically accumulated in a tumor portion 568. Then, the movable mirror 564 of the second introduced-light switching apparatus 562 is switched to the position designated by the dashed line shown in FIG. 33. Thus, excitation light for exciting the fluorescent substance that has been emitted by the fluorescent observation light source apparatus 566 is introduced into the endoscope 501 so that the texture 567 of the organism is irradiated with excitation light. As a result of this, the tumor portion 568 in the texture 567 of the organism has intense fluorescent light as compared with other portions. By observing the fluorescent image, a tumor, such as a cancer, can be determined.

As described above, according to this example, excitation light for the fluorescent observation using the spontaneous fluorescent light and excitation light for the fluorescent observation emitted by the fluorescent substance are switched to use as excitation light for the fluorescent observation, and the subject portion to be observed is irradiated with each excitation light so that the fluorescent observation by means of the fluorescent observation using spontaneous fluorescent light and that using the fluorescent substance are performed. Thus, the tumor portion can reliably be diagnosed.

Figure 34:
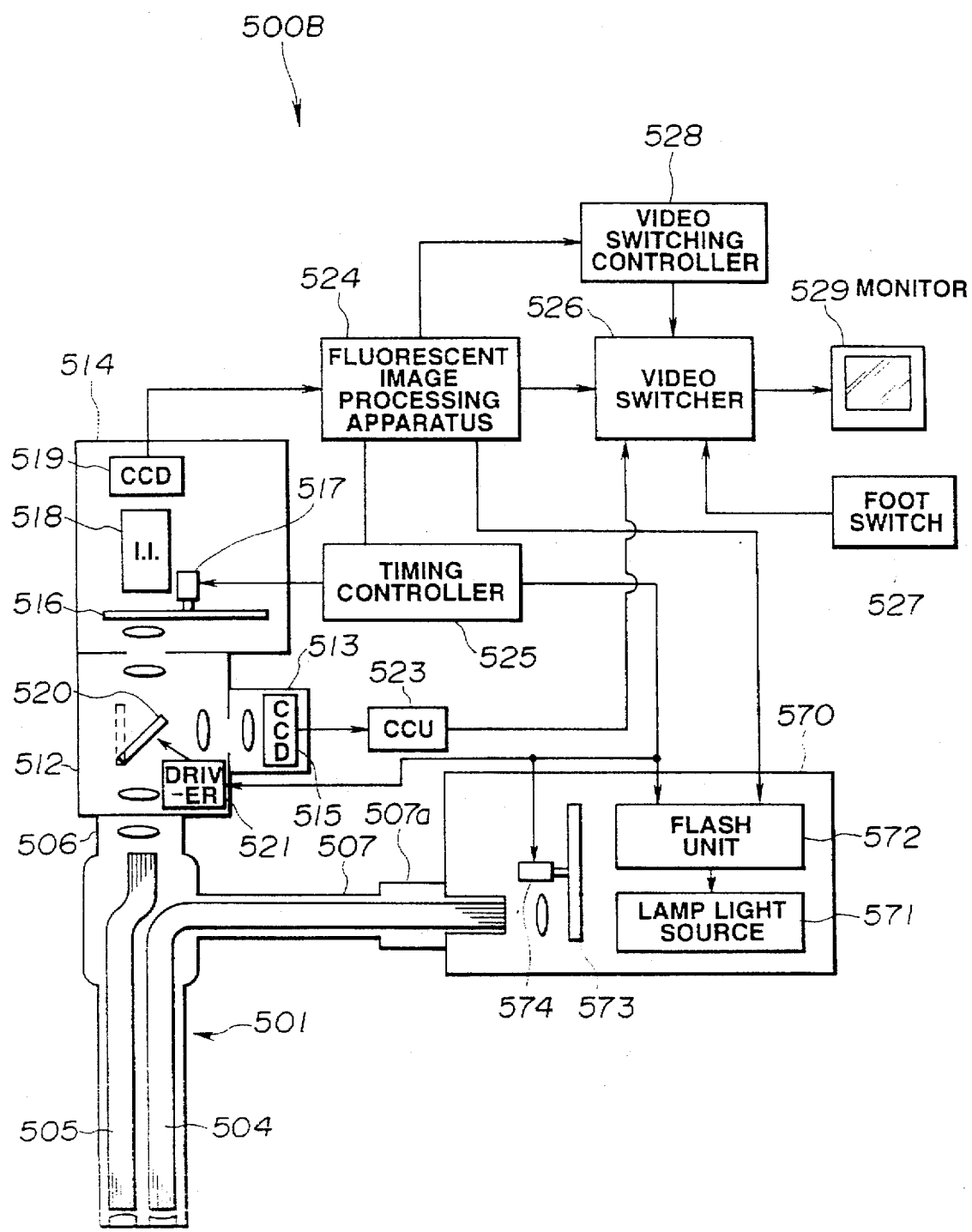
FIG. 34 illustrates a fluorescent endoscope apparatus capable of performing a normal endoscope observation and a fluorescent observation while necessitating one light source apparatus.

FIG. 34 illustrates an example of the structure of a fluorescent endoscope apparatus 500B which is capable of performing the normal endoscope observation and the fluorescent observation by one light source apparatus.

The light source apparatus 570 according to this embodiment is connected to the light guide connector 507a of the endoscope 501, the light source apparatus 570 having a lamp light source 571. A flash unit 572 is connected to the lamp light source 571 so that normal light for the normal observation and excitation light for the fluorescent observation can be generated. Furthermore, a rotative filter 573 for time-dividing normal light and excitation light is disposed in the optical path for light emitted by the lamp light source 571. The rotative filter 573 is rotated by a drive motor 574.

The flash unit 572 receives a flash control signal supplied from the fluorescent image processing apparatus 524 to control the flashing operation of the lamp light source 571 in order to temporarily enlarge the quantity of light to be emitted by the lamp light source 571. The operation timing of the flash unit 572 and that of the drive motor 574 are synchronized with each other in accordance with a timing control signal supplied from the timing controller 525

Light emitted by the lamp light source 571 is time-divided into normal light and excitation light by the rotative filter 573 so as to be alternately introduced into the light guide 504 of the endoscope 501 so that the subject portion to be observed is irradiated with light. At this time, the timing of the light source apparatus, which is the light emitting portion, and the timing of each of the adapter, camera and the signal processing apparatus which are light receiving units, are synchronized with one another under control performed in accordance with a timing control signal supplied from the timing controller 525.

The fluorescent image processing apparatus 524 monitors the signal level of the fluorescent image signal supplied from the camera to detect the brightness of the fluorescent image so as to supervise the intensity of excitation light. If the intensity of excitation light is unsatisfactory, the fluorescent image processing apparatus 524 transmits a flash control signal to the flash unit 572. At this time, the flash unit 572 causes the lamp light source 571 to emit flash light at adequate timing while receiving the timing control signal supplied from the timing controller 525.

By constituting the light source apparatus as described above, an excitation light emitting apparatus for generating excitation light for the fluorescent observation can be omitted from the structure. Thus, one light source apparatus is sufficient to obtain normal light for the normal observation and excitation light for the fluorescent observation so that both normal observation and the fluorescent observation can be performed. If the quantity of excitation light is unsatisfactorily small, the flashing operation of the lamp enables a sufficient light quantity to be obtained. As a result, the fluorescent observation can be performed satisfactorily.

Figure 35:
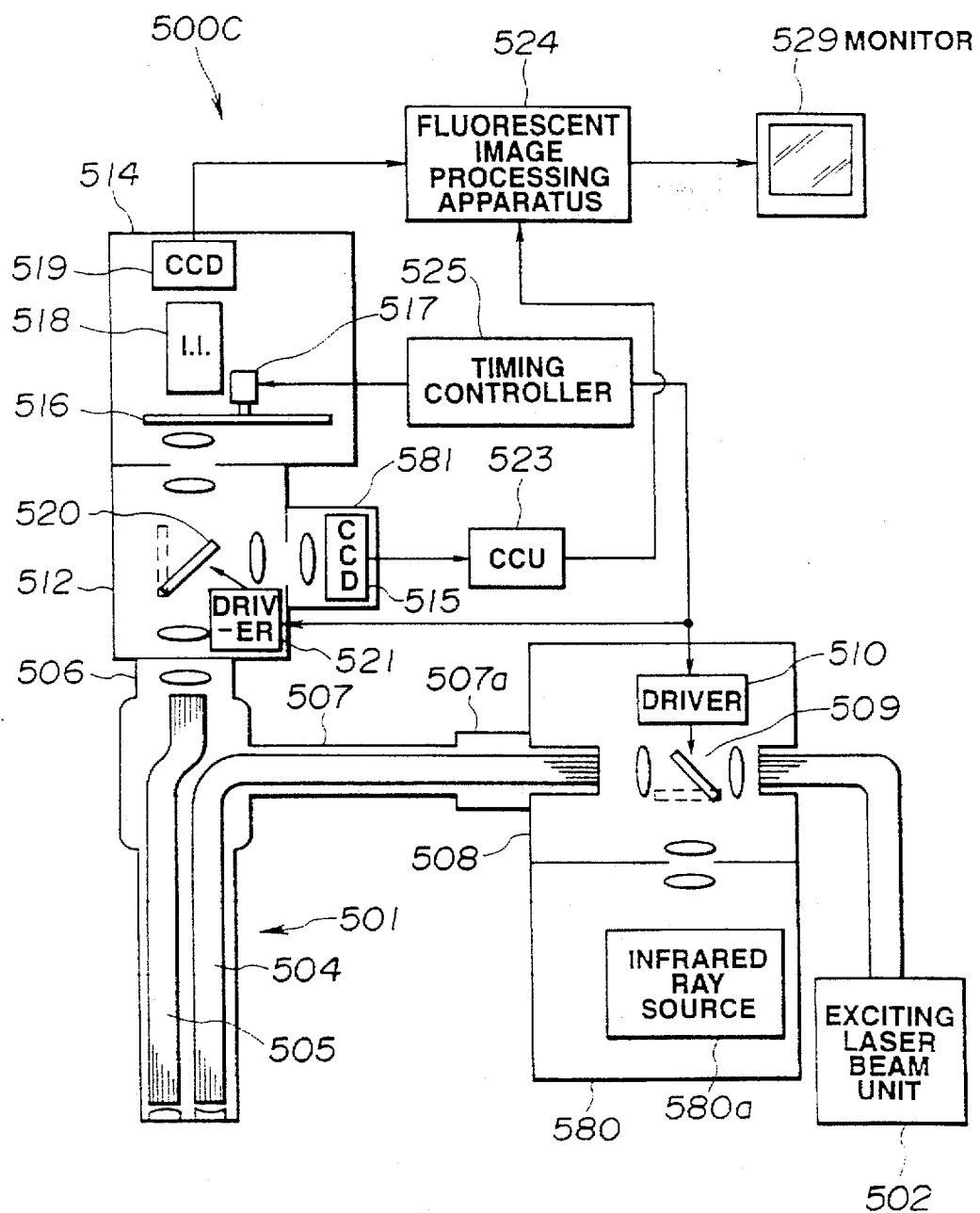
FIG. 35 illustrates a fluorescent endoscope apparatus having an infrared observation light source apparatus in place of the normal observation light source apparatus.

A fluorescent endoscope apparatus 500C is shown in FIG. 35 which uses an infrared-ray source apparatus to serve as a light source for emitting infrared image for correcting the fluorescent image.

The fluorescent endoscope apparatus 500C according to this embodiment comprises, in place of the normal observation light source apparatus 503 for supplying normal light for the normal observation, an infrared-ray source apparatus 580 for emitting infrared rays for obtaining infrared image. As an alternative to the normal-light camera 513, an infrared camera 581 can be attached to the camera switch unit 512. Infrared irradiating rays emitted by the infrared-ray source apparatus 580 are supplied to the endoscope 501 through the introduced-light switching apparatus 508.

The light guide 504 for introducing light emitted by the fluorescent observation light source apparatus 502 or the infrared-ray source apparatus 580 and an image guide 505 for transmitting the observed image to the ocular portion 506 disposed at the rear end are inserted into the endoscope 501. A light guide connector receiver 507a disposed at the end of the universal cord 507, through which the light guide 504 is inserted, is connected to the introduced-light switching apparatus 508.

The fluorescent-light camera 514 and the infrared camera 581 are connected to the camera switch unit 512 that is mounted on the ocular portion 506 of the endoscope 501. Thus, the infrared image and the fluorescent image can be photographed by the corresponding image sensing means. The fluorescent-light camera 514 is connected to the fluorescent image processing apparatus 524 so that an image signal of the fluorescent image photographed by the fluorescent-light camera 514 is supplied to the fluorescent image processing apparatus 524 so as to be signal-processed.

The infrared camera 581 is, through the CCU 523, connected to the fluorescent image processing apparatus 524 so that an image signal of the infrared image photographed by the infrared camera 581 is signal-processed by the CCU 523 so as to be supplied to the fluorescent image processing apparatus 524. In accordance with the infrared image signal, the fluorescent image signal is corrected so that a fluorescent image signal is generated. An output terminal of the fluorescent image processing apparatus 524 is connected to the monitor 529 so that a fluorescent image, which is the output from the fluorescent image processing apparatus 524, is displayed on the monitor 529. The other structures that are the same as those of the first embodiment shown in FIG. 30 are given the same reference numerals and their descriptions are omitted.

When a fluorescent image is observed with the fluorescent endoscope apparatus 500C, the timing controller 525 synchronizes the operation timing of each of the movable mirror 509 of the introduced-light switching apparatus 508, the movable mirror 520 of the camera switch unit 512 and the rotative filter 516 of the fluorescent-light camera 514 so that switching of the introduced-light switching apparatus 508 and the camera switch unit 512 is controlled. Thus, the light source and the camera are switched.

The introduced-light switching apparatus 508 switches excitation light emitted by the fluorescent observation light source apparatus 502 and infrared rays emitted by the infrared-ray source apparatus 580 to introduce selected light to the light guide 504 of the endoscope 501. Light introduced from the introduced-light switching apparatus 508 is allowed to pass through the light guide 504 to be transmitted to the leading end of the endoscope 501 so that the subject portion to be observed and positioned in front of the leading portion is irradiated with light. Light returned from the subject portion to be observed is, as a fluorescent image or an infrared image, transmitted to the ocular portion 506 adjacent to the operator through the image guide 505 that passes through the endoscope 501.

The camera switch unit 512 switches the camera for transmitting an image obtained at the ocular portion 506 of the endoscope 501 so that the fluorescent image is introduced into the fluorescent-light camera 514 and the infrared image is introduced into the infrared camera 581.

An image of an object (an infrared image) irradiated with infrared rays is captured by the CCD 515 included by the infrared camera 581 so that the thus-captured infrared image signal is transmitted to the CCU 523 so as to be signal-processed. As a result, the object image is, as an infrared image signal, transmitted to the fluorescent image processing apparatus 524.

The fluorescent image (the observed fluorescent image) obtained by irradiating the subject portion to be observed with excitation light is, by the rotative filter 516 of the fluorescent-light camera 514, subjected to an operation in which the fluorescent components in the two wavelength bands, in which the ratio of the normal portion and the diseased portion has different ratios of the intensities of fluorescent light, are filtered. Then, the light level of the fluorescent image is amplified by the image intensifier 518 so that the fluorescent image is captured by the CCD 519. A signal representing the captured fluorescent image is transmitted to the fluorescent image processing apparatus 524.

The fluorescent image processing apparatus 524 signal-processes the fluorescent image signal supplied from the fluorescent-light camera 514 to generate a fluorescent image signal with which the healthy portion and the diseased portion can be separated and distinguished from each other by the foregoing pseudo-color display method. Thus, a fluorescent image is displayed on the monitor 529.

The infrared image obtained due to the irradiation with the infrared rays emitted by the infrared-ray source apparatus 580 is formed into an image having a brightness level which is in proportion to the blood volume. Therefore, information indicating the quantity of blood volume in the subject portion to be observed can be obtained from the infrared image. Since the fluorescent image is considerably affected by the blood in the subject portion to be observed, the fluorescent diagnosis can sometimes be performed erroneously depending upon the blood volume. Accordingly, the fluorescent image processing apparatus 524 corrects the fluorescent image signal in accordance with the infrared image signal supplied from the CCU 523 such that, for example, the signal level is lowered/raised in accordance with the quantity of the blood volume. Thus, a fluorescent image, from which the influence of the difference in the blood volume in the subject portion to be observed is eliminated, can be formed.

As described above, this example is able to correct the influence occurring due to the difference in the blood volume in the subject portion to be observed and effecting on the fluorescent image. Therefore, the fluorescent diagnosis can be performed accurately without the influence of the blood volume.

Three examples of a fluorescent endoscope apparatus 600 with which a fluorescent image suitable to performing a diagnosis can be obtained will now be described with reference to FIGS. 36 to 43.

Hitherto, the fluorescent observation light source apparatus always emits excitation light in a predetermined quantity so that the subject portion to be observed is irradiated with excitation light. Therefore, fluorescent light in an adequate quantity cannot sometimes be obtained depending upon the state of the subject portion to be observed or the distance to the position of the same, thus resulting in that a satisfactory fluorescent image cannot sometimes be obtained. This example is intended to provide a fluorescent endoscope apparatus with which a fluorescent image suitable to perform a diagnosis can be obtained regardless of the distance from the light emission terminal for excitation light to the subject portion to be observed.

Figure 36A:
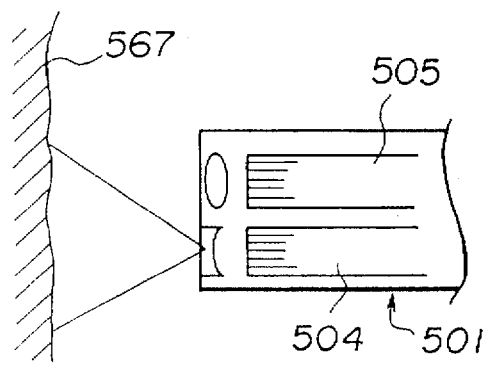
FIG. 36(a) illustrates an excellent positional relationship between an excitation light emission terminal and a subject portion to be observed when the fluorescent light observation is performed.

In general, FIG. 36(a) shows a case where the positional relationship between the light emission terminal for excitation light and the subject portion to be observed is adequate. In this case, the intensity of fluorescent light is as shown in FIG. 36(c) such that a normal portion has a characteristic as designated by a continuous line and a diseased portion has a characteristic as designated by a dashed line having alternating long and two short dashes. At this time, excitation light is, as shown in FIG. 36(a), introduced through the light guide 504 included in the endoscope 501 so as to be emitted through the leading surface of the light guide 504 toward a subject portion 567 to be observed. Fluorescent light emitted by textures in the subject portion 567 to be observed, which has been excited by excitation light, is imaged on the leading surface of the image guide 505.

Figure 36B:
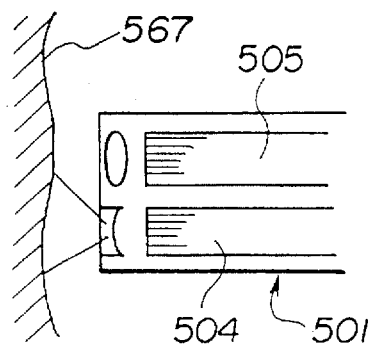
FIG. 36(b) illustrates an adverse positional relationship between the excitation light emission terminal and the subject portion to be observed when the fluorescent light observation is performed.
Figure 36C:
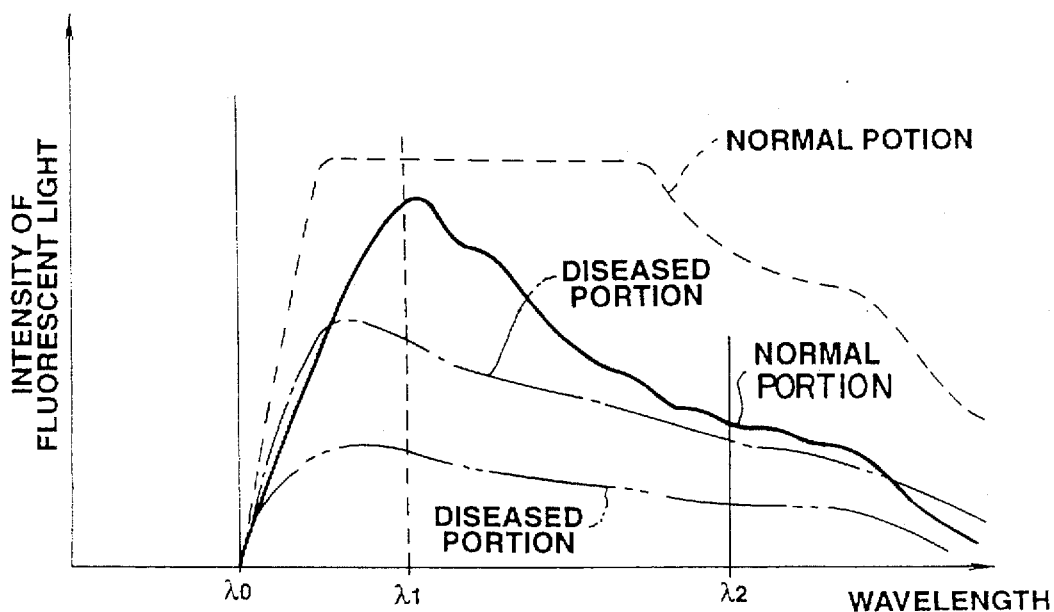
FIG. 36(c) illustrates the intensity of fluorescent light realized in the cases shown in FIGS. 36(a) and 36(b)

If the light emission terminal for excitation light and the subject portion to be observed approach excessively closely as shown in FIG. 36(b), the healthy portion has the characteristic as designated by a dashed line and the diseased portion has the characteristics as designated by a dashed line having alternate long and short dashes as shown in FIG. 36(c). As can be understood from this, a portion of the intensity of fluorescent light saturates, thus raising the possibility of an erroneous diagnosis. That is, if the intensity of fluorescent light is saturated, the intensity of fluorescent light at the wavelength of $\lambda 1$ is relatively weakened due to the saturation. Thus, the difference from the intensity of fluorescent light at the wavelength $\lambda 2$ is undesirably reduced. Therefore, diagnosis as either "healthy" or "diseased" performed in accordance with the ratio raises a risk of an erroneous diagnosis as "diseased".

Figure 37:
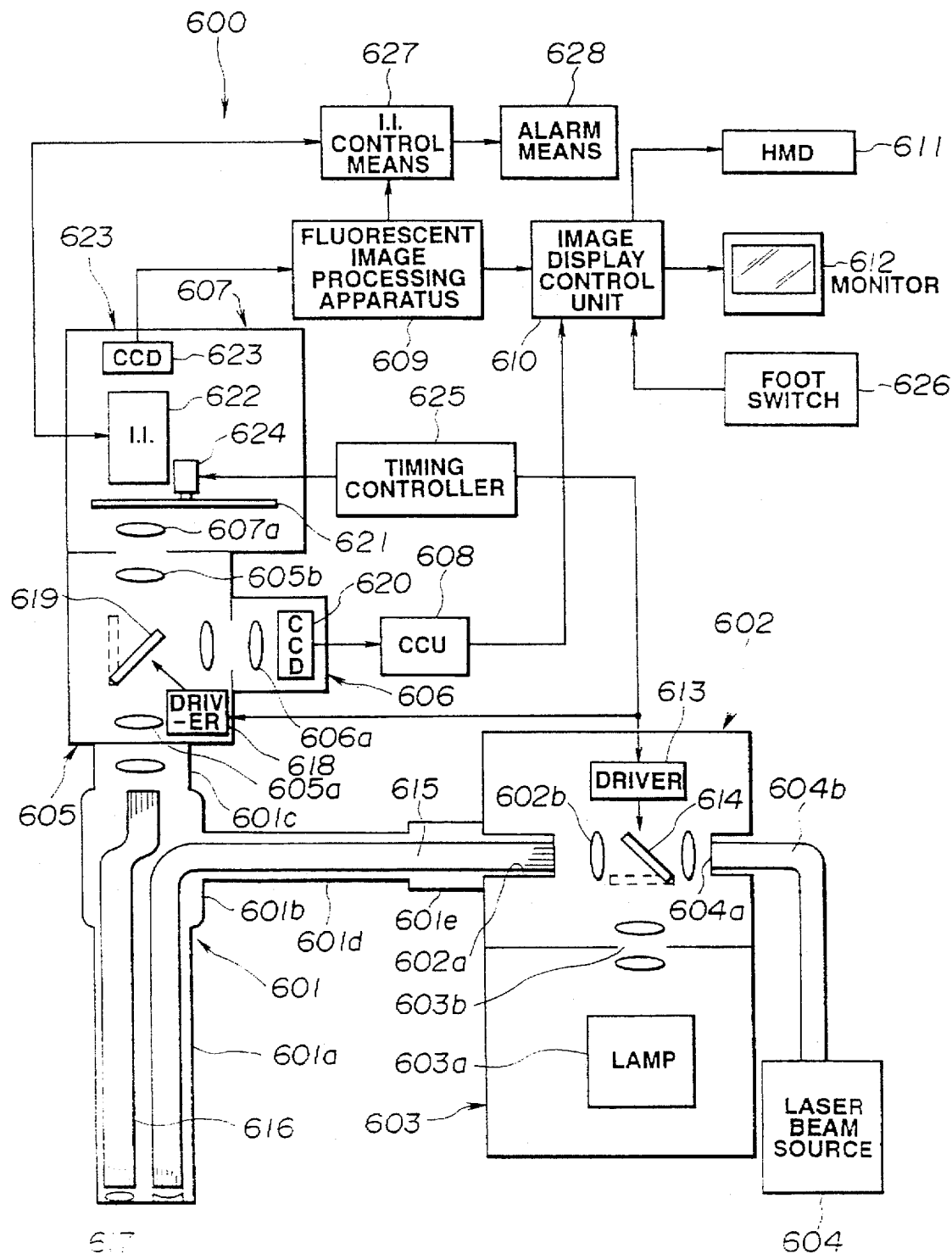
FIG. 37 illustrates the structure of a fluorescent endoscope apparatus capable of satisfactorily performing the fluorescent light observation regardless of the positions of the endoscope and the subject portion to be observed.

Accordingly, the fluorescent endoscope apparatus 600 according to this embodiment, as shown in FIG. 37, comprises: an endoscope 601; a normal observation light source apparatus 603 for supplying normal light to the endoscope 601 through an introduced-light switching apparatus 602; a fluorescent observation light source apparatus 604 for supplying excitation light; a normal-light camera 606 for photographing, through a camera switch unit 605, a normal image obtained by the endoscope 601; a fluorescent-light camera 607 for photographing, through the camera switch unit 605, a fluorescent image obtained by the endoscope 601; a CCU 608 for forming the photography signal of the image photographed by the normal-light camera 606 into a normal image signal; a fluorescent image processing apparatus 609 for forming the photography signal of the image photographed by the fluorescent-light camera 607 into a fluorescent image signal; an image display control unit 610 that receives signals supplied by the CCU 608 and the fluorescent image processing apparatus 609 to control image display; a head mount display (hereinafter abbreviated to a "HMD") 611 and a monitor 612 on which a normal image and a fluorescent image are displayed by the image display control unit 610; a foot switch 626 for performing an operation of controlling the image display control unit 610; an I.I. control means 627 for controlling the light amplification gain of an image intensifier (hereinafter abbreviated to an "I.I.") 622 in the fluorescent-light camera 607 in response to an output signal from the fluorescent image processing apparatus 609; and an alarm means 628 for issuing an alarm depending upon the state of output from the I.I. control means 627.

The endoscope 601 has an elongated insertion portion 601a serving as a probe that can be inserted into the body cavity or the like, a control portion 601b provided for the insertion portion 601a at a position adjacent to the hand of an operator, an ocular portion 601c disposed at the rear end of the control portion 601b and a light guide cable 601 d outwardly extending from the control portion 601b.

A light guide 615 comprising a flexible fiber bundle for transmitting light is inserted into the insertion portion 601a. A light guide connector 601e at an end of the light guide cable 601d adjacent to the hand of the operator is attachably/detachably connected to a light emission portion 602a of the introduced-light switching apparatus 602. A light emission portion 603b of the normal observation light source apparatus 603 and a light emission portion 604a of the fluorescent observation light source apparatus 604 are attachably/detachably connected to corresponding first and second light receiving portions of the introduced-light switching apparatus 602.

In the introduced-light switching apparatus 602, the driver 613 operates the movable mirror 614 so that switching between normal light emitted by the lamp 603a of the normal observation light source apparatus 603 and excitation light emitted by the fluorescent observation light source apparatus 604 is performed so as to be introduced into the light guide 615 of the endoscope 601.

In a case where the movable mirror 614 is disposed at a position designated by a continuous line shown in FIG. 37, normal light emitted by the lamp 603a is allowed to pass through a lens adjacent to the light emission portion 603b, is reflected by the movable mirror 614 and is then allowed to pass through a lens 602b adjacent to the light emission portion 602a so as to be introduced into the light guide 615. At this time, excitation light emitted by the fluorescent observation light source apparatus 604 is shielded by the movable mirror 614.

When the movable mirror 614 is disposed at the position designated by the dashed line, excitation light emitted by the fluorescent observation light source apparatus 604 is allowed to pass through a light conductive member 604b such as a fiber, and introduced into the introduced-light switching apparatus 602 through the second light receiving portion. Thus, the excitation light is introduced into the light guide 615 through the lens 602b in such a manner that it is not shielded by the movable mirror 614. At this time, normal light emitted by the lamp 603a is shielded by the movable mirror 614.

The light guide 615 irradiates the subject portion to be observed with light which has passed through the introduced-light switching apparatus 602. An image obtained due to the irradiation of the subject portion to be observed with light is formed on the leading surface of the image guide 616 in the insertion portion 601a and is transmitted through the image guide 616 until it reaches the ocular portion 601c.

The camera switch unit 605 is attachably/detachably connected to the ocular portion 601c. The camera switch unit 605 causes the driver 618 to operate the movable mirror 619 to introduce the normal image and the fluorescent image, which have been transmitted through the image guide 616, into the normal-light camera 606 when the movable mirror 619 is disposed at the position designated by the continuous line and into the fluorescent-light camera 607 when the movable mirror 619 is disposed at the position designated by the dashed line. The movable mirrors 614 and 619 are synchronously operated by the drivers 613 and 618 such that, when either of them is disposed at the position designated by the continuous line the residual one is disposed at the position designated by the continuous line. If either of the movable mirrors 614 and 619 is disposed at the position designated by the dashed line, the residual one is disposed to the position designated by the dashed line.

If the movable mirrors 614 and 619 are disposed at the positions designated by the continuous line, light reflected by the subject portion to be observed that is irradiated with normal light is allowed to pass through an observation optical system (that is, an objective lens 617, an image guide 616 and an ocular lens) of the endoscope 601, and is introduced into the camera switch unit 605.

Then, light is allowed to pass through a lens 605a facing the ocular lens, the movable mirror 619, a lens disposed on the optical path changed by the movable mirror 619, and a lens 606a in the normal-light camera 606 so that a normal image is formed on a CCD 620. A photographic signal of the normal image captured by the CCD 620 included in the normal-light camera 606 is transmitted to the CCU 608.

If the movable mirrors 614 and 619 are disposed at positions each of which is designated by the dashed line, excitation light emitted by the fluorescent observation light source apparatus 604 is transmitted through the light guide 615. Thus, the subject portion to be observed is irradiated with excitation light to excite fluorescent light which is then transmitted through the image guide 616 in the endoscope 601 so as to be introduced into the camera switch unit 605.

The introduced fluorescent image is allowed to pass through the lens 605a, a lens 605b facing the lens 605a, a lens 607a disposed on an optical path in the fluorescent-light camera 607 at a position facing the lens 605b and a rotative filter 621. Then, the fluorescent image is optically amplified by the I.I. 622 which enables sensitive photography to be performed before it is captured by the CCD 623. The fluorescent image captured by the CCD 623 is transmitted to the fluorescent image processing apparatus 609.

FIG. 36(c) shows the fluorescent characteristics when a subject portion to be observed is irradiated with excitation light. Fluorescent light of a texture obtainable due to irradiation with excitation light having a wavelength of 442 nm is intense in a healthy portion and is weak in a diseased portion in a short wavelength region thereof as compared with the intensity of the healthy portion. That is, the ratio of the intensities of fluorescent light having the wavelengths $\lambda 1$ and $\lambda 2$ becomes different between a healthy portion and a diseased portion. Therefore, the ratio of the image portions having the wavelengths $\lambda 1$ and $\lambda 2$ is obtained to distinguish "diseased" and "healthy". Therefore, the two band-pass filters provided for the rotative filter 621 are used to separate the $\lambda 1$ and $\lambda 2$ fluorescent images so as to be captured by the CCD 623.

Referring to FIG. 37, the movable mirrors 614 and 619 are synchronized by the timing controller 625 and operated by the drivers 613 and 618. The timing rotation of a motor 624 for rotating the rotative filter 621 is also controlled by the timing controller 625.

The image display control unit 610 is, as well as by the foot switch 626, able to perform switching between a normal image and a fluorescent image to be displayed on the monitor 612 and the HMD 611 which is fitted to the head of an operator and which serves as a display unit of a type fitted to an operator.

The HMD 611 comprises a light crystal display device and also having a see-through function. That is, the display device permits light transmission. Therefore, the operator is able to observe the normal image or the fluorescent image on the display in front of the eyes and also able to look a portion which is being operated, for example, adjacent to the hand of the operator when the operator looks the portion (that is, the operator sees through the liquid crystal display device).

The operation of the fluorescent endoscope apparatus 600 will now be described.

The I.I. control means 627 receives the signal having the wavelength of $\lambda 1$, the fluorescent intensity of which is intense, from the fluorescent image processing apparatus 609. Then, a limit value, which is somewhat weaker than a predetermined saturated intensity, and the fluorescent intensity of the light having the wavelength of $\lambda 1$ and $\lambda 2$ are subjected to a comparison. If the difference is too large, the I.I. control means 627 transmits control voltage to enlarge the gain of the I.I. control means 627 to reduce the difference.

That is, the output from the I.I. control means 627 is used to control the control voltage that controls the gain of the I.I. 622. Thus, a result as if the waveform of an output signal from the CCD 623 is subjected to AGC can be obtained. Thus, a high waveform level can be realized while preventing saturation of the characteristics of the intensity of fluorescent light.

By directly detecting the intensity of fluorescent light and by obtaining intense fluorescent light without the saturation as described above, an accurate ratio of the intensities of the fluorescent light having wavelengths $\lambda 1$ and $\lambda 2$ can always be obtained. By displaying the fluorescent image (in a pseudo color display manner) of the subject portion to be observed and the normal image on the monitor 612 in accordance with the ratio of the intensities of fluorescent light having the wavelengths $\lambda 1$ and $\lambda 2$, a discrimination can be performed as to whether the subject portion to be observed is healthy or diseased.

As an alternative to this, the fluorescent image may be displayed for the right eye of the operator and the normal image may be displayed for the left eye. The fluorescent image and the normal image may be superimposed so as to be displayed on the HMD 611.

Although the gain of the I.I. 622 is, in this example, controlled in accordance with the intensity of the fluorescent light having the wavelength $\lambda 1$, another method may be performed in which a peak value of the intensity of fluorescent light is detected and the gain of the I.I. 622 is controlled in such a manner that the peak value does not exceed the limit value.

An average value of the fluorescent intensities may be used. When the wavelength $\lambda 1$ is used, it may be in a narrow spectrum or in a certain band. As an alternative to control the gain of the I.I. 622, a diaphragm mechanism may be disposed in front of the I.I. 622 so that the intensity of fluorescent light that passes through the diaphragm is controlled by the diaphragm effect of the diaphragm mechanism.

If the fluorescent intensity is less than a predetermined level in a case where the gain of the I.I. 622 has been increased to a maximum value, a diagnosis with the signal level raises a possibility of an erroneous determination or an unreliable determination. In the foregoing case, the alarm means 628 or a notification means is activated to notify this fact to the operator. Thus, the operator brings the emission terminal to approach the subject portion to be observed when the fluorescent image is obtained. As a result, the S/N ratio can be increased and a fluorescent image can be obtained with which a discrimination whether the subject portion to be observed is a diseased portion or a healthy portion can be performed.

If the fluorescent intensity does not partially reach a predetermined level, this fact may be informed by the alarm means 628. If a range irradiated with excitation light is only a portion of the range observed by the observation system in a case where the distance is set to a distance less than that set in the case shown in FIG. 36(b), the detected fluorescent image partially has a high fluorescent intensity. However, the residual region includes a portion in which substantially no fluorescent intensity can be detected.

The foregoing state can be discriminated or identified by examining the distribution of fluorescent intensities in the periphery of the fluorescent image obtained by, for example, the CCD 623 with respect to an output signal from the CCD 623 (by the fluorescent image processing apparatus 609). Also in this case, the alarm means 628 may be used to issue an alarm (for example, a fact that only a portion of the fluorescent image can be observed or that the distance must be lengthened).

As the alarm means, any of feedback by means of, for example, sound (buzzer permitted), turning of a lamp, vibrations of the control portion, display on the monitor 612 and the like may be employed.

The HMD 611 may have a line-of-sight detection means to perform switching between the fluorescent image and the normal image by changing the line of sight at the time of observation.

The fluorescent endoscope apparatus 600 enables the following effects to be obtained.

By directly detecting the fluorescent intensity to control the gain of the I.I. 622, an optimum ratio of fluorescent intensities can always be obtained and an accurate diagnosis can be performed regardless of the state of the subject portion to be observed. If an image is observed by enlarging the magnification, for example, as shown in FIG. 36(b), control is performed in such a manner that the gain of the I.I. 622 is reduced to prevent saturation. Therefore, an accurate diagnosis can be performed.

By performing the control with the wavelength $\lambda 1$ for obtaining the ratio, the saturation of the obtained ratio can assuredly be prevented. Furthermore, an excellent fluorescent image can be obtained without deterioration in the S/N ratio.

Since the image is displayed on the HMD 611, the fluorescent image and the normal image can always be observed even if the operator changes the attitude thereof. Thus, the probability of missing a diseased portion can be reduced.

If a plurality of HMDs 611 are provided, a plurality of operators are enabled to obtain an excellent image, if necessary. That is, all operators are always able to obtain an excellent image regardless of the attitudes or positions even if they are changed.

In a case where assistant operators are present, installation of the HMD 611 to each assistant enables all operators and assistants to always observe an excellent image.

By using the see-through function of the HMD 611, the endoscope and the curing tool can easily be handled and thus the number of operators can be reduced.

Another structure may be employed in which a wireless video signal transmitting portion is provided for the output portion of the image display control unit 610. Furthermore, a video signal receiving portion, a video signal reproducing circuit and a power source are provided for the HMD 611 to enable the person who has the HMD 611 to observe the normal image or the fluorescent image in a wireless manner.

Since the necessity of connecting the image display control unit 610 and the cord to each other can be eliminated in the foregoing case, the operationality or the working efficiency can be improved.

Although omitted in FIG. 37, a channel, through which a curing tool can be inserted, may be formed in the endoscope 601 to enable a curing operation or the like to be performed by using the curing tool allowed to pass through the channel.

Figure 38:
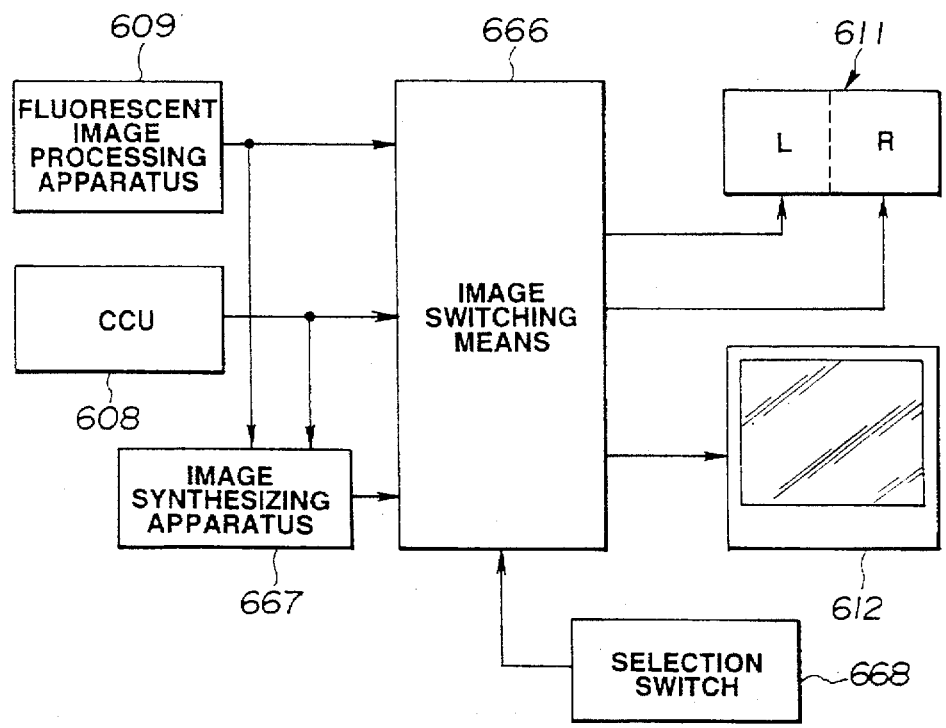
FIG. 38 illustrates a modification of FIG. 37.

Referring to FIG. 38, the structure of an image display control system according to a modification of the foregoing embodiment will now be described.

As shown in FIG. 38, output signals from the CCU 608 and the fluorescent image processing apparatus 609 are supplied to an image switching means 666 and an image synthesizing apparatus 667. The image synthesizing apparatus 667, for example, superimposes the supplied two signals to form one synthesized image to transmit this to the image switching means 666.

A selection switch 668 is connected to the image switching means 666 so that the operation of the selection switch 668 enables the image to be transmitted to the image display means to be switched or a display mode to be selected and set. The other structures are the same as those shown in FIG. 37.

In this modification, the operation of the selection switch 668 enables an output to be made such that, for example, the right-eye portion of the HMD 611 displays the fluorescent image and the left-eye portion displays the normal image. An output image from the image synthesizing apparatus 667 may be transmitted to the HMD 611. A switching control to transmit the normal image or the fluorescent image to the monitor 612 may be performed. The other operations and effects are the same as those shown in FIG. 37.

Figure 39:
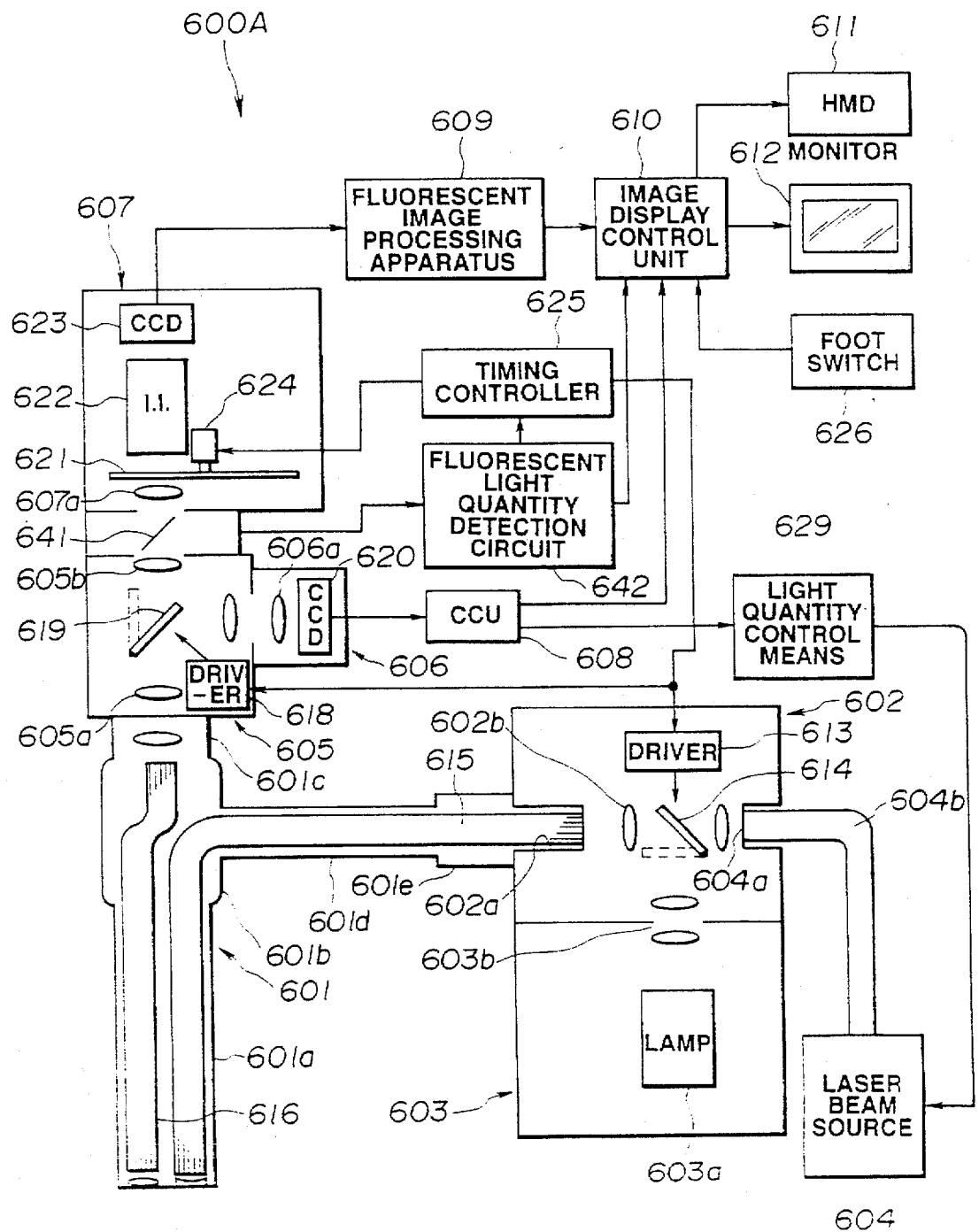
FIG. 39 illustrates another structure of FIG. 37.
Figure 41:
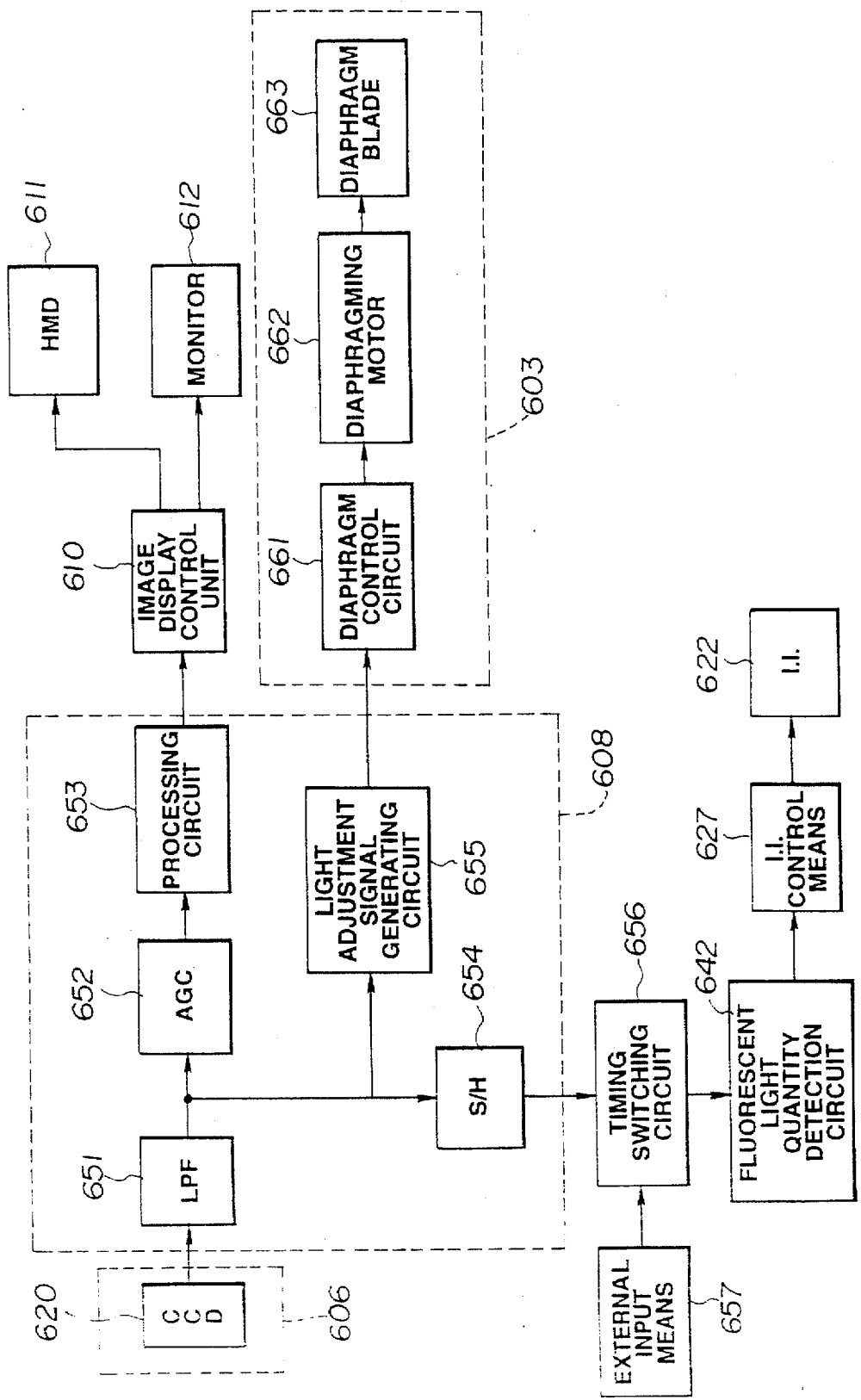
FIG. 41 illustrates a fluorescent endoscope apparatus having an input means for instructing a subject portion to be observed.

Referring to FIG. 39, another modification of the fluorescent endoscope apparatus 600 will now be described which is capable of obtaining an excellent fluorescent image suitable for a diagnosis.

As shown in FIG. 39, a fluorescent endoscope apparatus 600A is different from the fluorescent endoscope apparatus shown in FIG. 37 in that a beam splitter 641 for separating a fluorescent image is disposed between the camera switch unit 605 and the fluorescent-light camera 607 (for example, between the lens 605b and the lens 607a). The structure is arranged such that a portion of the fluorescent light quantity of a fluorescent image separated by the beam splitter 641 is detected by a fluorescent light quantity detection apparatus 642 so that the image display control unit 610 controls the displayed image in accordance with the detected quantity of fluorescent light.

Figure 40:
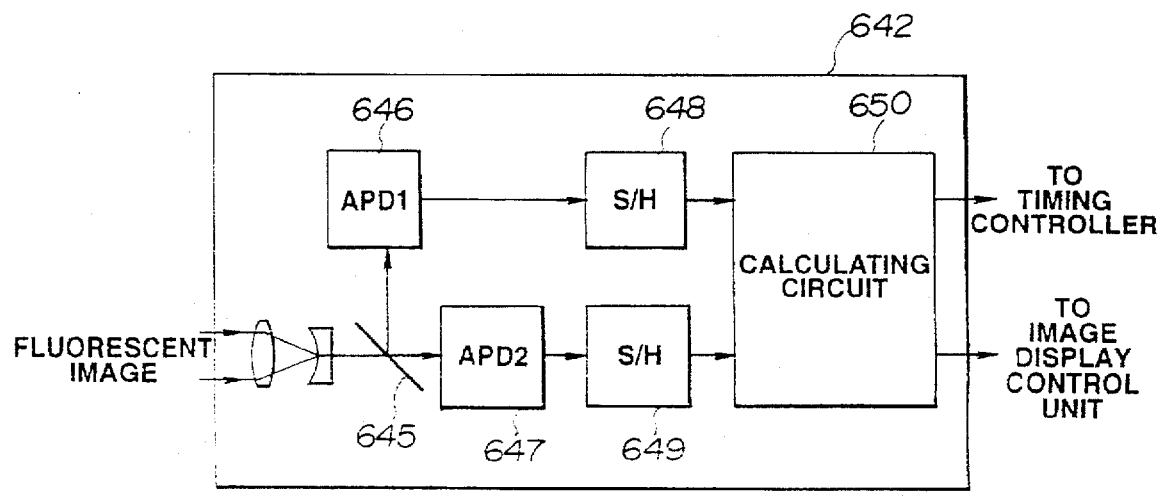
FIG. 40 is a block diagram which illustrates a fluorescent light quantity detection apparatus.

The fluorescent light quantity detection apparatus 642, as shown in FIG. 40, causes a dichroic mirror 645 to divide a fluorescent image into two wavelengths λ1 and λ2. Then, the quantities of fluorescent light beams having the wavelengths λ1 and λ2 are supplied to sensitive photodiodes (APD) 646 and 647 and are sampled in sample holding circuits (S/H) 648 and 649. The quantities of sampled fluorescent light having the wavelengths λ1 and λ2 are calculated by a calculating circuit 650 to determine whether or not the fluorescent light quantity indicates a diseased portion. Thus, the timing controller 625 and the image display control unit 610 are controlled.

If the fluorescent light quantity indicating a diseased portion is not detected, the fluorescent light quantity detection apparatus 642 controls the timing controller 625 to lengthen the time in which normal light is emitted by the normal observation light source apparatus 603 and shorten the time in which excitation light is emitted by the fluorescent observation light source apparatus 604. As a result, an observed image having sufficient brightness can be obtained if a diseased portion is not present. Thus, the operation for inserting the endoscope 601 and the like can be facilitated.

If a quantity of fluorescent light that indicates a diseased portion has been detected, the timing controller 625 shortens the time in which normal light is emitted by the normal observation light source apparatus 603 and lengthens the time in which excitation light is emitted by the fluorescent observation light source apparatus 604. As a result, a fluorescent image having sufficient brightness can be obtained if a diseased portion is present. Thus, a diagnosis of a diseased portion and the like can be easily performed.

Furthermore, this example has an arrangement in which a normal image signal supplied from the CCU 608 is supplied to the light-quantity control means 629 to control the intensity of excitation light emitted by the fluorescent observation light source apparatus 604. The light-quantity control means 629 extracts a brightness signal from the normal image signal to control excitation light in accordance with the level of the brightness signal. By utilizing a fact the distance from a subject portion to be observed and the state of the same can be estimated in accordance with the level of the brightness signal of the normal image, the intensity of fluorescent light is controlled to an adequate range.

A portion, from which a normal image signal having a level that is included in a desired range can be obtained, may be detected to control excitation light in accordance with the intensity of fluorescent light emitted by the portion.

An input means for instructing a subject portion to be observed, light from which is adjusted, may be provided. An example of a fluorescent endoscope apparatus having the input means will now be described with reference to FIG. 41.

An output signal from the CCD 620 included in the normal-light camera 606 is subjected to a process of removing the clock component thereof. Then, the output signal is allowed to pass through a low pass filter (hereinafter abbreviated to an "LPF") 651 and is integrated. The signal allowed to pass through the LPF 651 is processed in an AGC circuit 652 and a processing circuit 653 so as to be formed into an NTSC signal. Then, the NTSC signal is, by the image display control unit 610, displayed on a desired display means (for example, the monitor 612 or the HMD 611).

On the other hand, an output from the LPF 651 is supplied to a light adjustment signal generating circuit 655 so that drive voltage for a diaphragming motor 662 is generated by a diaphragm control circuit 661 of the normal observation light source apparatus 603 to control a diaphragm blade 663. Thus, the quantity of normal light is controlled.

In this example, the quantity of fluorescent light is controlled in accordance with the level of the brightness signal of a specific portion in place of average light measurement over one screen. An output from the LPF 651 is, at the timing that corresponds to the specific portion, sample-held by a sample holding circuit (hereinafter abbreviated to an "S/H") 654. If the output level at this time is higher than a predetermined level, the fluorescent light quantity detection apparatus 642 is operated at the same timing to control the gain of the I.I. control means 627. Thus, adequate normal and fluorescent images can be obtained. If the output from the S/H 654 is smaller than the predetermined value, the timing is switched to obtain an adequate fluorescent image.

In a case where a fluorescent image in a region of interest for an operator is intended to be observed under further satisfactory conditions, the timing may be set by an external input means 657.

This example has an effect that the normal image and the fluorescent image can always be observed in a satisfactory state.

An applicable example, with which a fluorescent image suitable for a diagnosis can be obtained regardless of the distance, will now be described.

Figure 42:
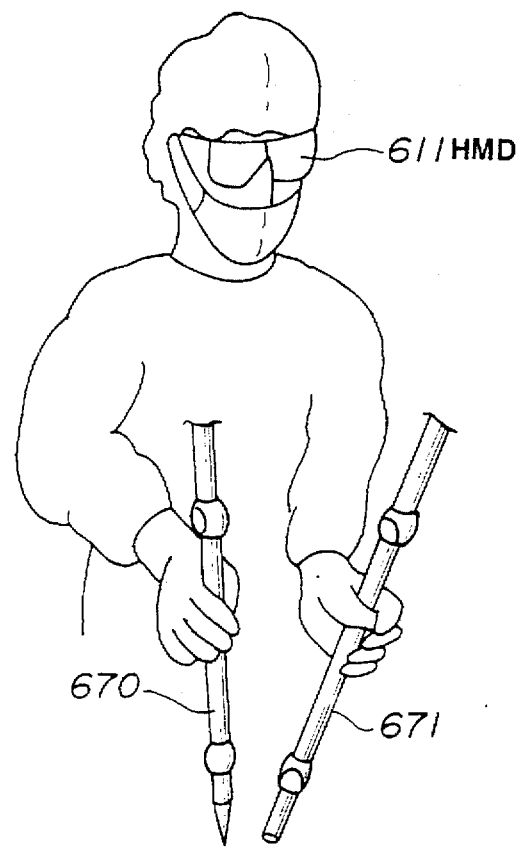
FIG. 42 illustrates a state where a medical operation is being performed.
Figure 43:
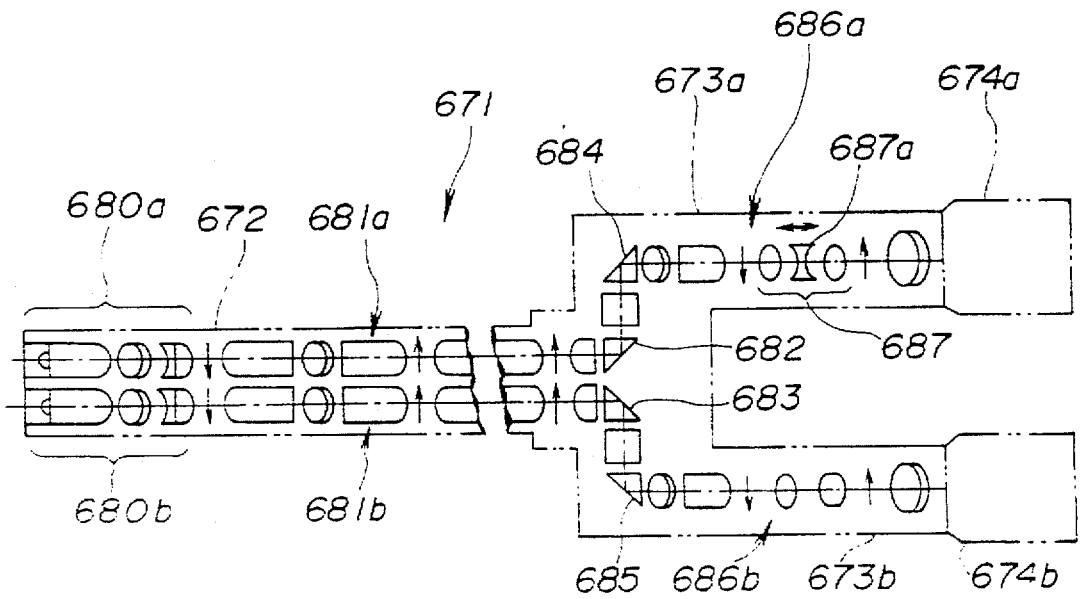
FIG. 43 is a schematic view which illustrates the structure of a stereoscopic endoscope for performing the fluorescent light observation.

FIG. 42 illustrates a state where a surgical operation of the peritoneal cavity is performed by using a stereoscopic endoscope 671 and any of curing tools 670. FIG. 43 illustrates the structure of an optical system of the stereoscopic endoscope 671.

As shown in FIG. 43, the stereoscopic endoscope 671 is a hard stereoscopic endoscope having an optical system for the left eye and for the right eye. The stereoscopic endoscope 671 comprises an elongated insertion portion 672 having a base portion to which two ocular portions 673a and 673b are connected. Adapters 674a and 674b respectively are connected to the ocular portions 673a and 673b to which TV cameras (not shown) are respectively connected. Thus, a normal image and a fluorescent image of an object obtained by the stereoscopic endoscope 671 can be photographed.

The stereoscopic endoscope 671 has a structure in which the ocular portions 673a and 673b, each of which has a substantially L-shape, project over the two side surfaces of the base portion of the insertion portion 672. The TV cameras (for example, corresponding to the normal-light camera 606 and the fluorescent-light camera 607 shown in FIG. 37) to be respectively connected to CCUs (not shown but expressed as CCU-A and CCU-B for convenience) are respectively attached to the adapters 674a and 674b connected to the ocular portions 673a and 673b.

The CCU-A and the CCU-B have the functions of the CCU 608 and the fluorescent image processing apparatus 609 shown in FIG. 37. The CCU-A and CCU-B are connected to a stereoscopic display unit (not shown) for stereoscopically displaying a normal image and a fluorescent image obtained by the stereoscopic endoscope 671 and having a parallax. Furthermore, the HMD 611 is connected to the stereoscopic display unit. The stereoscopic display unit causes images respectively photographed by, for example, the two TV cameras, to be alternately displayed on the HMD 611 in a manner such that the right portion and the left portion are individually displayed. By observing the images by the right and left eyes, a stereoscopic normal image and a fluorescent image of an object can be observed.

Two objective optical systems 680a and 680b for forming an image of an object are disposed in the leading portion of the insertion portion 672 of the stereoscopic endoscope 671. In the rear of the objective optical systems 680a and 680b, relay optical systems 681a and 681b for respectively transmitting the image of the object are disposed. In the rear of the relay optical systems 681a and 681b, that is, in a portion from the base portion of the insertion portion 672 to the ocular portions 673a and 673b, prisms 682 and 683 and prisms 684 and 685 for respectively reflecting the optical axis by an angular degree of 90° are disposed. In the ocular portions 673a and 673b disposed in the rear of the prisms 684 and 685, ocular optical systems 686a and 686b are disposed. The ocular portions 673a and 673b enable the image to be photographed or observed by the naked eye. Note that arrows in FIG. 37 indicate the directions of the image.

Although omitted from illustration, the stereoscopic endoscope 671 has an irradiating optical system in which normal light and excitation light emitted by light source apparatuses (not shown) are transmitted to the leading portion to irradiate the object with normal light and excitation light.

Each of the adapters 674a and 674b has a similar structure to that of, for example, the camera switch unit 605 shown in FIG. 37 and thus the fluorescent light observation is performed similarly.

Either of the ocular optical systems (that is, the ocular optical system 686a) includes a zoom optical system 687 that has a movable lens 687a which adjusts the magnification of the optical system and which can be moved.

When a stereoscopic view is obtained, the magnification is adjusted by the zoom optical system 687 provided for the ocular optical system 686a so that the magnifications of the two optical systems are made to be the same. That is, the zoom optical system 687 longitudinally moves the movable lens 687a so that the magnification of the optical system is changed to make coincide the magnifications of the two optical systems with each other. Thus, a satisfactory stereoscopic observed image can be obtained.

By providing the zoom optical system for at least either of the two optical systems as described above, the magnifications of the optical systems can be changed to make coincide the magnifications of the right and left images of the stereoscopic observed image with each other. Thus, an excellent stereoscopic view can be obtained.

In the stereoscopic endoscope 671 having the foregoing structure, the two object optical systems 680a and 680b having a parallax form the image of an object, and the image of the object is transmitted to the rear end ocular portions 673a and 673b by the relay optical systems 681a and 681b and the ocular optical systems 686a and 686b. Then, the image is photographed by the TV cameras connected to the ocular portions 673a and 673b through the adapters 674a and 674b.

In a case where an image is photographed by connecting the TV cameras to the ocular portions 673a and 673b, the photographed image signals of the object are respectively signal-processed by the CCU-A and the CCU-B. Then, the image is displayed on the HMD 611 through the stereoscopic display unit. Thus, the normal image and the fluorescent image can be stereoscopically observed.

This example facilitates a curing operation even if a fluorescent observation is performed by carrying out the operation by using any of a variety of curing tools 670. In a case where the operation is performed while observing the fluorescent image, a risk of erroneously curing a normal texture except for the diseased portion can substantially be overcome.

Although the examples shown in FIGS. 37 to 43 have an arrangement in which the CCD 620 of the normal-light camera 606 photographs an object with normal light, the CCD 620 may have a color mosaic filter on the incident side thereof so that it serves as a CCD capable of capturing a color image. If a color filter for dividing normal light into red, green and blue is disposed, a normal TV camera capable of photographing a color image can be constituted. The normal observation light source apparatus 603 may sequentially supply red, green and blue irradiating light beams and synchronization with the supply timing may be made to constitute a normal TV camera that is able to photograph a color image.

In a case where the fluorescent observation in the body cavity is transdermically performed, there is a method in which a fluorescent endoscope is individually provided from a conventional normal endoscope so as to be used in combination with the conventional normal endoscope. If the position of the image to be observed with normal light and the position of the fluorescent image are deviated from each other in the foregoing case, an operation, such as a diagnosis, cannot be performed easily. Furthermore, a risk arises that an erroneous diagnosis can be performed or a normal portion is erroneously treated. Therefore, it is important to assuredly align the positions of the normal image and the fluorescent image.

Accordingly, there is a desire for a fluorescent endoscope apparatus having a function of easily and automatically aligning the positions.

A fluorescent endoscope apparatus 700 having the position aligning function will now be described.

Figure 44:
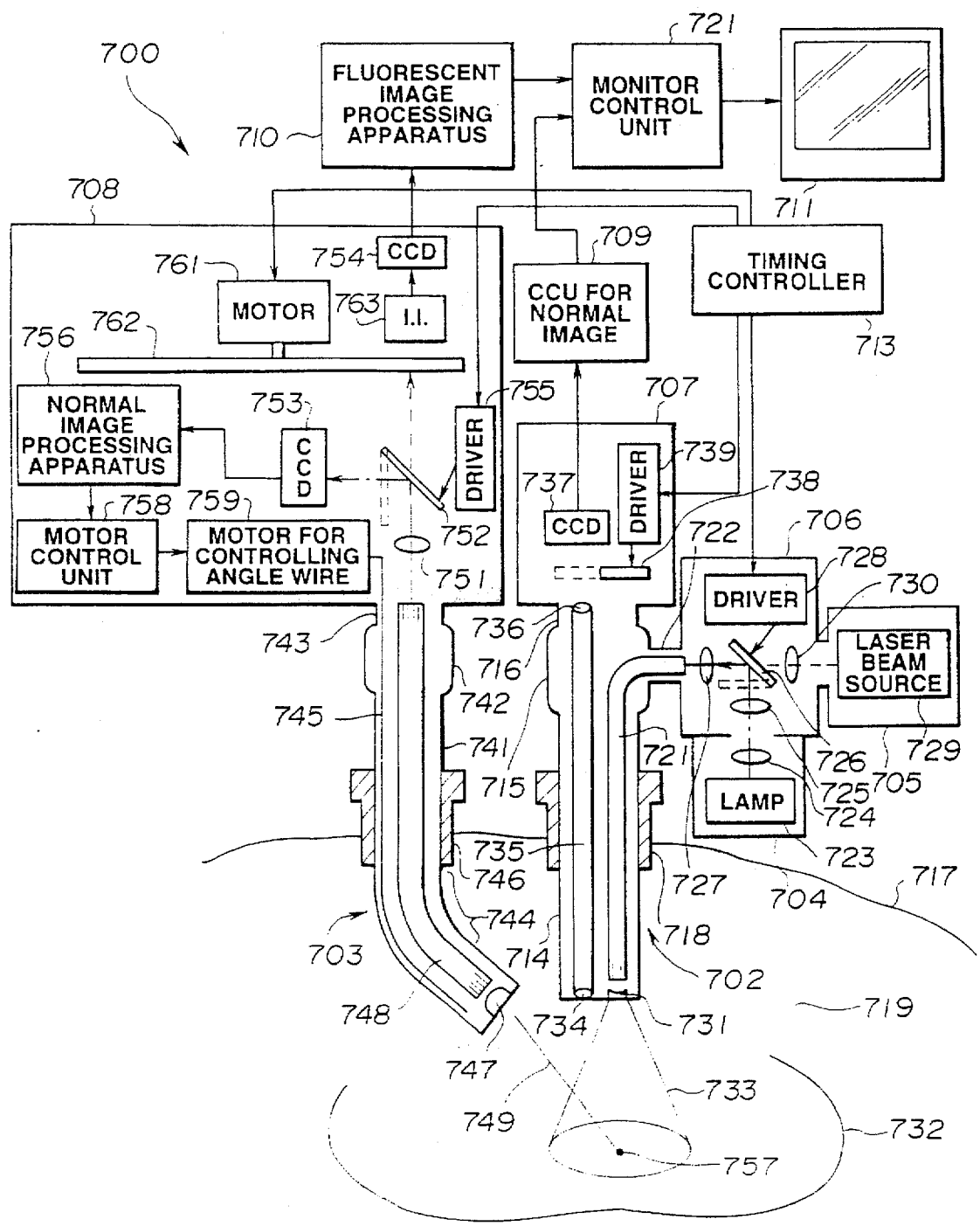
FIG. 44 illustrates the structure of a fluorescent endoscope apparatus having an arrangement in which the normal endoscope and the fluorescent endoscope are provided individually and which has a function of aligning a normal image and a fluorescent image to each other on a monitor.

As shown in FIG. 44, the fluorescent endoscope apparatus 700 having the position aligning function comprises a normal observation scope 702, a fluorescent observation scope 703, a normal observation light source apparatus 704 for emitting normal light, a fluorescent observation light source apparatus 705 for emitting excitation light for use to perform the fluorescent observation, an introduced-light switching apparatus 706 connected to a light guide means of the normal observation scope 702 and arranged to selectively introducing normal light emitted by the normal observation light source apparatus 704 or excitation light emitted by the fluorescent observation light source apparatus 705 into the light guide means, a normal-light camera 707 integrally or detachably connected to the normal observation scope 702, a fluorescent-light camera 708 integrally or detachably connected to the fluorescent observation scope 703, a CCU 709 for a normal image for subjecting an output signal from the normal-light camera 707 to a video data generating process, a fluorescent image processing apparatus 710 for subjecting an output signal from the fluorescent-light camera 708 to a video data generating process, a monitor 711 for displaying an output signal from the CCU 709 for the normal image or that from the fluorescent image processing apparatus 710, a monitor control unit 712 for selectively transmitting an output signal from the CCU 709 for the normal image or from the fluorescent image processing apparatus 710, and a timing controller 713 for controlling the timing of the fluorescent endoscope apparatus 700.

The normal observation scope 702 has, for example, a hard and elongated, insertion portion 714. A handle portion 715 is provided for the insertion portion 714 adjacent to the hand of an operator. An ocular portion 716 is formed at the rear end of the handle portion 715.

The insertion portion 714 is inserted into a body cavity 719 while being guided by a tracheal 718 inserted into a hole in the surface 717 of the body of a patient or the like.

A light guide 721 is inserted into the insertion portion 714, the light guide 721 having a rear end which is inserted into a light guide cable 722 outwardly extending from the holding portion 715 so as to be connected to an output portion of the introduced-light switching apparatus 706.

The introduced-light switching apparatus 706 has two input portions that are connected to the normal observation light source apparatus 704 and the fluorescent observation light source apparatus 705. In the normal observation light source apparatus 704, a lamp 723 for emitting, for example, white normal light is disposed. Light emitted by the lamp 723 is allowed to pass through a lens 724 disposed on the optical path for the lamp 723 so as to be introduced into the introduced-light switching apparatus 706.

In the introduced-light switching apparatus 706, a lens 725 and a mirror 726 for changing the light distribution optical path are sequentially disposed on the optical path that faces the lens 724. When the mirror 726 is at a position designated by a continuous line, normal light is reflected by the mirror 726 and is supplied to an end surface of the light guide 721 through the lens 727. At this time, light from the fluorescent observation light source apparatus 705 is shielded by the mirror 726.

The mirror 726 is switched between the position designated by the continuous line and the position designated by the dashed line by a control driver 728. In the fluorescent observation light source apparatus 705 connected to the residual input portion, an excitation light source 729 is disposed. Excitation light emitted by the excitation light source 729 is, in the introduced-light switching apparatus 706, introduced toward the lens 727 through a lens 730 disposed on the optical path for excitation light.

When the mirror is in a state of retraction (with respect to the excitation light source 729) designated by the dashed line, excitation light is not shielded by the mirror but it is supplied to an end surface of the light guide 721 through the lens 727. At this time, normal light is shielded by the mirror 726.

Light, for example, normal light introduced through the light guide 721 is, from the end surface of the leading portion of the insertion portion 714, emitted forwards through the lens 731 so that the upper surface of an internal organ 732 in the body cavity 719 is irradiated with normal light 733.

The irradiated portion is, by an objective lens 734 attached to an observation window formed in the leading portion, imaged at an imaging position of the object lens 734. The image formed by the objective lens 734 is transmitted to the ocular portion 716 by an image transmission system 735 comprising a relay lens system or the like. Then, an imaging lens 736 forms the transmitted image on a CCD 737 for a normal image disposed in the normal-light camera 707 connected to the ocular portion 716.

A shutter 738 is disposed between the CCD 737 and the imaging lens 736, the shutter 738 being, by a shutter control driver 739, brought to a retraction position designated by the continuous line and a light shielding position designated by the dashed line. The control driver 728 for operating the mirror 726 and the shutter control driver 739 are controlled by the timing controller 713. When the mirror 726 is at the position designated by the continuous line, the shutter 738 is also brought to a position designated by the continuous line.

A normal image photoelectrically converted by the CCD 737 is supplied to the CCU 709 for a normal image so that standard video data is generated. Then, the standard video data is supplied to the monitor control unit 712.

The fluorescent observation scope 703 comprises a flexible and elongated insertion portion 741, a handle portion 742 disposed in the rear of the insertion portion 741 and an ocular portion 743 disposed in the rear of the handle portion 742. A warp-enabled portion 744 is disposed in the vicinity of the leading portion of the insertion portion 741. An end (a leading end) of an angle wire 745 inserted into the insertion portion 741 is secured to a hard leading portion, while another end is connected to an angle-wire control motor 759 for pulling/loosening the angle wire 745. The warp-enabled portion 744 can be warped to a portion that pulls the angle wire 745. Although only one angle wire 745 is illustrated in FIG. 44 to simplify the illustration, four angle wires 745 are inserted to enable four directional movements.

Also the insertion portion 741 is, through a tracheal 746, inserted into the body cavity 719. An objective lens 747 is attached to an observation window formed in the leading portion of the insertion portion 741. The leading surface of, for example, an image guide 748 serving as a flexible image transmission means, is disposed at an image forming position for the objective lens 747.

An image of an object or a fluorescent image irradiated while making the optical axis of the objective lens 747, that is, a position in front of an observation axis (or a visual line)

749, as the center is formed on the leading surface of the image guide 748. The image on the leading surface is, by the image guide 748, transmitted to an end surface of the same adjacent to the ocular portion 743.

The transmitted image is, by an imaging lens 751 disposed in the fluorescent-light camera 708 connected to the ocular portion 743, captured by the second CCD 753 for a normal image or a CCD 754 for a fluorescent image in accordance with a state of setting of a mirror 752 for changing the light-receiving optical path (or a image capturing optical path).

Note that the mirror 752 is rotatively operated between the position designated by the continuous line and the position designated by the dashed line by a mirror control driver 755. In a case where the mirror 726 and the shutter 738 are brought to the positions designated by the continuous lines, the mirror 752 is similarly brought to the position designated by the continuous line due to synchronous control performed by the timing controller 713 through the mirror control driver 755.

If the mirror 752 is at, for example, the position designated by the continuous line, irradiation with normal light 733 is performed and a normal image obtained due to the foregoing irradiation is reflected by the mirror 752 so that a normal image is formed on the second CCD 753 for a normal image. An image signal photoelectrically converted by the CCD 753 is supplied to a normal image processing apparatus 756. By detecting the position at which the captured image has the maximum brightness, a maximum brightness position 757 in an irradiation range in a case where the internal organ 732 is irradiated with normal light 733 is detected.

The result of the detection is supplied to a motor control unit 758. The motor control unit 758 controls the rotation of an angle-wire control motor 759 in accordance with the result of the detection so that the angle wire 745 connected to the angle-wire control motor 759 is pulled. Thus, the warp-enabled portion 744 is warped so that the observation axis 749 is moved to the maximum brightness position 757. A position aligning mechanism is provided which sets the maximum brightness position 757 on the observation axis 749 as illustrated so as to align the position such that substantially the same positions of the normal image and the fluorescent image are always captured.

When the mirror 752 is brought to the position designated by the dashed line, also the mirror is brought to the position designated by the dashed line. Thus, the subject portion of the object is irradiated with excitation light emitted by the excitation light source 729. Fluorescent light emitted by the subject portion is, through the observation optical system for the fluorescent observation scope 703, that is, the objective lens 747 and the image guide 748, introduced into the fluorescent-light camera 708.

Introduced fluorescent light is not shielded by the retracted mirror 752, and is passed through the filter of a rotative filter 762 that is rotated by a rotative filter-control motor 761. Then, fluorescent light is optically amplified by an I.I. 763 and imaged on a CCD 754 for fluorescent image. The CCD 754 photoelectrically converts fluorescent light.

The positions of the CCD 753 and the I.I. 763 are at the conjugate positions with respect to the lens 751 so that an image formed by the CCD 753 and an image photoelectrically amplified by the I.I. 763 and formed on the CCD 754 are conjugate images (at least having the same size).

An image signal obtained by the CCD 754 is supplied to the fluorescent image processing apparatus 710 so as to be subjected to a process for generating video data for pseudo-color or the following calculations, then processed data being transmitted to the monitor control unit 712.

The rotative filter 762 has a plurality of filters having different transmissive wavelength bands so that fluorescent images having the plurality of wavelength bands are sequentially captured. In the fluorescent image processing apparatus 710, video data for the pseudo-color display is generated from the fluorescent images having the plurality of wavelength bands. Furthermore, calculations are performed to obtain the ratio of signal levels corresponding to the same position of the fluorescent images having the two wavelengths $\lambda 1$ and $\lambda 2$, for example, as shown in FIG. 36(c). Whether or not the value is greater than a predetermined value is determined by a comparison process performed by a comparator. Thus, whether or not the portion having the foregoing value is a diseased portion or a healthy portion is determined.

If a determination has been made that there is a possibility that the subject portion is a diseased portion, a discrimination signal causes a display control signal to be transmitted to the monitor control unit 712. As a result, a normal image is displayed on the right portion of the monitor 711 and a pseudo-color fluorescent image is displayed on the left portion, for example.

At this time, video data having the wavelengths $\lambda 2$ and $\lambda 2$ and obtained by using, for example, the band-pass filter for permitting the two wavelengths $\lambda 1$ and $\lambda 2$ provided for the rotative filter 762 is, as red and green data, transmitted to the monitor 711 to transmit the foregoing discrimination signal as blue video data. Thus, the operator is able to easily recognize the portion having a possibility to be a diseased portion in accordance with a fact whether or not blue portion is present.

The monitor control unit 712 may have a mechanical display selection means, such as a foot switch, so that an image to be displayed on the monitor 711 is selected and displayed by operating the display selection means. For example, the following operations are enabled: a normal image is displayed in the central portion of the monitor 711; the normal image is displayed in the right portion of the monitor 711; a fluorescent image is displayed in the central portion of the monitor 711; the fluorescent image is displayed in the left portion of the monitor 711; or the normal image is displayed in the right portion of the monitor 711 and as well as the fluorescent image is displayed in the left portion while superimposing the two images.

The rotation of the rotative filter control motor 761 is also controlled by the timing controller 713. In synchronization with the timing at which the mirrors 726 and 552 and the shutter 738 are disposed at the positions designated by dashed lines, a plurality of filters are sequentially disposed on the image capturing optical path.

Note that the image sensing system for the normal observation scope 702 and that for the fluorescent observation scope 703 have substantially the same characteristics. For example, the distance from the objective lens (734 or 747) to the object and the like are the same so that, if the same object image is captured image signals having the same wavelength (however, difference in the signal level permitted) are transmitted from the CCDs 737 and 754. That is, the photography under the same condition enables object images having the same size to be obtained.

In another condition that does not satisfy the foregoing condition, for example, if different size photography is performed, a process for making the size to be the same (coincide) is required at a moment before or after the position alignment. Even if the foregoing condition is met, a process for making the size to be the same may be performed as described later.

The operation of the fluorescent endoscope apparatus 700 will now be described.

The timing controller 713 synchronizes the following units: the mirror 726 for changing the light distribution optical path; the mirror 752 for changing the image capturing optical path; the rotative filter 762; and the shutter 738. As a result, when the mirror 726 is at the position designated by the continuous line, normal light is introduced from the lamp 723 to the light guide 721. The shutter 738 is opened so that a normal image is formed on the CCD 737 through the image transmission system 735. The mirror 752 for changing the image capturing optical path is also at the position designated by the continuous line so that a normal image is introduced into the CCD 753 through the image guide 748.

When the mirror 726 for changing the light distribution optical path is at the position designated by the dashed line, excitation light is introduced from the excitation light source into the light guide 721 and therefore the shutter 738 is closed. Also the mirror 752 for changing the image capturing optical path is at the position designated by the dashed line so that a fluorescent image is introduced into the I.I. 763 through the image guide 748. At this time, the fluorescent image is, by the rotative filter 762, divided into a plurality of images having different wavelengths.

The timing controller 713 performs control to switch the foregoing two states. As a result, this example enables both of the normal image and the fluorescent image to always be captured.

The process for displaying the normal image and the fluorescent image on the monitor 711 will now be described.

Initially, an image obtained from normal light is supplied from the CCD 737 to the monitor control unit 712 through the CCU 709. On the other hand, a plurality of fluorescent images are, by the I.I. 763, amplified to be supplied to the fluorescent image processing apparatus 710 through the CCD 754 so that the fluorescent images are subjected to a predetermined calculation. Thus, a single fluorescent image is supplied to the monitor control unit 712.

The monitor control unit 712 displays the normal image and/or fluorescent image on the monitor 711. As the display method, any of the following methods may be employed: a method of displaying either image by manual switching; a method in which display is performed in accordance with the result of the calculation performed by the fluorescent image processing apparatus 710; a superimposing method; and a method in which the two types of images are synthesized and the synthesized image is displayed.

A method for aligning the positions of the normal image and the fluorescent image will now be described.

When normal light irradiation is performed, a normal light image is introduced into the normal image processing apparatus 756 through the image guide 748, the mirror 752 and the CCD 753. The normal image processing apparatus 756 detects the maximum brightness position 757 under the irradiation of normal light 733 on the internal organ 732.

In accordance with the result of the detection, the motor control unit 758 rotates the angle-wire control unit 759 so that the angle wire 745 is controlled. As a result, the observation axis 749 of the fluorescent observation scope 703 is moved to the maximum brightness position 557 so that the illustrated state is realized. Thus, the normal image and the fluorescent image are brought to a state where the same positions are always photographed.

As the method for moving the observation axis 749 of the fluorescent observation scope 703, any of the following methods may be employed as well as the method using the wire: a method using a shape memory member; and a method using an air pressure warping means.

According to this example, the positions of the normal image and the fluorescent image can easily and automatically be aligned. Therefore, the operator is able to easily confirm the position of an image that corresponds to the position of another image between the normal image and the fluorescent image. Thus, a diagnosis and operation can easily be performed. In addition, the diagnosis and the operation can be completed in a short time.

Figure 45:
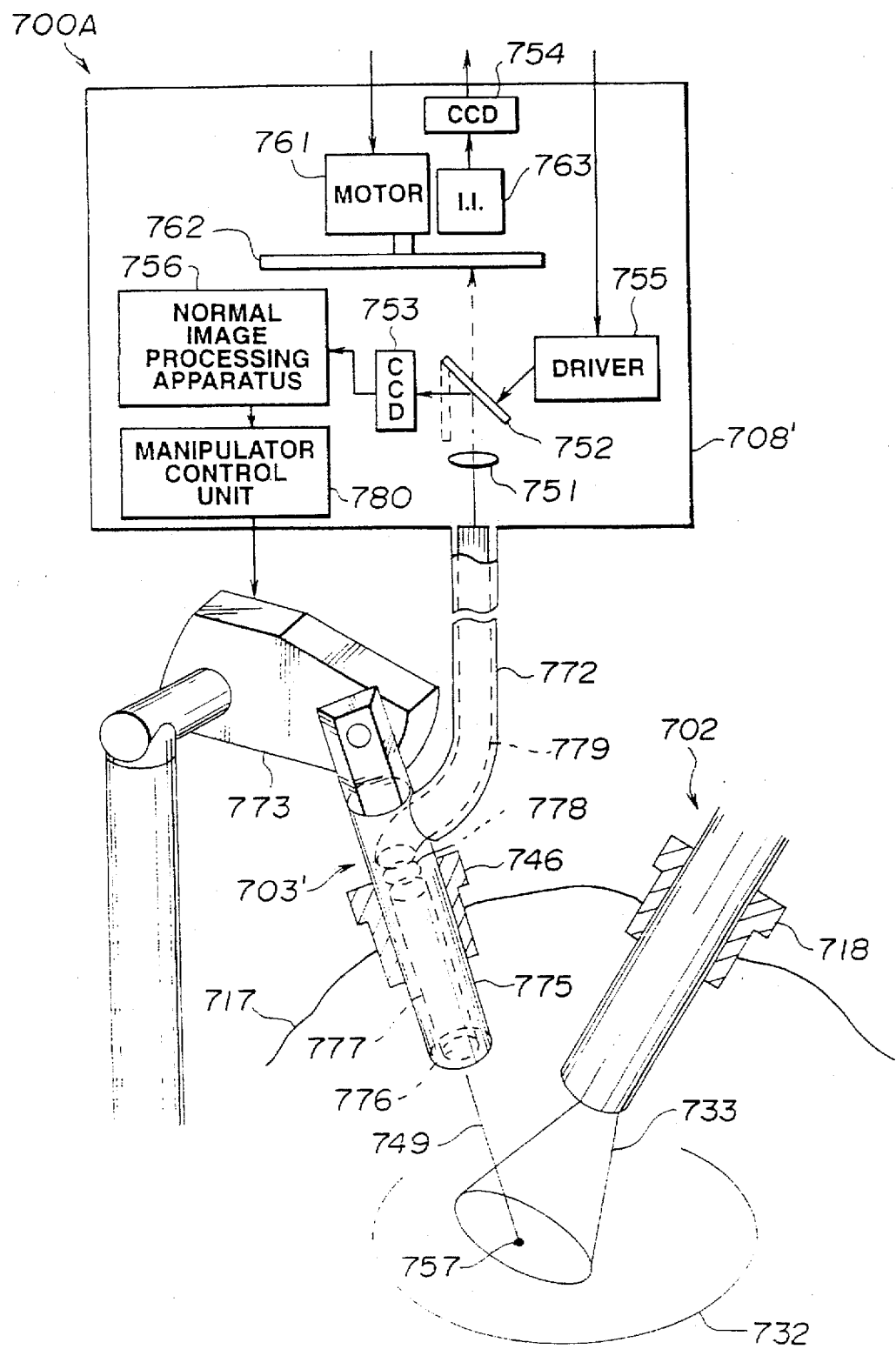
FIG. 45 illustrates another structure of the fluorescent endoscope apparatus having an arrangement in which the normal endoscope and the fluorescent endoscope are provided individually and which has the function of aligning the normal image and the fluorescent image to each other on a monitor.

FIG. 45 illustrates an essential portion of another embodiment of the fluorescent endoscope apparatus 700 having the function of automatically aligning the positions.

In this embodiment, a fluorescent observation scope 703' is provided which is different from the fluorescent observation scope 703 of the fluorescent endoscope apparatus 700 shown in FIG. 44. Therefore, the fluorescent endoscope apparatus 700 comprises a fluorescent-light camera 708' connected to the rear end of an image guide cable 772 of the fluorescent observation scope 703' and a manipulator 733 for moving the observation axis 749 of the fluorescent observation scope 703'. The structures except the mechanism for moving the observation axis 749 are the same as those shown in FIG. 44.

The fluorescent observation scope 703' has, for example, a hard, insertion portion 755 into which an objective lens 776 and a relay lens system 777 are inserted, the relay lens system 777 being used to transmit the optical image to the rear end of the insertion portion 775.

An optical image transmitted to the rear end of the insertion portion 775 is, by an imaging lens 778, formed on the leading surface of an image guide 779 serving as a flexible image transmission means. The image guide 779 transmits the optical image to the rear end surface of the image guide cable 772 so as to be supplied to the fluorescent-light camera 708'.

The rear end of the insertion portion 775 of the fluorescent observation scope 703' is connected to the manipulator 733 having a plurality of axes. The plural axes of the manipulator 733 are rotated under control of a manipulator control unit 780 included in the fluorescent-light camera 708' so that the axial direction of the insertion portion 775 is changed. Thus, the direction of the observation axis 749 is changed.

The manipulator control unit 780 is controlled in accordance with the output from the normal image processing apparatus 756.

Although the example shown in FIG. 44 has the arrangement that the warp-enabled portion 744 is warped due to the traction of the angle wire 745 to change the observation axis 749, this embodiment has an arrangement that: the fluorescent observation scope 703' having the hard insertion portion 775 is used; and the manipulator 733 changes the axial direction of the insertion portion 775 to change the observation axis 749, so that the position alignment is performed to bring the maximum brightness position 757 on the observation axis 749.

The operation will now be described. The operations are the same as those of the example shown in FIG. 44 except the direction in which the observation axis 749 of the fluorescent observation scope 703' is moved.

When the normal light irradiation is performed, a normal light image is, through the optical system of the fluorescent observation scope 703', supplied to a normal image processing apparatus 756 included in the fluorescent-light camera 708' connected to the rear end of the image guide cable 772. Thus, the normal light maximum brightness position 757 on the internal organ 732 is detected similarly to the example shown in FIG. 44.

In accordance with the result of the detection, the manipulator 733 is controlled through the manipulator control unit 780 so that the insertion portion 775 of the fluorescent observation scope 703' is moved. Thus, the position alignment is performed so that the observation axis 749 is moved onto the normal light maximum brightness position 757.

As compared with the example shown in FIG. 44, this embodiment has the arrangement that the hard insertion portion 775 is used to move the insertion portion 775 by the manipulator 733. Therefore, the shake of the observation optical system of the fluorescent observation scope 703' can be prevented satisfactorily and the accuracy in the position alignment can be improved. Thus, the positions of the normal image and the fluorescent image can be accurately aligned even further.

As a result, the positional relationship between the normal image and the fluorescent image can be easily confirmed similarly to the apparatus shown in FIG. 44. Thus, an environment, in which a diagnosis and an operation can easily be performed in a short time, can be realized.

Although the manipulator 733 is, in the example shown in FIG. 45, connected to the rear end of the insertion portion 775, another structure may be employed in which a handle or control portion is provided in the rear portion of the insertion portion 775 and the manipulator 733 is connected to the handle or control portion.

The structure is not limited to the foregoing arrangement that the observation axis 749 is aligned to the maximum brightness position 757 by inclining and moving the fluorescent observation scope 703' by the manipulator 733. For example, an arm may be employed in the manipulator 733 shown in FIG. 45 in such a manner that an end of the arm is connected to the rear end of the Insertion portion 775 and another end of the arm is rotated by a motor or the like to align the maximum brightness position 757 onto the observation axis 749.

The locus for which the observation axis 749 is, at this time, moved within one plane (that is perpendicular to the rotation axis of the motor). Previous setting is required such that the observation axis 749 and the optical axis of the lens 731 are included within the plane.

Although the fluorescent observation scope 703' shown in FIG. 45 has the structure that the image transmitted by the relay lens system 777 is then transmitted to the fluorescent-light camera 708' through the image guide 579 inserted into the flexible image guide cable 772, the structure is not limited to this and another structure may be employed.

For example, the fluorescent-light camera 708' may be accommodated or disposed in the rear portion of the insertion portion 775 which is the image forming position for the lens 778. As an alternative to the flexible image guide cable 772, a rigid image transmission means, such as a relay lens system, may be used to transmit the image to the fluorescent-light camera 708'.

Note that the examples shown in FIGS. 44 and 45 have the arrangement that the irradiation with normal light 733 is performed in a state where the observation axis of the normal observation scope 702 runs parallel to the optical axis of the lens 731. Thus, an assumption is made that the distance between the foregoing two elements (assumed to be "d" for convenience) is short enough to be ignored as compared with the distance to the object (the distance to the maximum brightness position 757 on the internal organ 732 shown in FIGS. 46 or 47).

While considering the distance d, the following position alignment may be performed.

In a case where the two scopes 702 and 703 are inserted into the body cavity 719 in the structure shown in FIG. 44, setting is made such that the optical axis (that coincides with the observation axis 749) of the scope 703 is present in a plane which includes the optical axis of the lens 731 and that of the lens 734.

The foregoing setting can easily be established by rotating the scope 702 around the axis of the insertion portion 714. FIG. 44 illustrates a state where the foregoing setting has been established (however, the warp-enabled portion 744 is straightened).

In the foregoing state, irradiation with normal light 733 is performed, and then the maximum brightness position 757 is detected from a photography signal obtained by the CCD 753. Then, the insertion portion 741 is forwardly moved (inserted) or rearwards moved so that the maximum brightness position 757 is again detected. By using the quantity of deviation of the maximum brightness position 757 on the two images and a predetermined length, a position (a position deviated by d toward the left from the maximum brightness position 757 shown in FIG. 45 on the internal organ 732 positioned forwards on the optical axis of the lens 734) adjacent to the maximum brightness position 757 after the movement has been performed is calculated. Then, the obtained position is made to be the aimed position to which the observation axis 749 of the scope 703 is aligned.

In accordance with the calculated aimed position, the motor 759 is rotated to warp the warp-enabled portion 744 in a direction in which the observation axis 749 approaches the aimed position. When the observation axis 744 reaches the aimed position, the rotation is stopped and the positional alignment is completed.

By performing the positional alignment as described above, the positional alignment can be performed further precisely and the positional relationship between the normal image and the fluorescent image on the two images can easily be performed.

Another size coincidence process may be employed in which: the insertion portion 775 is, for example, moved toward the observation axis 749 to change the size of the image captured by the fluorescent observation scope 703 or 703'; and the movement is stopped when the size coincides with that of the image captured by the normal observation scope 702 (the scope 702 may, of course, be moved in the direction of the axis of the insertion portion 702).

The size coincidence may be performed by changing the size by moving the lens 751 shown in FIG. 44 or 45 in the direction of the optical axis of the lens 751.

The foregoing size coincidence process enables the positions of the normal image and the fluorescent image on the respective images can be made further accurately coincide with each other. Thus, a process, such as a diagnosis or an operation, can be easily completed.

The foregoing size coincidence enables the positions of the normal image and the fluorescent image on the respective images to be made accurately coincide with each other even if the sizes are different from each other due to a fact that the optical systems of the normal observation scope 702 and the fluorescent observation scope 703' have different image-forming characteristics (for example, the focal distance or an angle of view) or a fact that the distance from the leading portion of the normal observation scope 702 to the object and the distance from the leading portion of the fluorescent observation scope 703' to the object are different from each other.

The size coincidence process may be performed automatically. The same may be performed manually by an operator or the like. The positional alignment may be performed manually (by the hand). Selection of either the automatic setting mode or the manual setting mode may be permitted.

The fluorescent endoscope apparatus 700 or 700A may have a structure that the output from the CCD 753 is transmitted to a second normal image CCU or the like and video data generated by a second normal image CCU is displayed on the monitor 711 through the monitor control unit 712.

If foregoing video data and video data generated by the normal image CCU 709 are alternately displayed on the monitor 711 and, in synchronization with the alternate display, a liquid crystal glasses for alternately transmitting/ shielding right and left liquid crystal is used to observe the display, stereoscopic observation can be performed by the operator.

Video data generated by the second normal image CCU and video data generated by the normal image CCU 709 may be supplied to a stereoscopic image synthesizing apparatus to generate video data of stereoscopic image so as to be displayed on an image display means, such as the monitor 711.

Although the fluorescent endoscope apparatus 700 or 700A has the arrangement that the positional alignment is performed by detecting the maximum brightness position and the fluorescent observation scope 703 or 703' is, by warping for example, inclined to bring the maximum brightness position (or the aimed position) onto the observation axis, a position of another brightness level may be detected in place of the maximum brightness position.

For example, another arrangement may be employed in which a position having a brightness level which is somewhat less than the maximum brightness is detected by the fluorescent observation scope 703 or 703' to be used as a reference position and the fluorescent observation scope 703 or 703' is moved to cause the reference position to overlap the image of the normal observation scope.

Either scope may be moved to align the positions in a manner such that the correlation between the image captured by the normal observation scope 702 and the image (for example, the image captured by the CCD 753) captured by the fluorescent observation scope 703 or 703' is a maximum. At this time, either scope may be moved in such a manner that the maximum brightness positions of the two images overlap. At least either scope may be moved to cause another reference position or a plurality of reference positions to overlap.

Although the position aligning irradiation is, in the structures shown in FIGS. 44 and 45, performing by using normal light emitted through the light guide 721 of the normal observation scope 702, irradiation light is not limited to this. The light guide 721 may be provided for the fluorescent observation scope 703 or 703'. At this time, the positional alignment is required to incline the normal observation scope 702 by a manipulator or the like. In a case where a soft endoscope is used which comprises a warp-enabled portion provided for the insertion portion of the normal observation scope 702, the warp of the warp-enabled portion may be controlled to perform the positional alignment.

Although each of the foregoing embodiments has the structure that the I.I. 763 for the optical amplification is disposed in front of the fluorescent image capturing CCD 754 in order to obtain video data having a level similar to that of video data of the normal image, a two-dimensional lock-in amplifier may be, for example, provided for the fluorescent image processing apparatus 710 in place of the I.I. 763.

Figure 46:
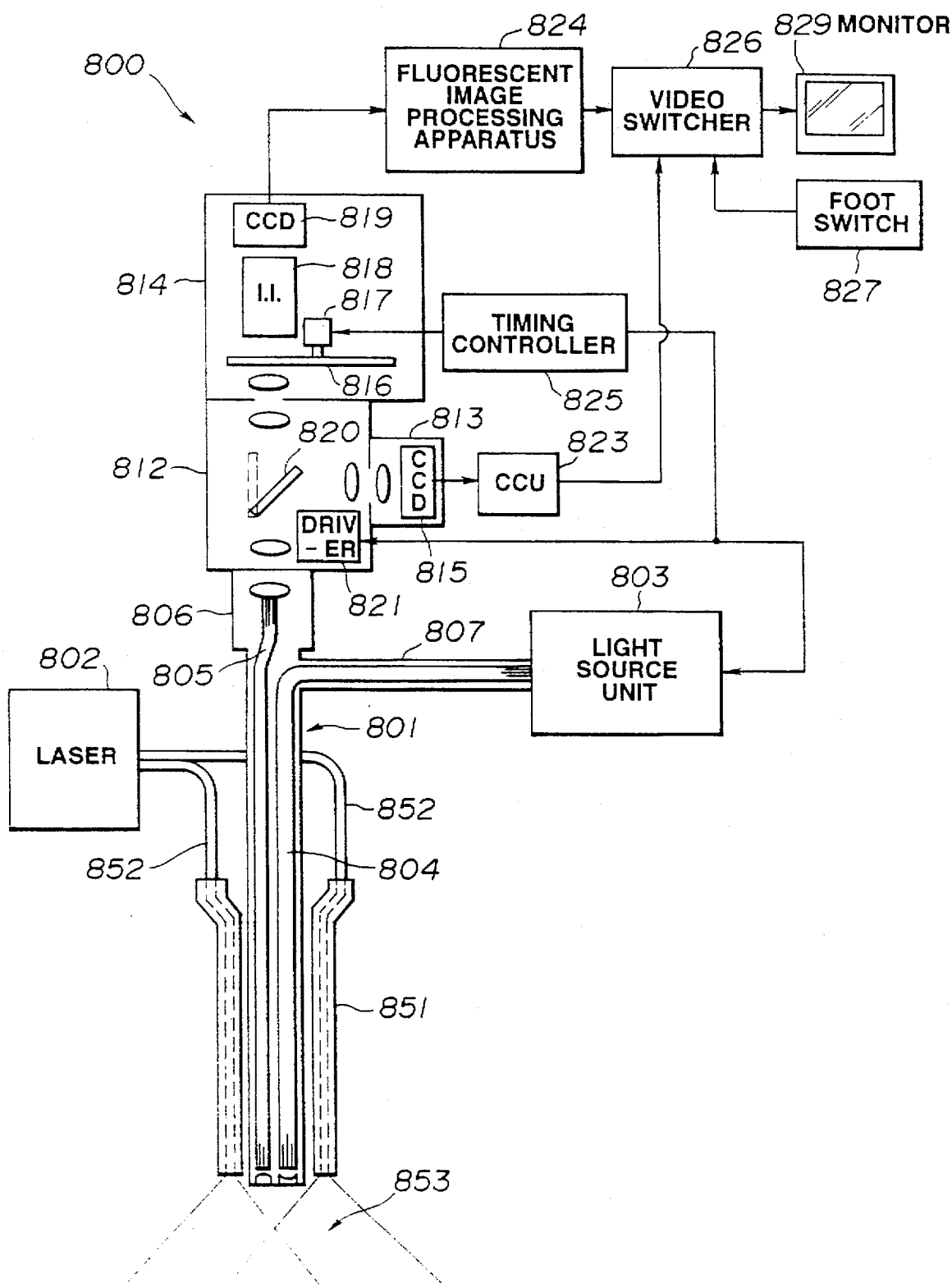
FIG. 46 illustrates the structure of a fluorescent endoscope apparatus having a guide pipe which is provided with an image guide.

An example of a guide pipe for introducing the fluorescent observation endoscope into a subject portion will now be described with reference to FIGS. 46 and 47.

A fluorescent endoscope apparatus 800 according to this example comprises a guide means for introducing an endoscope 801 to be inserted into the body cavity to a subject portion, the guide means being a guide pipe 851 which comprises a trachea tube or a tracheal.

An excitation-light guide 852 connected to the fluorescent observation light source apparatus 802 and serving as a light introducing means for introducing excitation light emitted by the excitation light generating apparatus is inserted into the guide tube 851 from the position adjacent to the hand of the operator to the leading portion of the guide tube 851. Thus, excitation light can be introduced from the fluorescent observation light source apparatus 802.

Figure 47:
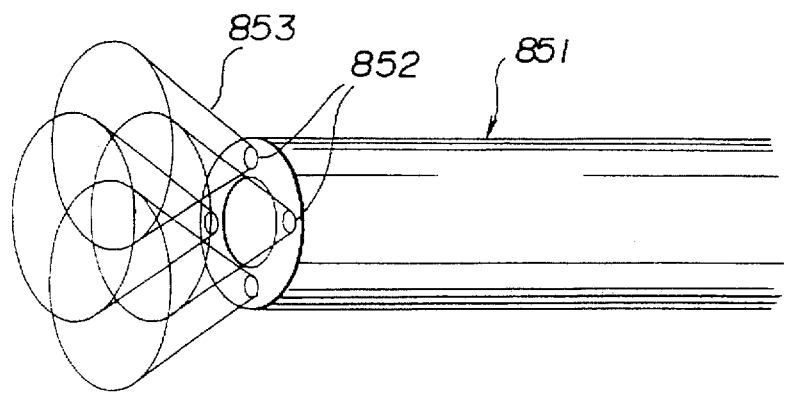
FIG. 47 is a perspective view which illustrates the guide pipe shown in FIG. 46.

As shown in FIG. 47, the excitation-light guide 852 has a leading portion that appears on the leading surface of the guide tube 851 so that excitation light 853 emitted by the fluorescent observation light source apparatus 802 emits through the leading portion. In the structure shown in FIG. 47, four excitation-light guides 852 are inserted so as to uniformly and forwards emit excitation light 853.

In this embodiment no introduced-light switching apparatus for switching the light source is provided. An end of a universal cord 807 of the endoscope 801 is directly connected to the normal observation light source apparatus 803 so that normal light emitted by the normal observation light source apparatus 803 is introduced into a light guide 804 in the endoscope 801 so as to be emitted by the leading portion of the endoscope 801.

A normal-light camera 813 and a fluorescent-light camera 814 are, through a camera switch unit 812, connected to an ocular portion 806 of the endoscope 801. A CCU 823 for signal-processing a normal image signal photographed by the normal-light camera 813 and a fluorescent image processing apparatus 824 for signal-processing a fluorescent image signal photographed by the fluorescent-light camera 814 are connected to a video switcher 826. The video switcher 826 selectively switches the normal image signal supplied from the CCU 823 and the fluorescent image signal supplied from the fluorescent image processing apparatus 824 in accordance with an instruction issued from a foot switch 827 to transmit the selected image signal to a monitor 829.

When the fluorescent light observation is performed with the fluorescent endoscope apparatus 800 according to this example, a guide tube 851, such as the trachea tube or the tracheal, is inserted to a subject portion to be observed in the body cavity. Then, the insertion portion of the endoscope 801 is inserted into an inner hole of the guide tube 851 so that the endoscope 801 is inserted into the body cavity until it reaches the subject portion to be observed. When the normal light observation is performed, white normal light emitted by normal observation light source apparatus 803 is used to irradiate the subject portion to be observed through the light guide 804 of the endoscope 801. Then, the normal-light camera 813 photographs a normal image to generate a normal image video signal.

When the fluorescent light observation is performed, the subject portion to be observed is irradiated with excitation light emitted by the fluorescent observation light source apparatus 802 through the excitation-light guide 852 inserted into the guide tube 851. Then, a fluorescent image is photographed by the fluorescent-light camera 814 to generate a fluorescent image video signal.

The normal image signal and the fluorescent image signal can arbitrarily be switched in accordance with an instruction issued from the foot switch 827 and the selected signal is transmitted to the monitor 829 so as to be displayed.

As described above, this example comprises the excitation light introducing means that is provided individually from the light guide of the endoscope. Furthermore, the guide tube connected to the endoscope is provided. Thus, a wide area can uniformly be irradiated with excitation light, causing an excellent fluorescent image to be obtained. Therefore, an accurate fluorescent light diagnosis can be performed.

The structure of the foregoing image guide for the endoscope will now be described.

An endoscope having the image guide has an arrangement that the number of fibers constituting the image guide is increased by reducing the outer diameter of each fiber (to, for example, φ7.5μ). Although the reduction in the diameter of the fiber has slightly lowered the efficiency of transmitting red light in the periphery of the image guide, the normal endoscope observation has no problem from the foregoing fact.

However, a technology for diagnosing a diseased portion, such as a cancer, by using fluorescent light involves inter-wave calculations in order to obtain the difference between green wavelength region and red wavelength region. Thus, the deterioration in the efficiency of transmitting red light in the periphery of the image guide raises a risk that the discrimination between a diseased portion and a healthy portion is performed erroneously.

Accordingly, this embodiment comprises the image guide constituted in such a manner that the efficiency of transmitting red region in the periphery portion of the image guide can be improved and thus the discrimination between a healthy portion and a diseased portion can accurately be performed while improving the resolution by increasing the number of fibers.

That is, optical fibers constituting the image guide are arranged such that optical fibers having red wavelength characteristics are increased in the periphery portion of the image guide as compared with that of the optical fibers disposed in the central portion of the image guide.

Figure 48A:
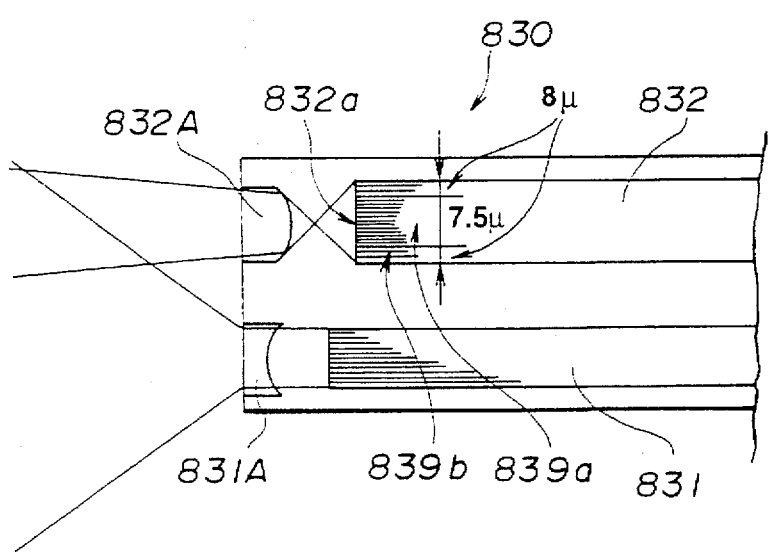
FIG. 48(a) is a horizontal cross sectional view which illustrates the configuration and structure of optical fibers constituting the image guide.
Figure 48B:
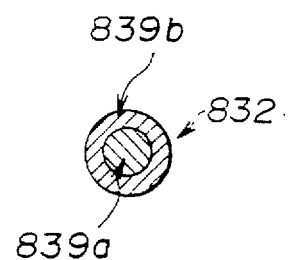
FIG. 48(b) is a front cross sectional view which illustrates the configuration and structure of the optical fibers shown in FIG. 48(a)
Figure 48C:
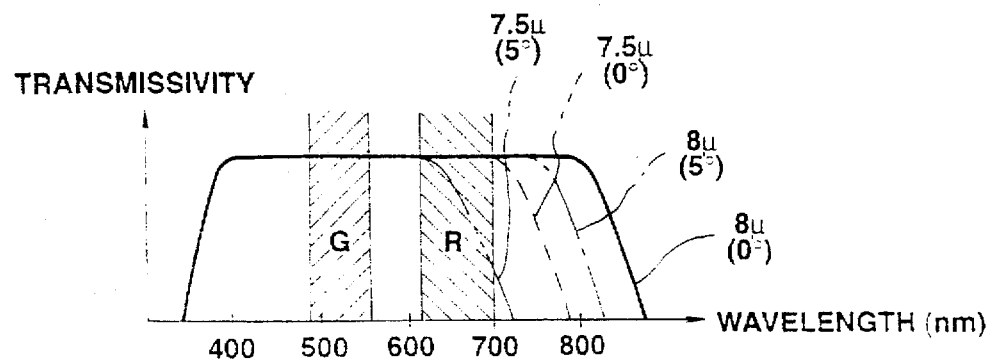
FIG. 48(c) illustrates the relationship between the wavelength and transmissivity.

As shown in FIG. 48, the leading portion of the endoscope 830 comprises: a light guide 831 for transmitting excitation light emitted by a normal observation light source apparatus 50; a concave lens 831A for diffusing excitation light supplied through the light guide 831 to irradiate the portion in the body cavity; an objective lens 832A for projecting distributed fluorescent light realized by excitation light to an end surface 832a of the image guide 832; and an image guide 832 for transmitting a fluorescent image to a direction toward the ocular portion. The image guide 832 is constituted by optical fibers each having a diameter of 7.5 μm and disposed in the central portion of the image guide 832 and optical fibers each having a diameter of 8 μm and disposed in the peripheral portion of the same.

Excitation light used to irradiate the subject portion to be observed through the light guide 831 and the concave lens 831A causes fluorescent light corresponding to a diseased portion and a healthy portion to be generated. The obtained fluorescent image is projected onto the end surface of the image guide 832 by the objective lens 832A.

Light beams of the projected image are, while making a certain angle, made incident on an incidental surface of the optical fibers constituting the end surface 832a of the image guide 832. For example, the light beams are substantially perpendicularly made incident upon the incidental surface of the optical fibers in the central portion of the image guide 832. On the other hand, the light beams are made incident on the peripheral portion, while being inclined by about 5°.

The wavelength characteristics among the outer diameters of the optical fibers, the incidental angles 0° and 5° of the light beams are as shown in FIG. 48(b). That is, if the outer diameter of the optical fiber is 10μ or less, the thickness of the clad is about 1μ or less and thus a cutoff frequency is present from red to near infrared region. That is, the thickness of the clad is thinned in proportion to the reduction in the outer diameter of the optical fiber. As a result, light in the long wavelength region, that is from the red to the near infrared region cannot be transmitted because it can be lost through the fiber.

If the incidental angle of the optical fiber is enlarged, a portion of light exceeds a limit for the incidental angle and it is also lost through the fiber. Therefore, if a fiber having a diameter of 7.5 μm encounters an inclination of the incidental angle of about 5°, the efficiency of transmitting red region light deteriorates. A cancer diagnosing operation is performed by obtaining the ratio of green light having a wavelength of 480 nm to 540 nm and red light having a wavelength of 620 nm to 700 nm.

If the image guide is composed of optical fibers each having a diameter of 7.5 μm, red light decays in the periphery of the image guide. Thus, a disease cannot easily be detected. By constituting the peripheral portion having a large incidental angle by 8 μm-optical fibers, the red band regions can be increased. As a result, all regions of the image guide are able to have a uniform transmission efficiency.

Even if light beams in the periphery of the image guide are made incident on the surfaces of the optical fibers, omission of red light beams can satisfactorily be prevented because the red band regions are increased in the optical fibers. As a result, a diseased portion and a healthy portion can be determined regardless of the position of the portion to be observed.

As a result, the decay of red light beams in the periphery can be prevented while improving the resolution by increasing the number of fibers because the efficiency to transmit the red region in the periphery can be improved. When a diseased portion and a healthy portion are determined in accordance with the ratio of green and red light beams for example, excellent discrimination between the two can be performed on the overall observed region because the efficiency for transmitting green and red beams does not deteriorate in the peripheral portion.

The outer diameter may be 7.5 μm in place of 8 μm and the clad may be thickened. Although the image guide is constituted by 7.5 μm and 8 μm fibers, the image guide may be constituted by plural types of fibers respectively having diameters of 8.3 μm, 8 μm, 7.7 μm and 7.4 μm.

Figure 49:
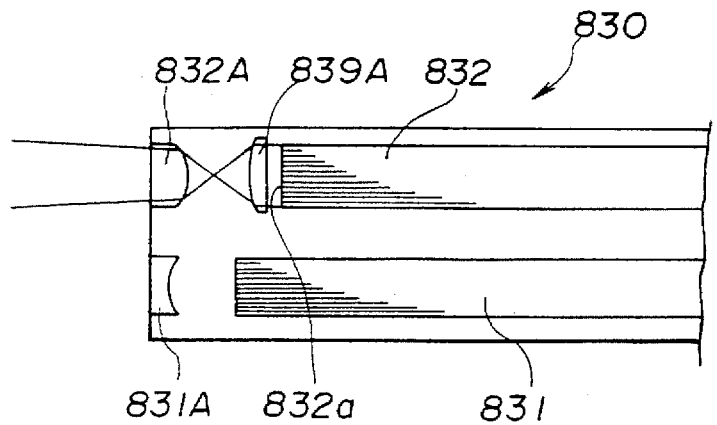
FIG. 49 illustrates a structure in which an optical-axis conversion device is disposed on the leading surface of the image guide.

As a modification of the example shown in FIG. 48, an optical-axis conversion device 839A for converting the optical axis of an image to be substantially perpendicular to the optical fibers of the image guide 832 may be, as shown in FIG. 49, disposed between the objective optical system 832A at the leading portion of the endoscope 830 and the end surface 832a of the image guide 832. As a result, a fluorescent image obtained from excitation light is made incident through the objective optical system 832A. Furthermore, the optical-axis conversion device 839A having, for example, a convex-lens shape, causes the axis of the image to be substantially perpendicular to the end surface 832a of the image guide 832. Therefore, even if the image guide 832 comprises optical fibers each having an outer diameter of 7.5 μm, the necessity for changing the outer diameter of the optical fibers depending upon the positions can be eliminated. Therefore, the process for manufacturing the image guide can be simplified.

A third embodiment of the present invention will now be described with reference to FIGS. 50 and 51.

This embodiment comprises an electronic endoscope in place of the endoscope having the image guide according to the first and second embodiments to observe both normal image and a fluorescent image.

Figure 50:
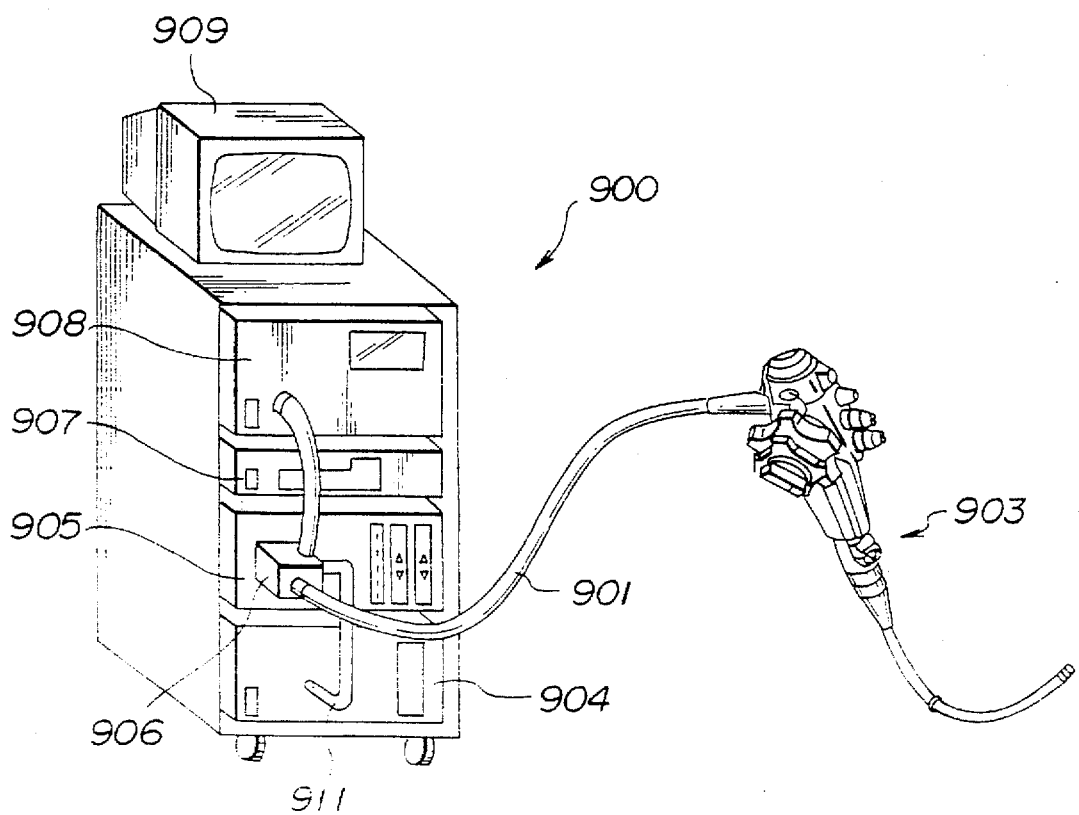
FIG. 50 is a perspective view which illustrates the structure of a fluorescent endoscope apparatus having an electronic endoscope.
Figure 51:
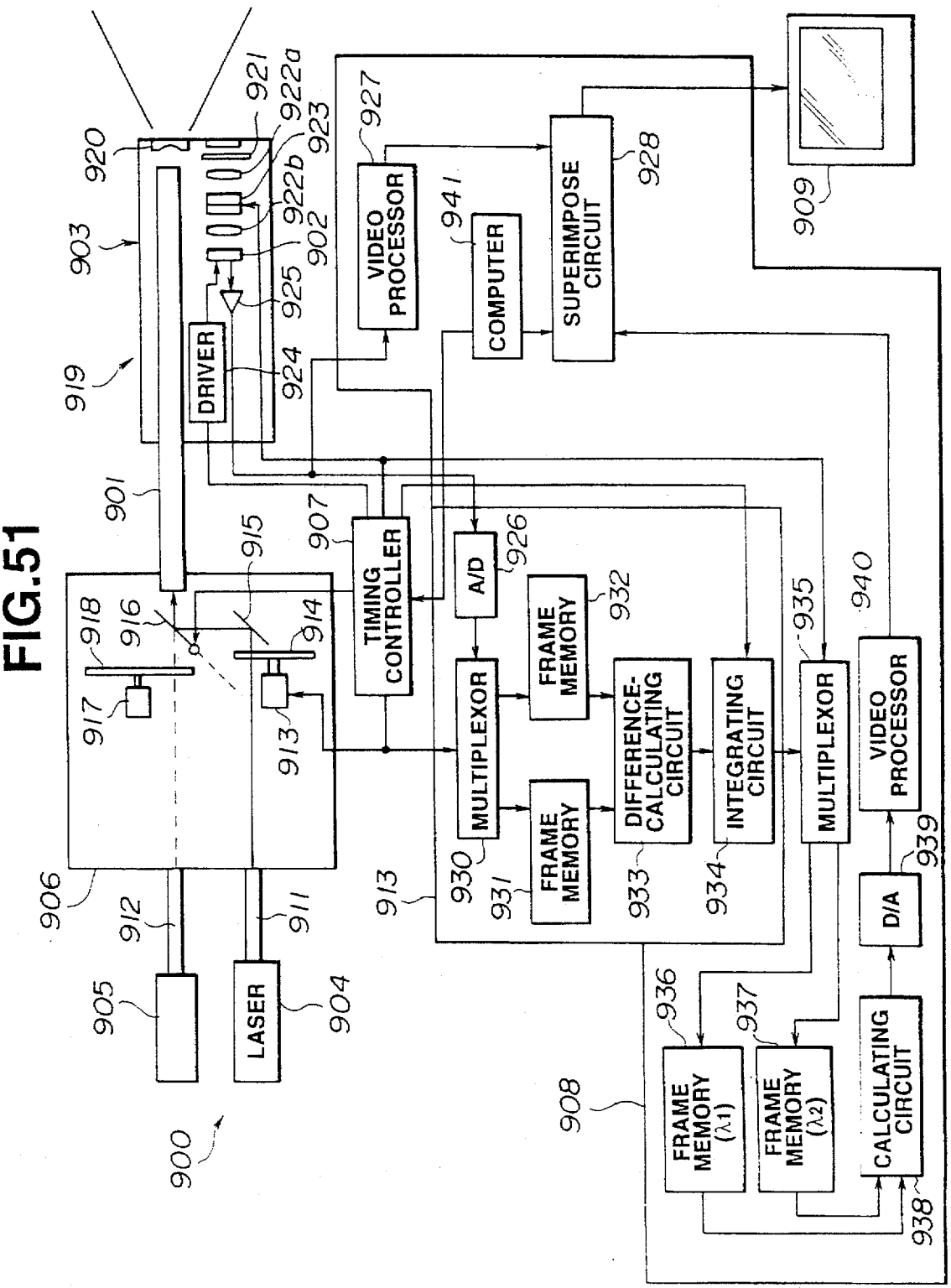
FIG. 51 is a perspective view which illustrates the structure of the fluorescent endoscope apparatus having the electronic endoscope.

As shown in FIGS. 50 and 51, a fluorescent endoscope apparatus 900 comprises a light guide 901 for transmitting light for use to irradiate subject portion to be observed; an electronic endoscope 903 including a solid-state image sensing device 902 for capturing an image obtained from light transmitted through the light guide 901 and used to irradiate the subject portion to be observed; a fluorescent observation light source apparatus 904 for emitting excitation light for performing fluorescent light observation; a normal observation light source apparatus 905 for emitting normal light for performing the normal endoscope observation; an introduced-light switching apparatus 906 for selectively introducing normal light emitted by the normal observation light source apparatus 905 or excitation light emitted by the fluorescent observation light source apparatus 904 into the light guide 901 of the endoscope 903; a timing controller 907 for synchronously controlling an image obtained by irradiating the subject portion to be observed with normal light or excitation light and formed on the solid-state image sensing device 902 and light introduced from the introduced-light switching apparatus 906 into the light guide 901 of the electronic endoscope 903; an image processing portion 908 synchronously controlled by the timing controller 907 and arranged to form the normal light image formed on the solid-state image sensing device 902 of the electronic endoscope 903 into video data for the normal observation and form the fluorescent image formed on the solid-state image sensing device 902 and obtained from excitation light into video data with which fluorescent diagnosis to determine whether or not the subject portion to be observed is a healthy portion can be performed; and a monitor 909 for simultaneously, or in a time-divided manner, displaying the normal observation and fluorescent observation video data processed by the image processing apparatus 908. Note that observation light emitted by the fluorescent observation light source apparatus 904 and the normal observation light source apparatus 905 are introduced into the introduced-light switching apparatus 906 through a light guide cable 911.

As shown in FIG. 51, in the introduced-light switching apparatus 906 of the fluorescent endoscope apparatus 900, excitation light emitted by the fluorescent observation light source apparatus 904 is, through a chopper 914 which is rotated by a motor 913, converted into pulse beams. Then, the pulse beams are reflected by a mirror 915 and the mirror surface of a rotative mirror 916 having, on the rotative surface thereof, a mirror portion and a transmissive portion (designated by dashed line shown in FIG. 51) so as to be made incident on the end of the light guide 901 adjacent to the hand of an operator. The rotation of the rotative mirror 916 is controlled by the timing controller 907.

Light emitted by the normal observation light source apparatus 905 is allowed to pass through an RGB rotative filter 918, which is rotated by a motor 917 and disposed on the optical path, and is allowed to pass through a transmissive portion at the timing (of the rotative mirror 916) when it reaches the optical path. Then, light is made incident on the light guide 901 at a position adjacent to the hand of the operator.

Light made incident on the light guide 901 at a position adjacent to the hand of the operator is introduced into the body cavity into which an insertion portion 919 is inserted. Then, light is transmitted from the leading surface and is allowed to pass through an irradiation lens 920 so that the subject portion to be observed is irradiated with light.

A fluorescent image and a normal image generated due to light with which the subject portion to be observed has been irradiated are allowed to pass through a cover glass attached to an observation window formed at the leading portion of the endoscope 903, a polarizing plate 921, a first objective lens 922a, a liquid crystal filter 923 and a second objective lens 922b to be formed on the solid-state image sensing device 902 so as to be photoelectrically converted.

The image sensing device 902 is operated in response to a drive signal supplied from a driver 924 so that a photography signal photoelectrically converted by the image sensing device 902 is amplified by a pre-amplifier 925. Then, the amplified signal is supplied to an A/D converter 926, which constitutes a two-dimensional lock-in amplifier 913, and a video processor 927 disposed in the image processing apparatus 908.

The video processor 927 processes a photography signal obtained due to the normal light irradiation such that it generates standard video data and causes a normal image to be displayed on the monitor 909 through a superimpose circuit 928.

On the other hand, a photography signal obtained due to fluorescent light irradiation is converted into a digital signal by the A/D converter 926, and then the converted signal is, through a multiplexor 930, distributed into frame memories 931 and 932 for storing odd frame images and even frame images. Then, image data is allowed to pass through a difference-calculating circuit 933 for calculating the difference between images and an integrating circuit for integrating the output denoting the result of the calculation for obtaining the difference. Then, the image data is supplied to a multiplexor 935 in the image processing apparatus 908.

Signals selected by the multiplexor 935 are temporarily stored in frame memories 936 and 937. Two signals read from the frame memories 936 and 937 are calculated by a calculating circuit 938 so as to be signals corresponding to the discriminated state of the texture. Then, the signals are converted into analog signals by a D/A converter 939, and then standard video data is made by a video processor 940, and video data is transmitted to the superimpose circuit 928.

If a determination has been made that the subject portion to be observed is a diseased portion, a fluorescent image is, in the form of a specific color signal, transmitted to the superimpose circuit 928. The fluorescent image is, while being superimposed, displayed or is subjected to a superimpose process to position the normal image and the fluorescent image side-by-side to simultaneously display the two images. Note that a computer 941 controls the timing controller 907 and the superimpose circuit 928.

The fluorescent endoscope apparatus 900 enables a fluorescent image to be displayed in addition to the normal endoscope image by using the electronic endoscope 903. Furthermore, a region having a diseased texture can be displayed in such a manner that it be can easily identified.

Therefore, a significantly effective means to perform screening of a diseased portion, such as an initial-stage cancer, can be provided. The rotative mirror 916 may be manufactured by plating or evaporating aluminum or the like, which is capable of serving as a mirror, onto the light-shielding portion of, for example, the rotative shutter 916. Another structure may be employed in which a mirror is provided for a plunger and the plunger is operated at a predetermined period to introduce/remove the mirror to and from the optical path. The mirror may be reciprocated by a predetermined angular degree to introduce/remove the mirror to and from the optical path.

Furthermore, a foot switch or the like may be provided so as to perform switching between a case in which excitation light and normal light are, by a mirror, sequentially introduced into the light guide 901 in a time-divided manner and a case in which either light is selectively manually introduced to enable the fluorescent light observation to be performed if necessary. The other operations and effects are the same as those of the foregoing embodiments.

Figure 52:
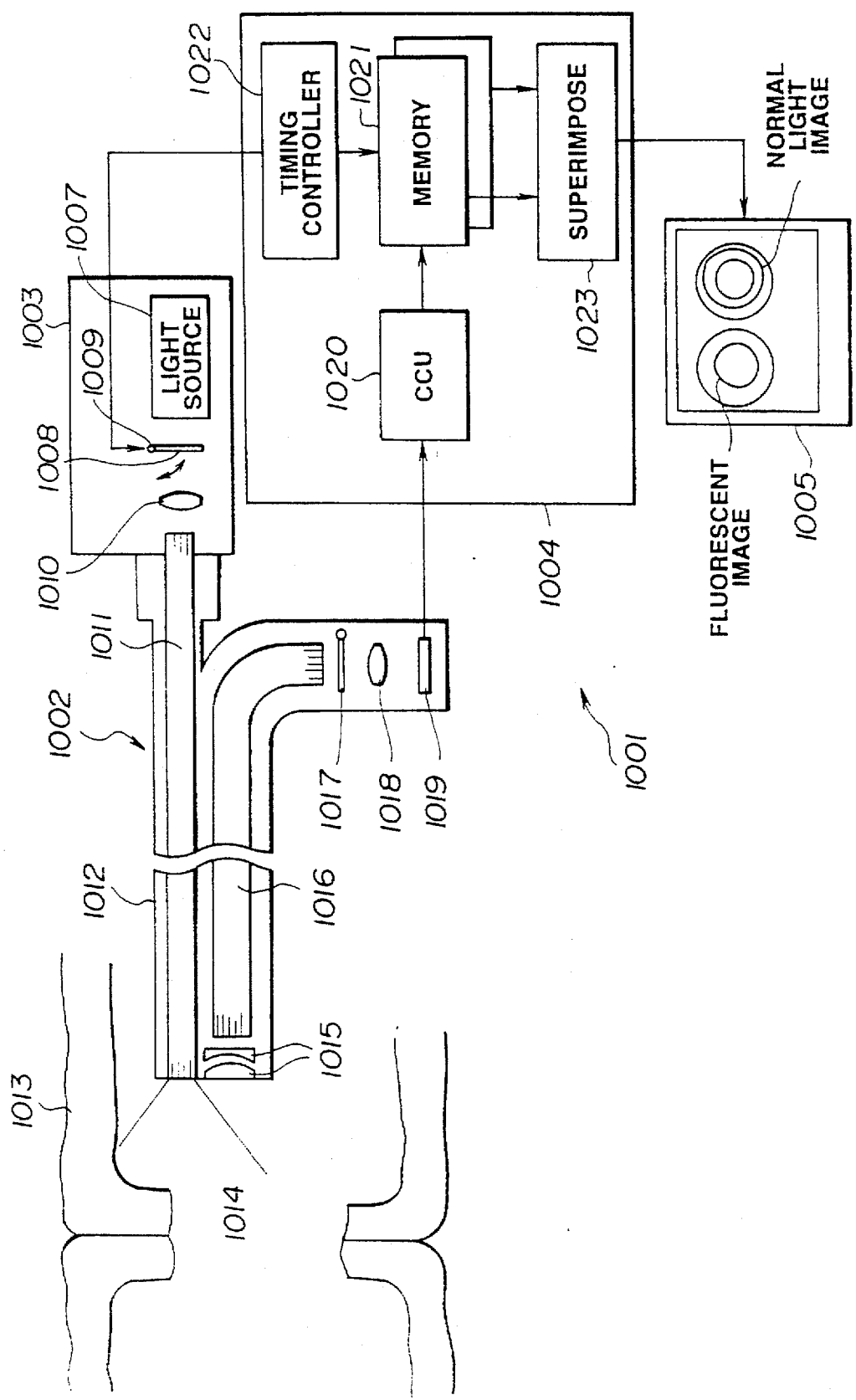
FIG. 52 illustrates a fluorescent endoscope system suitable to diagnose a state of metabolism in a suture portion.
Figure 53:
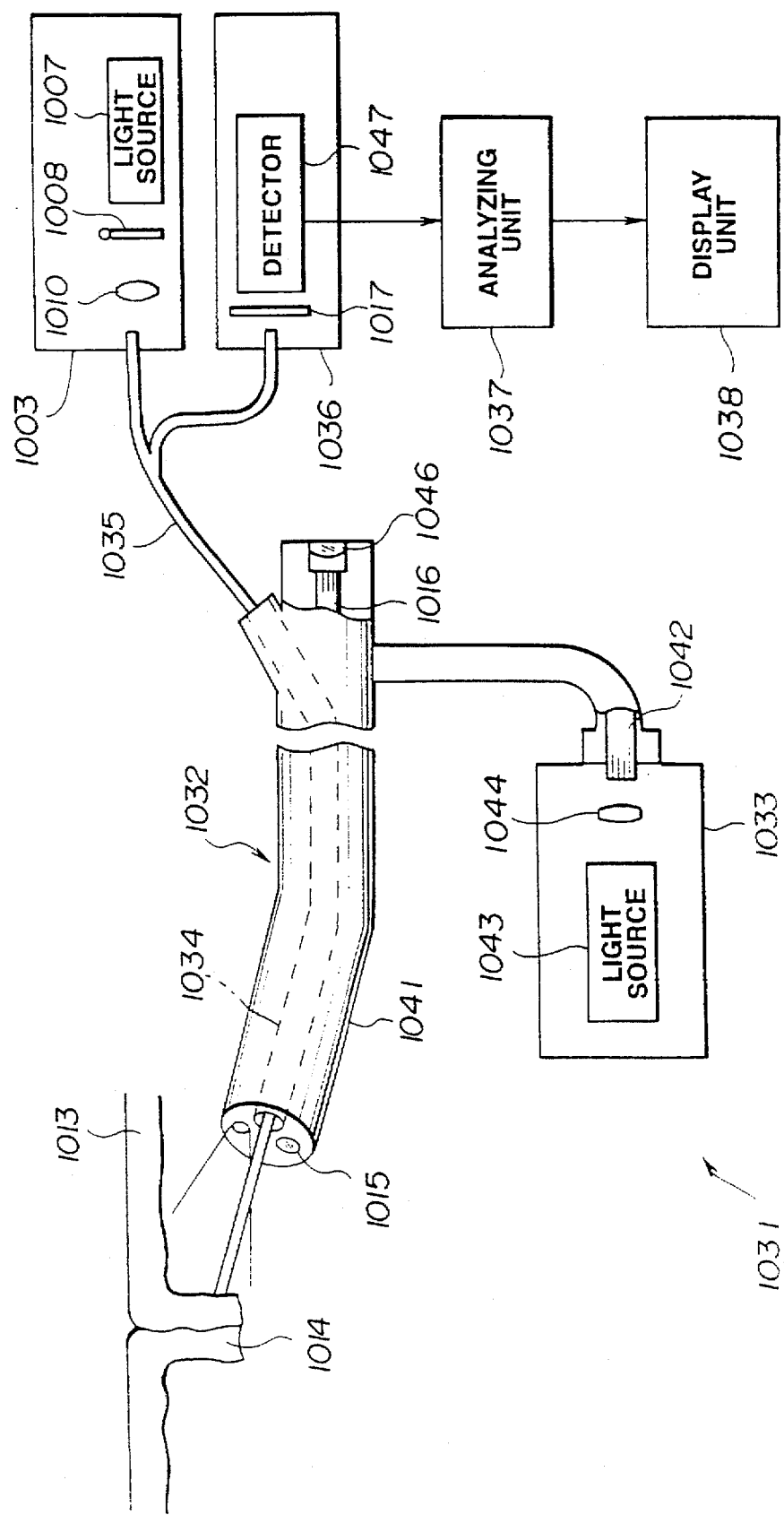
FIG. 53 illustrates a modification of FIG. 52.

FIGS. 52 and 53 illustrate an example of use of the fluorescent endoscope apparatus according to the first, second and third embodiments, in which a portion of the intestinum crassum, from which sigmoid colon has been exsected, is inosculated. It is important to know the metabolism in the inosculated portion for the purpose of preventing a failure in suture. NADH contained in a texture of an organism is a substance that causes oxygen metabolism to be performed. By observing fluorescent light of NADH, a state of metabolism in the suture portion can be diagnosed. FIGS. 52 and 53 illustrate an example for measuring NADH to achieve the foregoing object.

Referring to FIG. 52, the example will now be described.

A fluorescent endoscope system 1001 comprises an endoscope 1002, a light source apparatus 1003, a signal processing apparatus 1004 and a monitor 1005.

The light source apparatus 1003 includes a white light source 1007 that has an irradiation optical path on which a band-pass filter 1008 through which light for excitation NADH is allowed to pass through is disposed, the band-pass filter 1008 being enabled to be retracted when, for example, a motor 1009 is rotated. A condenser lens 1010 is disposed in front of the band-pass filter 1008 to supply normal light to an end surface of a light guide 1011 to be attached to the light source apparatus 1003 at a position adjacent to the hand of an operator.

A light guide 1011 provided for the endoscope 1002 is inserted into a soft insertion portion 1012 to transmit white light or excitation light which is emitted forwards through the leading surface of the light guide 1011 attached to an irradiation window at the leading portion of the insertion portion 1012. Thus, for example, a suture portion 1014 of the intestinum crassum 1013 is irradiated with light.

Reflected white light or fluorescent light is, by an objective lens 1015 attached to the observation window at the leading portion, imaged on the leading surface of an image guide 1016 disposed on the focal point surface. The image guide 1016 transmits a fluorescent image or a reflected light image to the rear end surface of the image guide 1016 at a position adjacent to the hand of the operator.

A cut filter 1017 for cutting excitation light, an imaging lens 1018 and a CCD 1019 are sequentially disposed at positions facing the rear end surface of the image guide 1016. A signal photoelectrically converted by the CCD 1019 is supplied to a CCU 1020 in the signal processing circuit 1004 so as to be converted into video data. The CCU 1020 has a function of each of the two-dimensional lock-in amplifiers 150 and 913 shown in FIGS. 11 and 51.

The signal processing circuit 1004 comprises the CCU 1020, a memory 1021 for storing video data transmitted by the CCU 1020, a fluorescent image and a normal image, a timing controller 1022 for transmitting a timing control signal for controlling opening/closing of the band-pass filter 1008 which separates the fluorescent image and the normal image to be supplied to the memory 1021, and a superimpose circuit 1023 for synthesizing the two images.

Since the operation of the fluorescent endoscope system 1001 is the same as the fluorescent endoscope apparatus according to the foregoing embodiments, its description is omitted. Its effect is also similar to the embodiments above and the fluorescent endoscope system 1001 can be similarly applied to a hard endoscope as well as to the soft endoscope.

The fluorescent endoscope system 1031 shown in FIG. 53 will now be described. This example is intended not to obtain a fluorescent image but has an arrangement that an optical probe inserted into a channel of an endoscope and arranged to introduce light is brought into contact with a suture portion to measure the metabolism of the contact portion by means of fluorescent light of NADH.

The endoscope system 1031 comprises an endoscope 1032, a light source apparatus 1033 for supplying to the endoscope 1032, white irradiation light, a light-introducing probe 1035 inserted into a channel 1034 of the endoscope 1032, a second light source apparatus 1003 for supplying excitation light to the light-introducing probe 1035, a detection apparatus 1036 for detecting fluorescent light introduced through the light-introducing probe 1035, an analyzing apparatus 1037 for obtaining metabolism from fluorescent light detected by the analyzing apparatus 1036, and a display apparatus 1038 for displaying the result of the analysis.

The endoscope 1032 has an elongated and soft insertion portion 1041 into which a light guide 1042 is inserted. An end of the light guide 1042 adjacent to the hand of an operator is connected to the light source apparatus 1033 so that white light emitted by a white light source 1043 is supplied through a condenser lens 1044. White light is emitted forwards through an irradiation window formed at the leading portion of the insertion portion 1041 so that, for example, a suture portion 1014 of the intestinum crassum 1013 is irradiated with light.

Light reflected by the suture portion 1014 is, by the objective lens 1015 attached to the observation window, imaged on the leading surface of the image guide 1016 disposed on the focal point surface of the objective lens 1015. Light is transmitted through the image guide 1016 to the rear end surface of the same so that the suture portion 1014 can be observed with the naked eye through an ocular lens 1046.

The portion of the light-introducing probe 1035 inserted into the channel 1034 of the endoscope 1032 adjacent to the hand of the operator is divided into two pieces, either of which is connected to the light source apparatus 1003 and a residual one of which is connected to the detection apparatus 1036.

The light source apparatus 1003 has the same structure as that shown in FIG. 52 to introduce excitation light so as to emit excitation light through a leading surface projecting over an outlet at the leading portion of the channel 1034 toward the suture portion 1014 which is in contact with the leading surface. Excitation light obtained from the suture portion 1014 is introduced into the portion adjacent to the hand of the operator by the light-introducing probe 1035, and is detected by a detector 1047 through the cut filter 1017 for cutting excitation light. The quantity of detected excitation light is analyzed by the analyzing apparatus 1037 and the result of the analysis is displayed on the display apparatus 1038.

Near infrared light may be used to measure cytochrome or to measure the bloodstream by a laser Doppler meter as well as NADH to obtain the metabolism.

Note that the foregoing embodiments may partially be combined with each other to constitute another embodiment.

A schematic structure of an apparatus for reducing the size of the means of the fluorescent endoscope apparatus having an electronic endoscope for amplifying a fluorescent image will now be described.

Figure 54:
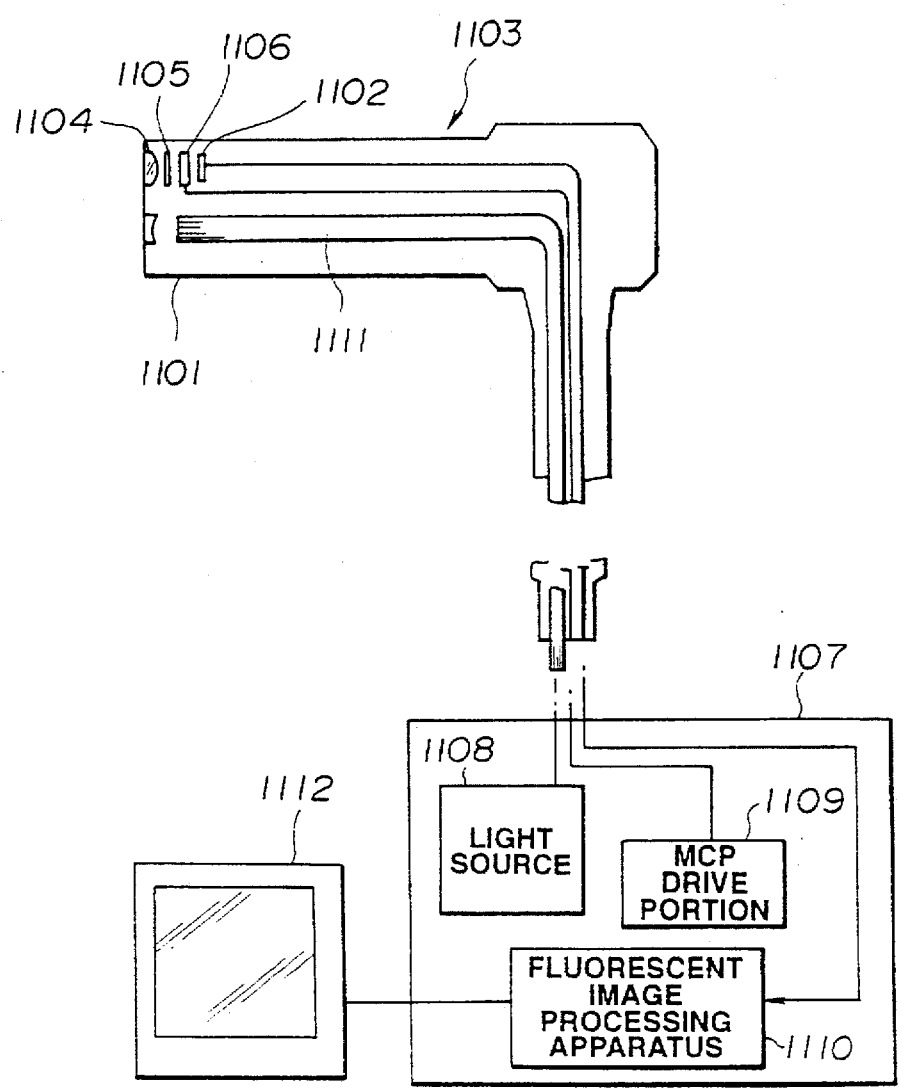
FIG. 54 illustrates a structure in which an amplifying means is disposed on the leading surface of an image sensing device of the electronic endoscope.

As shown in FIG. 54, an electronic endoscope 1103 according to this example comprises an insertion portion 1101 which has a CCD 1102. A filter 1105, an MCP 1106 and a CCD 1102 are disposed in the rear of an objective optical system 1104 of an insertion portion 1101 of the endoscope 1103. An observation apparatus 1107, to which the endoscope 1103 is connected, comprises a light source 1108 for emitting excitation light, an MCP drive portion 1109 for operating the MCP 1106 and a fluorescent image processing apparatus 1110 for processing a fluorescent image signal. Thus, excitation light emitted by the light source 1108 is made incident on a light guide 1111 of the endoscope 1103. Furthermore, a fluorescent image obtained by the endoscope 1103 is signal-processed so as to be, as an image signal, transmitted to a monitor 1112. Thus, a fluorescent image to be observed is displayed.

As described above, the filter, MCP, the CCD and the like may be provided in the leading portion of the insertion portion of the endoscope while obtaining a fluorescent image having desired brightness by the endoscope. Therefore, the size of the apparatus can be reduced and the operationality can be improved.

When the fluorescent endoscope apparatus is constituted, the following constitution of the introduced-light switching apparatus will cut the cost of the fluorescent endoscope apparatus: a fluorescent observation light source apparatus, a fluorescent-light camera, a camera switch unit, and an image processing unit for fluorescent light can be purchased later in addition to the normal endoscope apparatus.

Figure 55:
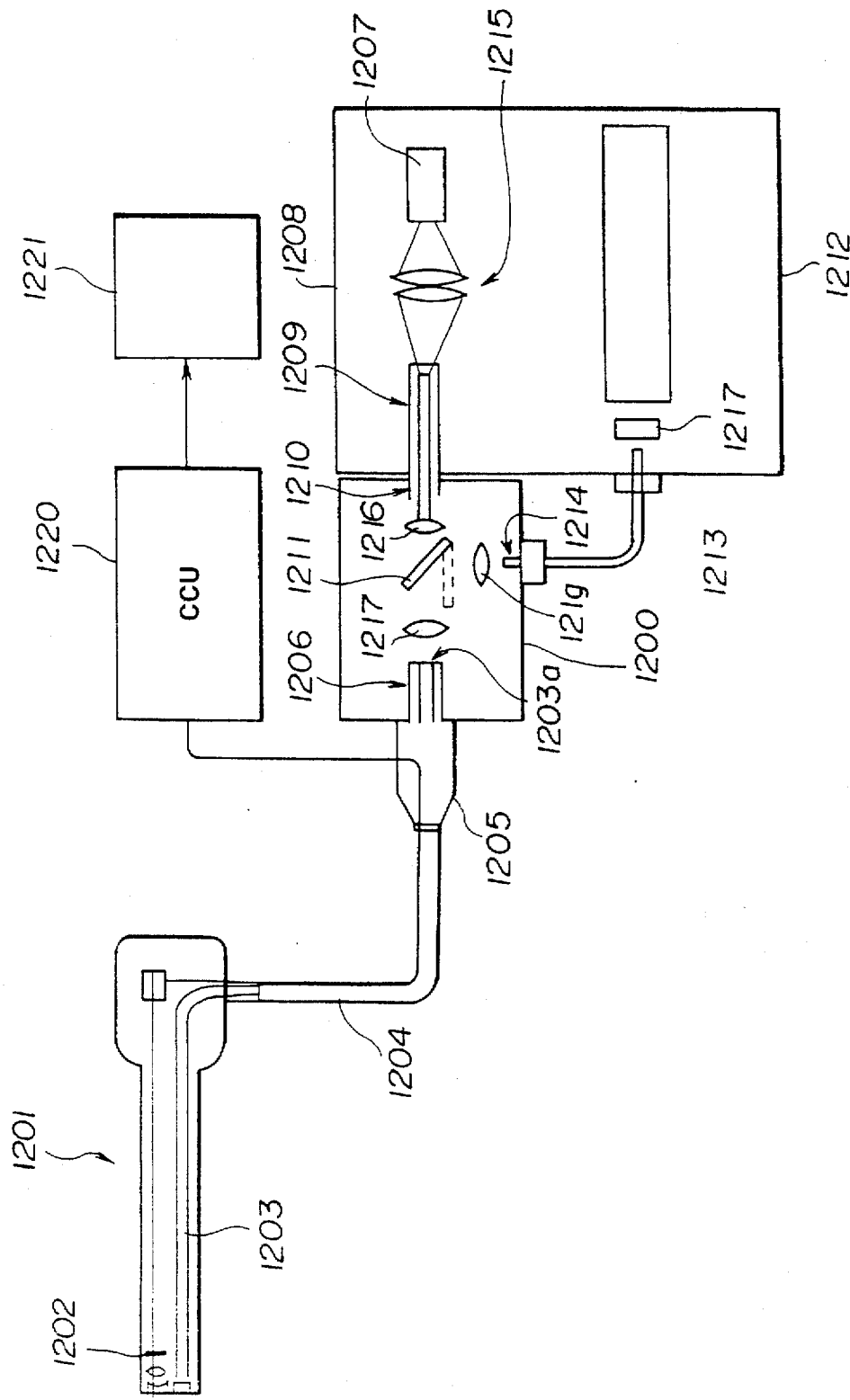
FIG. 55 illustrates the structure of an introduced-light switching apparatus.

An introduced-light switching apparatus 1200 according to this example is, as shown in FIG. 55, adapted to an endoscope 1201 including a CCD 1202. The introduced-light switching apparatus 1200 comprises: a light guide connector receiver 1206, to which a light guide connector 1205 is connected, the light guide connector 1205 being disposed at an end, adjacent to the hand of the operator, of a universal cord 1204 inserted into a light guide 1203 extending from the endoscope 1202; and a convex-shape transmission connector 1210 which can be connected to a light guide connector receiver 1209 of a normal observation light source apparatus 1208 including a xenon lamp 1207, the transmission connector 1210 being composed of a relay lens or the like. The light guide connector 1209 and the transmission connector 1210 are disposed such that their optical axes coincide with one another.

A switch mirror 1211 is disposed on an optical axis connecting the light guide connector receiver 1209 and the transmission connector 1210 to each other, the switch mirror 1211 being disposed in such a manner that it is rotated by a driver (not shown) at a position making an angle of 45° or in parallel to the optical axis that connects the light guide connector receiver 1209 and the transmission connector 1210 to each other.

The introduced-light switching apparatus 1200 has a connection port 1214 for a transmission light guide 1213 extending from the fluorescent observation light source apparatus 1212, the connection port 1214 being formed at a position perpendicular to the optical axis connecting the light guide connector receiver 1209 and the transmission connector 1210 to one another and as well as on the optical path for the switch mirror 1211.

When the switch mirror 1211 is at a position in parallel to the optical axis which connects the light guide connector receiver 1209 and the transmission connector 1210 to each other, normal light emitted by the normal observation light source apparatus 1208 is allowed to pass through an optical lens 1215, the transmission connector 1210 and an optical lenses 1216 and 1217 so as to be converged onto an end surface 1203a of the light guide 1203 extending from the endoscope 1201.

When the switch mirror 1211 is at a position making an angle of 45° from the optical axis, excitation light emitted by the fluorescent observation light source apparatus 1212 is allowed to pass through a shutter 1217, the transmission light guide 1213 and an optical lens 1218. Then, excitation light is reflected by the switch mirror 1211, allowed to pass through the optical lens 1217 and converged onto the light guide end surface 1203a. Note that reference numeral 1220 represents a CCU for forming a photography signal into video data, and reference numeral 1221 represents a monitor for displaying video data generated by the CCU 1220.

As described above, the introduced-light switching apparatus comprises: the light guide connector receiver to be connected to the light guide connector provided for the light guide extending from the endoscope; and the transmission connector which can be connected to the light guide connector receiver for the normal observation light source apparatus. Therefore, normal light emitted by the normal observation light source apparatus can be introduced into the light guide of the endoscope through the introduced-light switching apparatus without the need for changing the structure of the conventional normal observation light source apparatus.

By providing, for the introduced-light switching apparatus, the connection portion, to which the transmission light guide extending from the fluorescent observation light source apparatus is connected and the switch mirror, normal light or excitation light can be selectively introduced into the light guide of the endoscope.

In a case where the fluorescent endoscope apparatus according to the first, second or the third embodiments is used to observe, with fluorescent light, a subject portion to be observed, such as the intestine having a rough surface on the texture thereof, the rough surface of the organism texture cannot uniformly be irradiated with excitation light. Fluorescent light generated by the organism texture cannot uniformly be received. Therefore, the fluorescent observation cannot be performed accurately. Since the internal organ, such as the liver, having no space therein (hereinafter expressed as the "solid organ") has no space between the organism texture and the endoscope, the subject portion to be observed cannot be observed with fluorescent light because fluorescent light generated by the organism texture irradiated with excitation light cannot be received.

Accordingly, a space forming means is provided for the endoscope in order to stably and accurately perform fluorescent observation of a subject portion to be observed by making uniform the irradiation of the organism texture of the subject portion to be observed that has a rough surface or a solid organ and by uniformly receiving fluorescent light generated by the organism texture.

Figure 56:
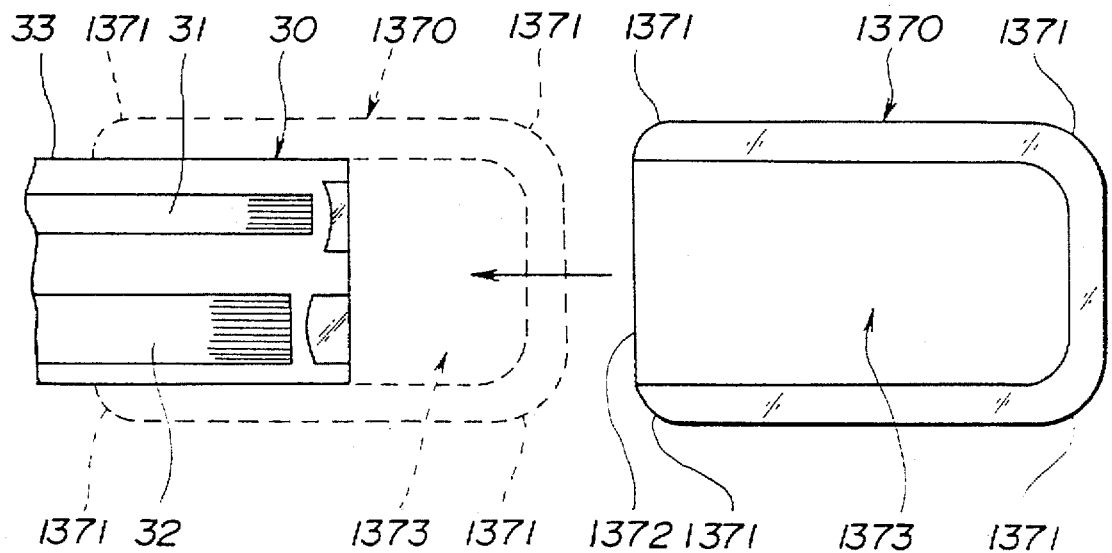
FIG. 56 illustrates a space forming means to be provided in the leading portion of the endoscope.

A transparent cover 1370 serving as the space forming means is, as shown in FIG. 56, a cylindrical cover attached to the leading portion of the insertion portion of the endoscope 30 and permitting excitation light and fluorescent light to pass through so as to cause excitation light introduced through the light guide 31 of the endoscope 30 to be applied to the subject portion to be observed and cause a fluorescent image obtained from excitation light to be made incident on the image guide 32. The transparent cover 1370 has a space portion 1373 for forming a space between the leading portion of the endoscope 30 and the subject portion to be observed. The transparent cover 1370 is made of, for example, sapphire glass, quartz glass, optical material such as BK-7 or transparent resin such as methacrylic resin or polycarbonate resin that has excellent transmissivity with respect to excitation light and fluorescent light.

In order to protect the subject portion to be observed from damage when the endoscope 30 having the transparent cover 1370 as designated by a dashed line, as shown in FIG. 56, is inserted/removed to and from the body cavity, a semispherical portion 1371 is formed in the insertion portion of the transparent cover 1370, the leading portion of the insertion portion is formed into a substantially semi-spherical shape or a semi-spherical portion 1371 is formed at the side end of an opening 1372 adjacent to the hand of an operator. In place of the semi-spherical portion 1371, an inclined portion (not shown) may be formed.

The operation of the transparent cover 1370 having the foregoing structure will now be described.

When an inspection is performed by using the fluorescent endoscope apparatus 250 shown in FIG. 18, the reflecting mirror 61 of the introduced-light switching apparatus 60 is brought to the position designated by the dashed line to converge excitation light emitted by the fluorescent observation light source apparatus 50 onto the rear end surface of the light guide to irradiate the subject portion to be observed.

Then, the endoscope 30 is inserted into a position near the subject portion to be observed in the body cavity in the foregoing normal observation state. At this time, the endoscope 30 can be easily inserted into the subject portion to be observed as a result of the semispherical portion 1371 formed in the leading portion of the transparent cover 1370 without damage to the texture.

Figure 57:
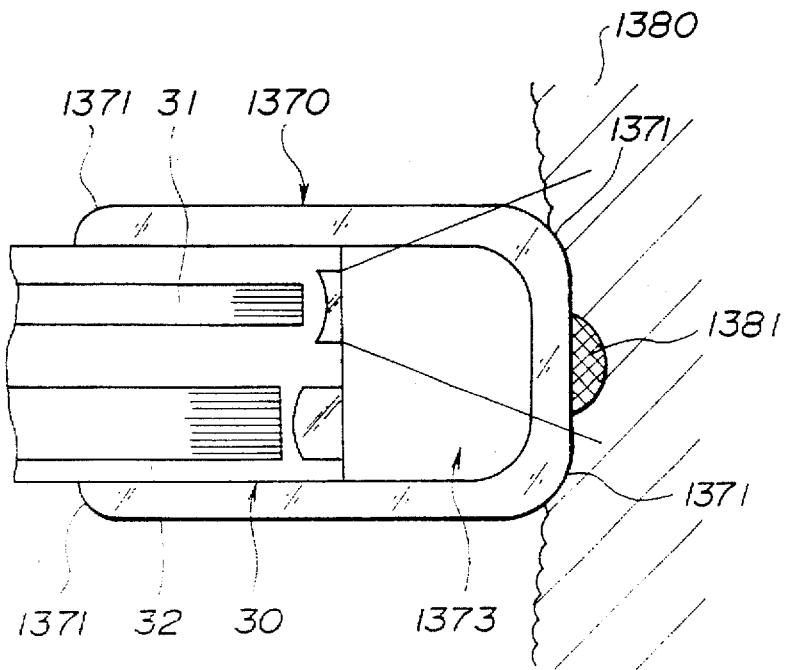
FIG. 57 illustrates a state where an observation is being performed with an endoscope having a transparent cover.

Then, the leading surface of the transparent cover 1370 attached to the leading portion of the insertion portion of the endoscope as shown in FIG. 57 is brought into contact with a body wall 1380. Since the semi-spherical portion 1371 is formed in the leading portion of the transparent cover 1370, the contact with the body wall 1380 can be established without damage to the texture. Therefore, the leading portion of the endoscope 30 can be brought to an optimum position with respect to a subject portion 1381 of the body wall 1380 having a rough surface.

In the foregoing state, the reflecting mirror 61 of the introduced-light switching apparatus 60, the reflecting mirror 281 of the camera switch unit 280 and the video switch circuit 311 are switched to the fluorescent observation side so that excitation light is emitted by the fluorescent observation light source apparatus 50. Thus, excitation light passes through the light guide 31, the space portion 1373 of the transparent cover 1370 and the transparent cover body so that a portion near the subject portion to be observed is irradiated. The body wall 1380 emits fluorescent light. Fluorescent light generated by the body wall 1380 passes through the transparent cover body and the space portion 1373 of the transparent cover 1370 so as to be photographed by the fluorescent-light camera 270 through the image guide 32. Thus, a fluorescent image is displayed on the monitor.

By attaching the transparent cover having the space portion as the space forming means to the leading portion of the endoscope as described above, the transparent cover can be brought into contact with a position near the subject portion to be observed that has a rough surface. Thus, the portion adjacent to the subject portion to be observed can be irradiated uniformly with excitation light. Furthermore, a fluorescent image obtained from excitation light can stably be observed.

Since the gap between the leading surface of the endoscope and the subject portion to be observed can be maintained at a predetermined distance because of the space portion of the transparent cover, fluorescent light generated by the subject portion to be observed can be uniformly received. Thus, the fluorescent observation of the subject portion to be observed which has a rough surface can be stably and accurately performed.

Figure 58:
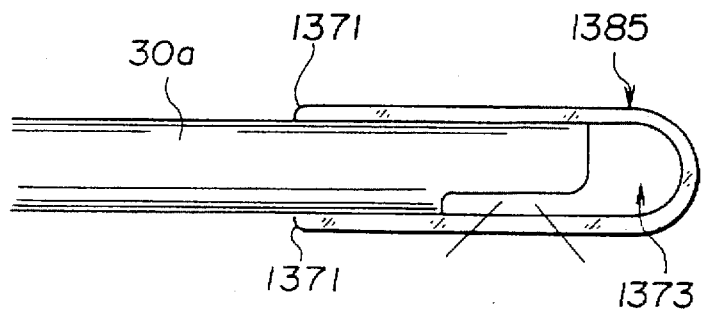
FIG. 58 illustrates a state where the transparent cover is provided for a side-view-type endoscope.
Figure 59:
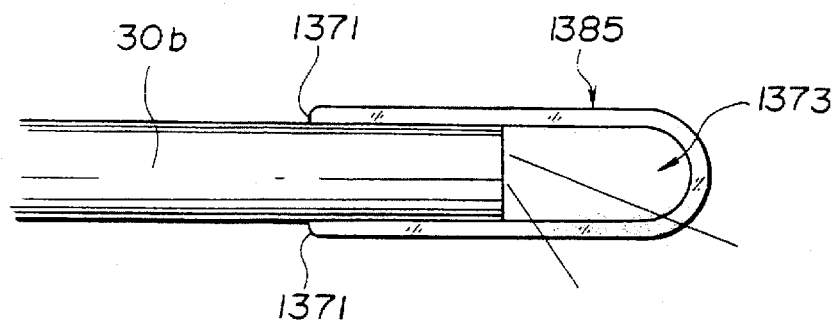
FIG. 59 illustrates a state where the transparent cover is provided for a diagonal-view-type endoscope.

The endoscope, to which the transparent cover is attached, is not limited to a direct-view-type endoscope having the light guide and the image guide on the leading surface thereof. The endoscope may be an electronic endoscope, a side-view-type endoscope 30a arranged as shown in FIG. 58 or a front diagonal-view-type endoscope 30b having the structure as shown in FIG. 59. Each of the side-view-type endoscope 30a and the front diagonal-view-type endoscope 30b has a transparent cover 1385 having a leading surface formed into a semi-spherical shape.

Figure 60:
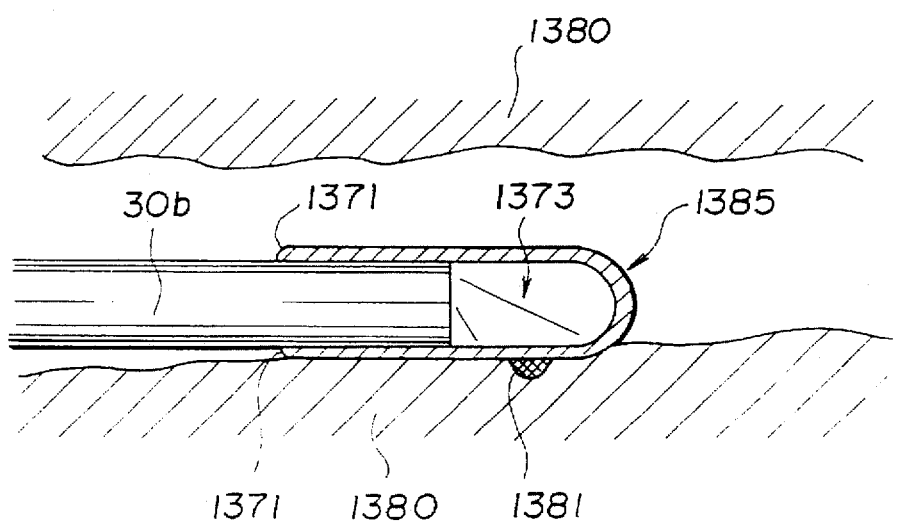
FIG. 60 illustrates a state where an observation is being performed with the diagonal-view-type endoscope having the transparent cover.

As shown in FIG. 60, the side surface of the transparent cover 1385 is brought into contact with the body wall 1380 having a rough surface to observe a subject portion 1381 to be observed so that the fluorescent observation is performed stably and accurately.

Figure 61:
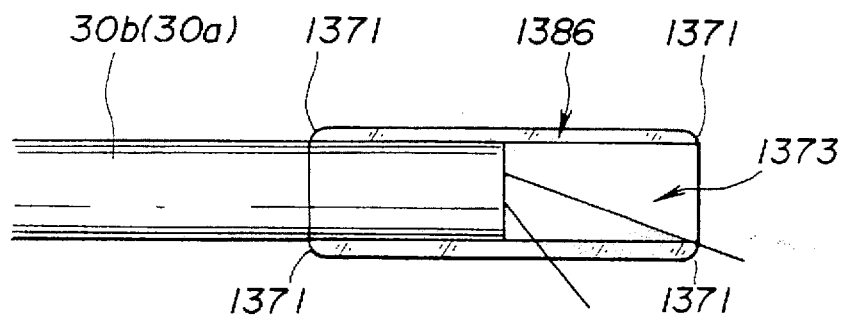
FIG. 61 illustrates a tubular transparent cover.

The space forming means to be attached to the side-view-type endoscope 30a and the front diagonal-view-type endoscope 30b is not limited to the transparent cover 1385. A transparent cover 1386 may be employed which is made of a tubular transparent member having two opening ends as shown in FIG. 61. By bringing the side surface of the transparent cover 1386 to the subject portion to be observed to perform the fluorescent observation, the fluorescent observation of the body wall 1380 having a rough surface can be stably and accurately performed.

Figure 62:
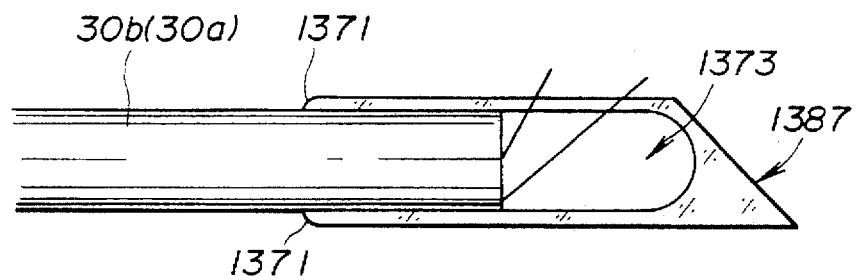
FIG. 62 illustrates a transparent cover having a leading portion that is sharpened so as to be inserted easily.
Figure 63:
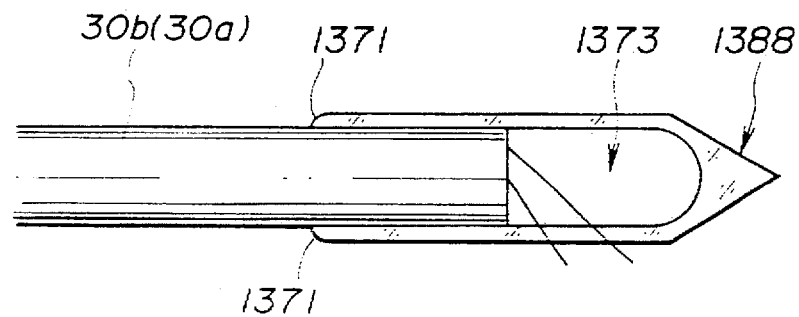
FIG. 63 illustrates another shape of the leading portion of the transparent cover.
Figure 64:
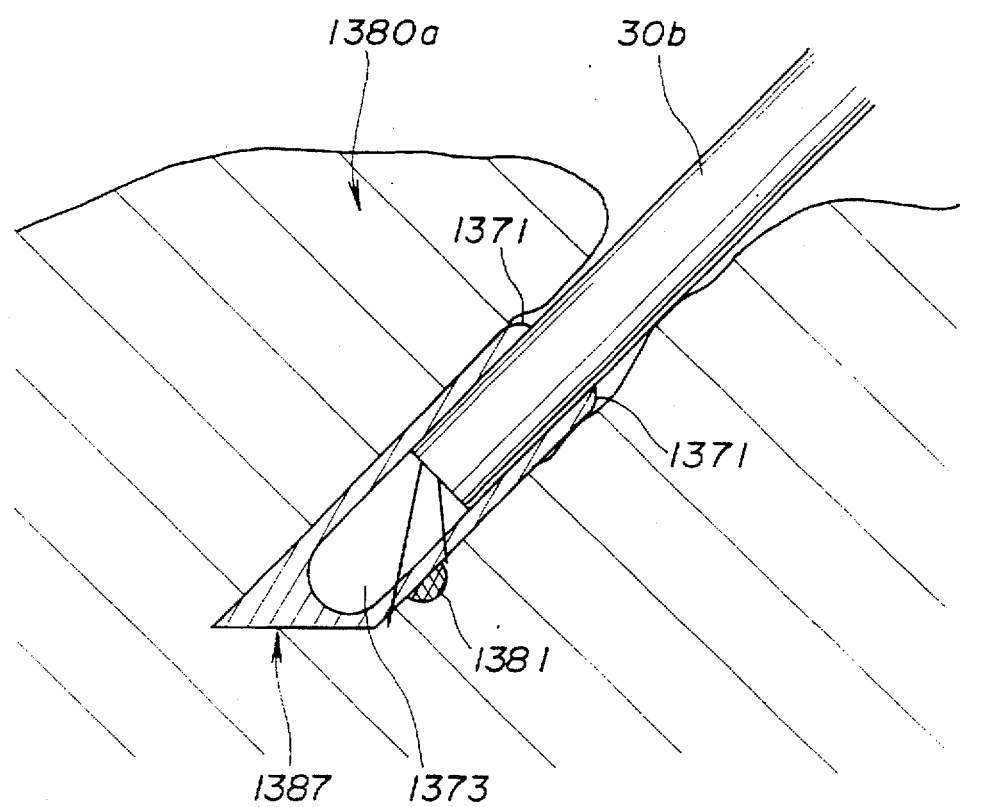
FIG. 64 illustrates a state where an observation is being performed with a diagonal-view-type endoscope having the transparent cover having the sharpened leading portion.

As shown in FIGS. 62 and 63, a transparent cover 1387 or 1388 having a sharpened leading portion may be attached to the leading portion of the side-view-type endoscope 30a or the front diagonal-view-type endoscope 30b. By inserting the leading portion of the transparent cover 1387 or 1388 into a solid internal organ 1380a, a space portion 1373 can be formed between the subject portion to be observed in the internal organ and the leading surface of the endoscope. As a result, the solid internal organ 1380a can be irradiated with excitation light. Furthermore, fluorescent light can be received, and accordingly the fluorescent observation can stably and accurately be performed.

Another example of the space forming means will now be described.

Figure 65:
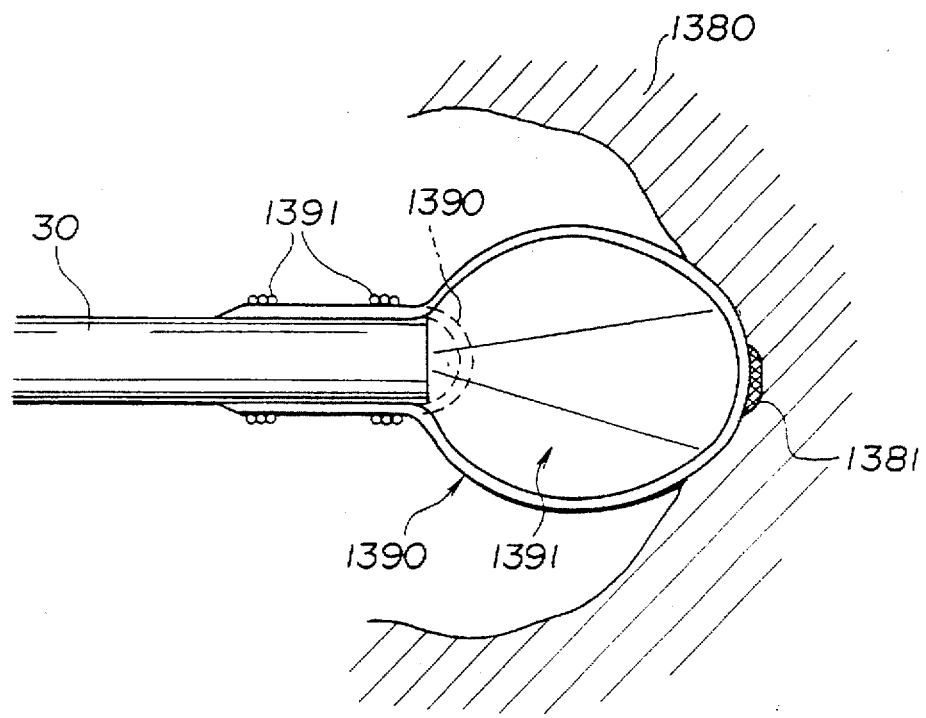
FIG. 65 illustrates a state where an observation is being performed with a straight-type endoscope having a balloon.
Figure 66:
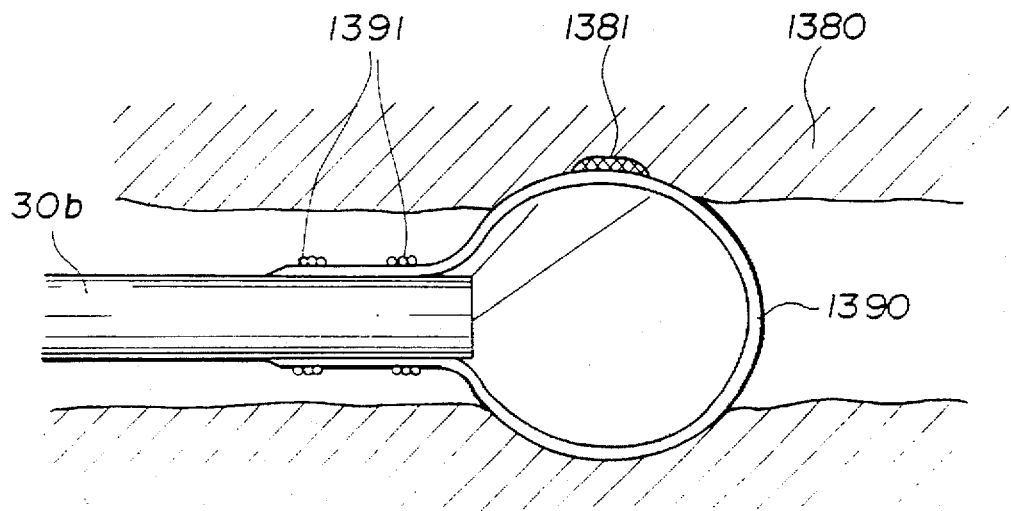
FIG. 66 illustrates a state where an observation is being performed with a diagonal-view-type endoscope having the balloon.

This embodiment has an arrangement that a transparent balloon is, in place of the transparent cover, attached to the leading portion of the endoscope as shown in FIGS. 65 and 66.

As shown in FIG. 65, this embodiment has an arrangement in which a transparent balloon 1390 made of synthetic rubber having excellent transmissivity with respect to excitation light and fluorescent light is attached to the leading portion of the endoscope 30. Reference numeral 1391 represents a thread-wound bonding portion for connecting the transparent balloon 1390 to the leading portion of the endoscope.

The transparent balloon 1390 is, in a normal state, positioned at the leading portion of the endoscope as designated by a dashed line shown in FIG. 65. Therefore, when the endoscope 30 is inserted into the body cavity, the fluorescent endoscope apparatus 250 shown in FIG. 18 is brought to a normal observation state and the endoscope 30 can be inserted into the position near the subject portion to be observed. When the leading portion of the endoscope 30 reaches the position near the subject portion to be observed, a fluid, such as water or air, is injected into the transparent balloon 1390 through a channel (not shown) formed in the endoscope 30 to expand the transparent balloon 1390 as designated by a continuous line shown in FIG. 65. Thus, a portion of the transparent balloon 1390 is brought into contact with the body wall 1380 including the subject portion 1381 to be observed.

In the foregoing state, the reflecting mirror 61 of the introduced-light switching apparatus 60, the reflecting mirror 281 of the camera switch unit 280 and the video switch circuit 311 are switched to the fluorescent observation side to emit excitation light from the fluorescent observation light source apparatus 50. Thus, excitation light is allowed to pass through the light guide 31, the space portion 392 of the transparent balloon 1390, and the transparent balloon 1390. As a result, the portion adjacent to the subject portion to be observed is irradiated with excitation light. As a result, the subject portion to be observed generates fluorescent light. Fluorescent light generated by the subject portion to be observed is photographed by the fluorescent-light camera 270 through the transparent balloon 1390, the space portion 392 and the image guide 32. As a result, a fluorescent image is displayed on the monitor.

Since the transparent balloon for forming the expandable space portion serving as a space portion forming means is disposed in the leading portion of the endoscope as described above, a portion of the transparent balloon is brought into contact with the subject portion to be observed and the portion in the vicinity of the subject portion to be observed can be irradiated with excitation light. Since the distance of the gap from the leading surface of the endoscope to the subject portion to be observed is maintained at a constant distance, fluorescent light generated by the subject portion to be observed can be received uniformly. Thus, the fluorescent observation of a subject portion to be observed that has a rough surface can be performed stably and accurately.

By attaching the transparent balloon 1390 to the front diagonal-view-type endoscope 30b as shown in FIG. 66, it can easily be inserted to reach a position near the subject portion to be observed in the tubular cavity. Furthermore, a portion of the transparent balloon 1390 is brought into contact with the body wall 1380 including the subject portion 1381 to be observed by expanding the transparent balloon 1390. Thus, the fluorescent observation can easily be performed. By expanding the transparent balloon 1390 in the tubular cavity, the body wall 1380 is pressed and thus the quantity of the bloodstream is reduced. Therefore, fluorescent observation can be performed while preventing the influence of the bloodstream.

Since the fluorescent observation involves excessive noise because weak fluorescent light is amplified at a high magnification. Since a pseudo-color display is performed in order to discriminate a tumor portion and a normal portion, a satisfactory stereoscopic view cannot be obtained. Therefore, in a case where forceps for biopsy is used while performing fluorescent observation, the position of the leading portion of the forceps cannot sometimes easily be recognized.

Accordingly, there is a desire for a fluorescent endoscope apparatus with which forceps for biopsy can accurately be positioned with respect to the subject portion to be observed by applying fluorescent paint to the leading portion of the forceps or by constituting the forceps by a substance that emits fluorescent light.

Figure 67:
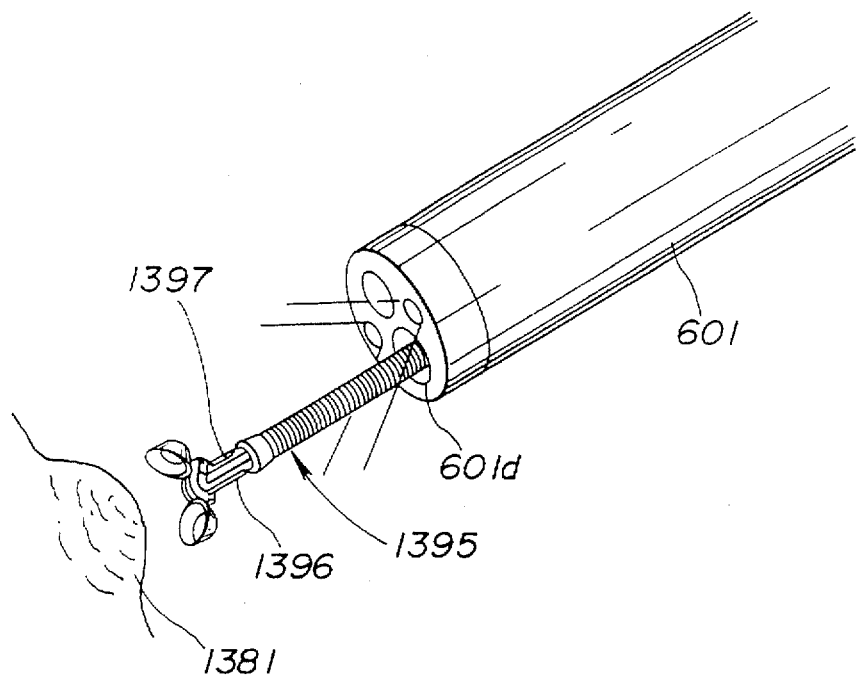
FIG. 67 is a perspective view which illustrates a treatment tool applied with fluorescent paint.

As shown in FIG. 67, forceps 1395 are inserted through, for example, a channel 601d of the endoscope 601 of the foregoing fluorescent endoscope apparatus 600. The leading portion 1396 of the forceps 1395 is applied with fluorescent paint 1397.

Figure 68:
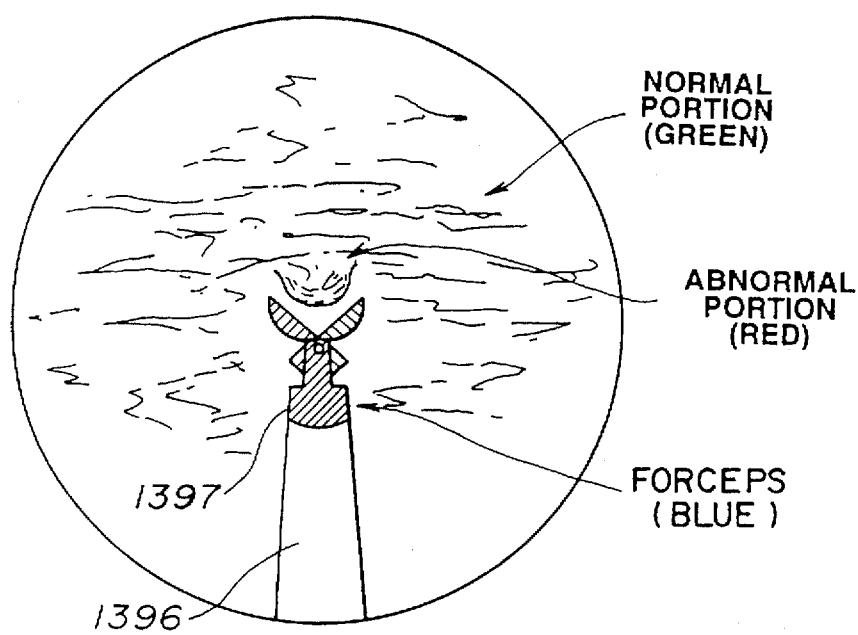
FIG. 68 illustrates fluorescent images of a subject portion to be observed and the treatment tool to be displayed on the monitor.

Therefore, even if the fluorescent observation is being performed, the leading portion 1396 of the forceps 1395 can be detected as shown in FIG. 68. Therefore, the position of the forceps 1395 with respect to the subject portion 1381 to be observed can accurately be recognized. By using the fluorescent paint 1397 to be applied to the leading portion 1396 of the forceps 1395 of a type having different characteristics from those of fluorescent light which is generated by the texture, for example, by making the color of the forceps to be blue with respect to green for the normal portion and red for the abnormal portion when the pseudo-color display is performed, the discrimination can easily be performed.

The fluorescent paint capable of emitting fluorescent light is exemplified by Lumogen, Shannon Glow, Tiglocolor, Cold Fire Color and the like.

A treatment through an endoscope to be performed by using an endoscope to perform a cure and treatment includes a laser beam treatment in which an endoscope probe connected to a curing laser beam source apparatus is, through a channel of an endoscope, inserted to reach an aimed position, and a diseased portion or the like is irradiated with laser beams to perform cauterization, coagulation, perspiration and the like. A laser beam curing apparatus for performing a curing treatment with irradiation with laser beams of the foregoing type comprises a laser beam guide means, such as a laser beam probe, that introduces high-energy curing laser beams, such as Nd:YAG laser beams into a diseased portion to irradiate the portion to be cured so that cauterization, coagulation and perspiration treatments are performed.

Figure 69:
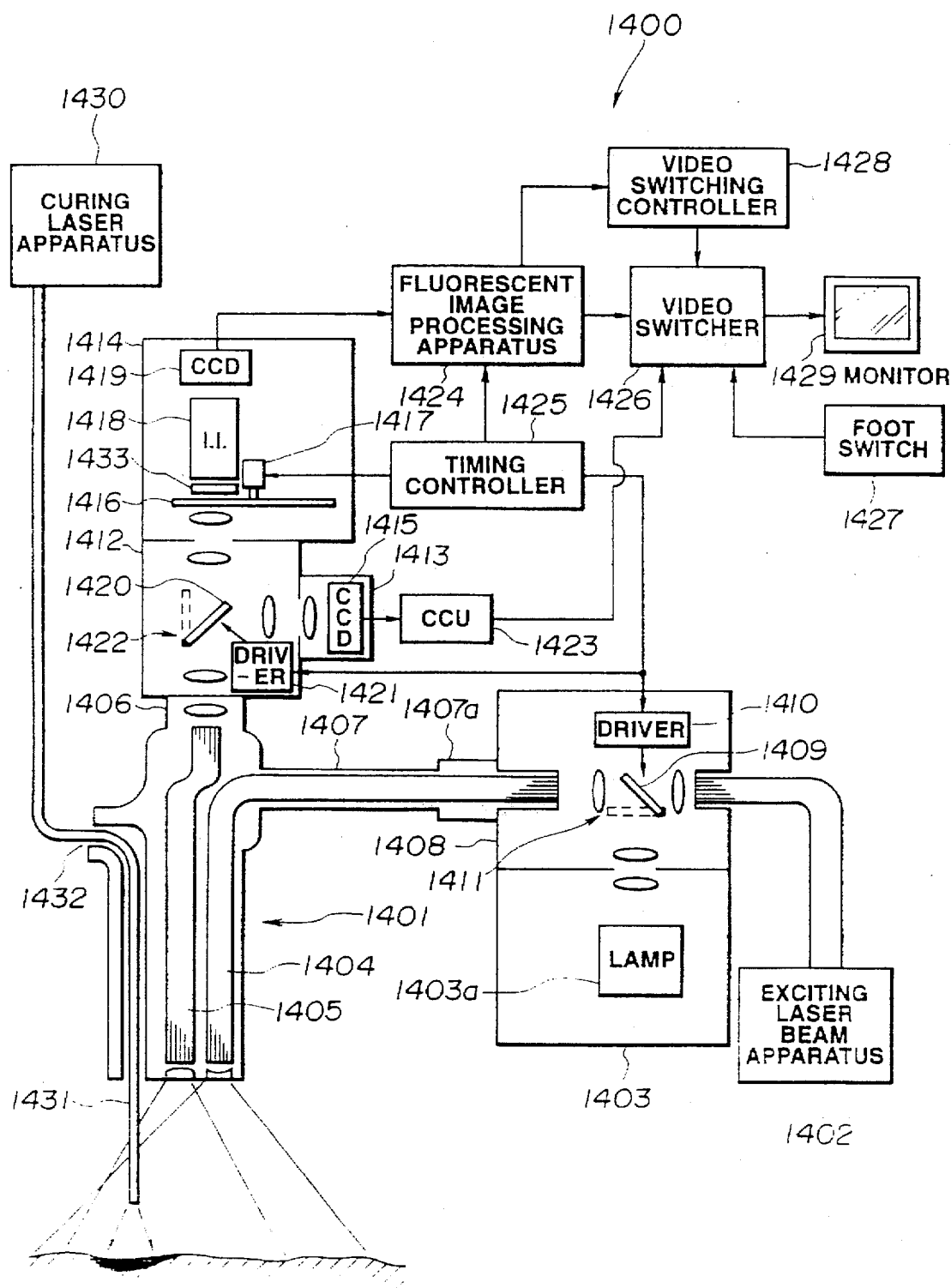
FIG. 69 illustrates the structure of a fluorescent diagnosing and curing endoscope apparatus.

Referring to FIG. 69, an example of a fluorescent endoscope apparatus that is capable of simultaneously performing the fluorescent observation and laser cure will now be described.

A fluorescent light diagnosing and curing apparatus 1400 according to this example comprises an endoscope 1400 for introducing excitation light to a subject portion to be observed and forming a fluorescent light image obtained from the subject portion to be observed. As an excitation light source means for generating excitation light and for use when the fluorescent light observation is performed, the fluorescent light diagnosing and curing apparatus 1400 comprises a fluorescent observation light source apparatus 1402 having a He—Cd (Helium-Cadmium) excitation light generating means for generating violet light having a wavelength of 442 nm. Furthermore, the fluorescent light diagnosing and curing apparatus 1400 comprises a normal observation light source apparatus 1403 having a lamp 1403a for generating normal light as a light source for the normal observation for observing an endoscope image. In addition, a curing laser beam apparatus 1430 is provided which serves as a curing laser beam generating means having a laser beam generating means for generating, for example, infrared Nd:YAG laser beams as curing laser beams having the energy which is capable of treating a diseased portion in the subject portion to be observed.

A laser probe 1431 serving as a laser beam introducing means for transmitting the curing laser beam is connected to the curing laser apparatus 1430 so that the generated laser beam is supplied to the laser probe 1431 to emit the curing laser beam through the leading portion of the laser probe 1431. As the curing laser beam to be generated by the curing laser apparatus 1430, any of laser beams is used which has a different wavelength region from the wavelength of fluorescent light of a fluorescent image obtainable from the irradiation of the subject portion to be observed with the laser beam and which has a wavelength outside the visible region, the laser beams being exemplified by ultraviolet laser, such as an eximer laser, and an infrared laser, such as Ho:YAG laser (having a wavelength about 2 µm) or Er:YAG laser (having a wavelength about 3 µm). In addition to the foregoing laser curing operation, a photochemical treatment (PDT) has been performed, in which light suitable to the PDT, that is, semiconductor laser beam, dye laser beams or alexandrite laser beams, can be used.

The endoscope 1401 includes a light guide 1404 for transmitting light emitted by a fluorescent observation light source apparatus 1402 or a normal observation light source apparatus to the leading portion and an image guide 1405 for transmitting an image to be observed to an ocular portion 1406 disposed at the rear end of the apparatus. The light guide 1404 is allowed to pass through a universal cord 1407 extending from the side portion of a handle portion adjacent to the hand of an operator, the light guide 1404 being extended to reach a light guide connector 1407a disposed at an end of the light guide 1404. The endoscope 1401 has a channel 1432 through which the laser probe 1431 connected to the curing laser apparatus 1430 can be inserted, the channel 1432 extending from the portion adjacent to the hand of the operator to the leading portion of the endoscope 1401. Thus, the laser probe 1431 can be inserted into the channel 1432 to project over the leading portion of the endoscope 1401.

The fluorescent observation light source apparatus 1402 and the normal observation light source apparatus 1403 are connected to the introduced-light switching apparatus 1408 that switches light to be introduced into the endoscope 1401. The light guide connector 1407a of the endoscope 1401 is connected to the introduced-light switching apparatus 1408 so that excitation light emitted by the fluorescent observation light source apparatus 1402 or normal light emitted by the normal observation light source apparatus 1403 is, through the introduced-light switching apparatus 1408, introduced into the light guide 1404 of the endoscope 1401 so as to be emitted through the leading portion of the endoscope 1401.

The introduced-light switching apparatus 1408 comprises an irradiation light switch means 1411 constituted by a movable mirror 1409 disposed in the optical path for light emitted by the fluorescent observation light source apparatus 1402 or the normal observation light source apparatus 1403 and a driver 1410 for operating the movable mirror 1409 so that the angle of the movable mirror 1409 is selectively switched. Thus, excitation light or normal light is introduced to the rear end surface of the light guide 1404 of the endoscope 1401.

A camera switch unit 1412 is connected to the ocular portion 1406 of the endoscope 1401. A normal-light camera 1413 serving as a normal image receiving portion and a fluorescent-light camera 1414 serving as a fluorescent image receiving portion are connected to the camera switch unit 1412. Each of the imaging means captures a normal image and a fluorescent image. The normal-light camera 1413 comprises an imaging optical system and a CCD 1415 serving as an image sensing device so as to capture an image (a normal image) of a subject portion to be observed which has been irradiated with normal light emitted by the normal observation light source apparatus 1403.

The fluorescent-light camera 1414 comprises an imaging optical system, a rotative filter 1416 for permitting a fluorescent component having a wavelength in a predetermined band to pass through, an image intensifier (hereinafter abbreviated to an "I.I.") 1418 for amplifying the image transmitted through the rotative filter 1416, a CCD 1419 for capturing an output image from the I.I. 1418, and a curing laser beam cutting filter 1433 disposed between the rotative filter 1416 and the I.I. 1418 and serving as a filter means for cutting the curing laser beam. Thus, the fluorescent-light camera 1414 photographs a fluorescent image of the subject portion to be observed that can be obtained by the irradiation with excitation light emitted by the fluorescent observation light source apparatus 1402.

The rotative filter 1416 has a band-pass filter for permitting light having a wavelength, for example, $\lambda 1=480$ nm to 520 nm to pass through and a band-pass filter for permitting light having a wavelength, for example, $\lambda 2=630$ mm or longer, the rotative filter 1416 being formed into a disc-like shape. When the rotative filter 1416 is rotated, the foregoing filters are sequentially inserted into the optical path to permit fluorescent light components having the corresponding wavelength band to pass through. As the curing laser beam cutting filter 1433, a ultraviolet cutting filter is used when ultraviolet light is used as the curing laser beam. When infrared excitation light is used, an infrared-ray cutting filter is used. Thus, the wavelength component of the curing laser beam can be filtered (cut) to inhibit passing of the same.

The camera switch unit 1412 comprises a photographing switch means 1422 constituted by a movable mirror 1420 disposed in the optical path for the image of the object that has been transmitted to the ocular portion 1406 of the endoscope 1401 and a driver 1421 for operating the movable mirror 1420. By selectively switching the angle of the movable mirror 1420, the fluorescent-light camera 1414 and the normal-light camera 1413 are switched such that the object image obtained by the endoscope 1401 is introduced into the normal-light camera 1413 or the fluorescent-light camera 1414.

The endoscope 1401, the camera switch unit 1412 and the fluorescent-light camera 1414 constitute a fluorescent collection means.

A camera control unit (a CCU) 1423 is connected to the normal-light camera 1413 so that a photography signal (a normal image signal) which is the output from the CCD 1415 is signal-processed by the CCU 1423. Thus, a video signal of a normal image can be generated.

The fluorescent image processing apparatus 1424 serving as the fluorescent image processing means is connected to the fluorescent-light camera 1414 to receive a photography signal (a fluorescent image signal) which is the output from the CCD 1419. The photography signal is processed by the fluorescent image processing apparatus 1424 so that a video signal of the fluorescent image is generated.

Furthermore, a timing controller 1425 for controlling the operation timing of each unit is provided to transmit a timing signal to each of the driver 1410 of the introduced-light switching apparatus 1408, the driver 1421 of the camera switch unit 1412, the drive motor 1417 of the rotative filter 1416 and the fluorescent image processing apparatus 1424.

The CCU 1423 and the fluorescent image processing apparatus 1424 are connected to a video switcher 1426 serving as an image switching means. A normal image signal, which is the output from the CCU 1423 and which can be obtained by the normal observation means, and a fluorescent image signal, which is the output from the fluorescent image processing apparatus 1424 and which can be obtained by the fluorescent observation means are selectively switched by the video switcher 1426.

A foot switch 1427 for manually controlling the image switching operation and a video switching controller 1428 are connected to the video switcher 1426, the video switching controller 1428 being arranged to detect the quantity of fluorescent light having a wavelength greater than excitation light in accordance with the fluorescent image signal that has been processed by the fluorescent image processing apparatus 1424 to make a signal for identifying a diseased portion to transmit the diseased portion identification signal so as to automatically control switching of the image. A monitor 1429 is connected to the output terminal of the video switcher 1426 so that the fluorescent image signal or the normal image signal selected by the video switcher 1426 is received. Thus, the fluorescent image or the normal image is displayed on the monitor 1429.

When an observation is performed with the fluorescent diagnosing and curing apparatus 1400 according to this example, first an instruction made with the timing control signal supplied by the timing controller 1425 causes the introduced-light switching apparatus 1408 and the camera switch unit 1412 to switch the light source and the camera so that the fluorescent observation state or the normal observation state is selected. At this time, the timing controller 1425 synchronizes the process to be performed in the fluorescent image processing apparatus 1424 and the operations of the movable mirror 1409 of the introduced-light switching apparatus 1408, the movable mirror 1420 of the camera switch unit 1412 and the rotative filter 1416 of the fluorescent-light camera 1414.

The introduced-light switching apparatus 1408 causes the driver 1410 to move the movable mirror 1409 to switch normal light emitted by the lamp 1403a of the normal observation light source apparatus 1403 and the excitation light emitted by the fluorescent observation light source apparatus 1402 to introduce selected light into the light guide 1404 of the endoscope 1401. Light introduced by the introduced-light switching apparatus 1408 is allowed to pass through the light guide 1404 to reach the leading portion of the endoscope 1401 so that the subject portion to be observed and disposed in front of the endoscope 1401 is irradiated with light. A normal image or a fluorescent image obtained from light used to irradiate the subject portion to be observed is, by the image guide 1405 passing through the endoscope 1401, transmitted to the ocular portion 1406 adjacent to the operator.

The camera switch unit 1412 causes the driver 1421 to operate the movable mirror 1420 to switch the camera for transmitting the image supplied from the ocular portion 1406 of the endoscope 1401 so that the normal image is introduced into the normal-light camera 1413 and the fluorescent image is introduced into the fluorescent-light camera 1414.

The object image (the normal image) irradiated with normal light is captured by the CCD 1415 included by the normal-light camera 1413. A photography signal of the normal image is transmitted to the CCU 1423 so as to be signal-processed. Thus, it is, as a normal image signal, transmitted to the video switcher 1426.

The fluorescent image of the subject portion to be observed that can be obtained by the irradiation with excitation light is, in the fluorescent-light camera 1414, subjected to a process of transmitting the fluorescent component having wavelengths $\lambda 1$ and $\lambda 2$ to be performed by the rotative filter 1416. The fluorescent image is optically amplified by the I.I. 1418 and it is captured by the CCD 1419. The photography signal of the fluorescent image is signal-processed by the fluorescent image processing apparatus 1423 so as to be transmitted to the video switcher 1426 as a fluorescent image signal. The fluorescent components having wavelengths $\lambda 1$ and $\lambda 2$ separated by the rotative filter 1416 have different intensities of fluorescent light between a healthy portion and a diseased portion. That is, the healthy portion and the diseased portion cause the fluorescent spectrum intensities to be different from each other. Thus, the signal process performed by the fluorescent image processing apparatus 1424 is able to generate a fluorescent image signal in which the healthy portion and the diseased portion are distinguished from each other.

The normal image and the fluorescent image supplied to the video switcher 1426 are switched in response to the diseased portion identification signal supplied from the video switch controller 1428. If a diseased portion has been detected in the fluorescent image of the subject portion to be observed, the fluorescent image is transmitted to the monitor 1429. In the other cases, the normal image is transmitted to the monitor 1429. Thus, the normal image or the fluorescent image is displayed on the monitor 1429.

Although the video switcher 1426 selects the normal image or the fluorescent image in accordance with the identification signal to transmit the selected image, the image can be switched in accordance with an instruction issued from the foot switch 1427.

A case where the laser beam irradiation cure is performed with the fluorescent diagnosing and curing apparatus according to this example while performing the fluorescent diagnosis will now be described.

The laser probe 1431 connected to the curing laser apparatus 1430 is inserted into the channel 1432 of the endoscope 1401 to project the same over the leading portion of the endoscope 1401. Then, the curing laser beams supplied by the curing laser apparatus 1430 are used to irradiate the aimed portion to be cured, such as a diseased portion. As a result of the irradiation with the laser beams, the portion irradiated with the laser beams is denatured, coagulated or perspirated so that the curing treatment is performed.

In the fluorescent-light camera 1414, the curing laser beam cutting filter 1433 for protecting the I.I. 1418 is disposed in front of the I.I. 1418. Therefore, the components having the wavelength of the curing laser beam is removed by the curing laser beam cutting filter 1433. Thus, damage of the I.I. 1418 by reflected light of the curing laser beam can be prevented. Note that the curing laser beam has a wavelength different from that of the fluorescent image obtainable by excitation light so that influence upon the fluorescent image is prevented.

The curing laser beam emitted through the laser probe 1431 is arranged to a predetermined position of the fluorescent image, for example, on an extension line of the opening portion of the channel 1432 of the endoscope 1401. Note that the leading portion of the laser probe 1431 may have a warp-enabled structure to irradiate a desired portion with the curing laser beam while performing the fluorescent observation.

Since the portion irradiated with the curing laser beams does not emit fluorescent light even if it is irradiated with excitation light, the fluorescent image of the subject portion to be observed is divided into three portions, which consist of a healthy portion, a diseased portion and a portion irradiated with the laser beams (treated portion), depending upon the state of fluorescent light (the intensity of fluorescent spectrum).

In this embodiment, the fluorescent image displayed on the monitor 1429 is displayed in a pseudo-color manner such that the normal portion is displayed in, for example, green, a diseased portion (an abnormal portion due to disease) is displayed in red and a portion irradiated with excitation light and therefore emitting no fluorescent light is displayed in white or black, which is different from the colors for the normal portion and the diseased portion. Therefore, the state of treatment performed by the irradiation with excitation light is displayed on the fluorescent image so that the state of the treatment is easily be recognized. Therefore, the diseased portion can be detected and the laser beam irradiation treatment can be performed while discriminating the diseased portion and the portion to be treated.

As described above, the fluorescent-light camera of the fluorescent diagnosing apparatus is arranged in such a manner that: the curing laser beam cutting filter is disposed in front of the optical path for the image intensifier; and the laser probe is enabled to be inserted into the channel in the fluorescent diagnosing endoscope. Therefore, a cure by means of coagulation, transpiration or the like using the curing laser beam can easily be performed. Furthermore, the normal portion and the abnormal portion can be distinguished from each other in a fluorescent image, and the portion treated and cured by the irradiation of the laser beams is pseudo-color-displayed in a color different from colors of the normal portion and the abnormal portion. Thus, the cured and treated portion can easily be identified. Therefore, the cure and treatment by means of the irradiation with excitation light can reliable and easily be performed while confirming the state of treatment.

Figure 70:
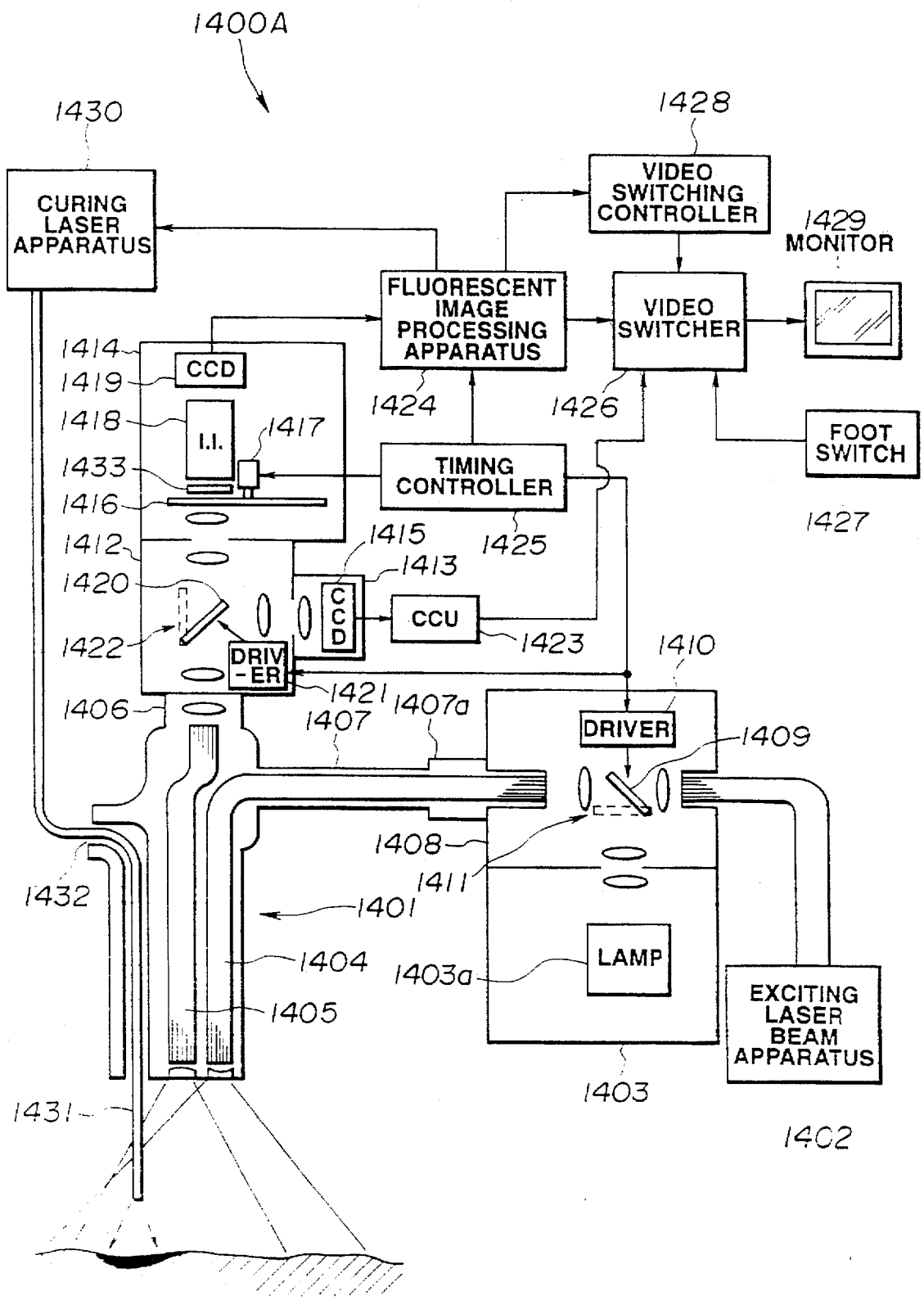
FIG. 70 illustrates another structure of the fluorescent diagnosing and curing endoscope apparatus.

Referring to FIG. 70, another example of a fluorescent diagnosing and curing apparatus that is capable of simultaneously performing the fluorescent observation and the laser treatment will now be described. In this embodiment, a function is provided, which controls the emission of curing fluorescent observation light, in addition to the structure of the apparatus shown in FIG. 69.

That is, a fluorescent diagnosing and curing apparatus 1400A according to this example has an arrangement that the fluorescent image processing apparatus 1424 for processing a photography signal of the fluorescent image photographed by the fluorescent-light camera 1414 is also connected to the curing laser apparatus 1430. Thus, the fluorescent image processing apparatus 1424 transmits a signal for controlling emission of laser beams to the curing laser apparatus 1430. The other structures are the same as those of the first embodiment shown in FIG. 69 and their descriptions are omitted.

Excitation light emitted by the fluorescent observation light source apparatus 1402 is used to irradiate a subject portion to be observed; a fluorescent image of the subject portion to be observed is photographed by the fluorescent-light camera 1412; the fluorescent image processing apparatus 1424 processes the image to make a fluorescent image; and the fluorescent image is displayed on the monitor 1429 so that the fluorescent observation and cure are performed. As described above, the curing laser beam emitted by the curing laser apparatus 1430 is emitted through the leading portion of the laser probe 1432 through the endoscope 1401 to irradiate an aimed portion so that the laser beam irradiation cure is performed while performing the fluorescent diagnosis.

The fluorescent image to be observed is pseudo-color-displayed similarly to the embodiment shown in FIG. 69 such that the normal portion is displayed in green, the diseased portion is displayed in red and a portion treated by the laser beam irradiation and therefore emitting no fluorescent light is displayed in white or black, that is different from the colors of the healthy portion and the diseased portion. While observing the fluorescent image and performing the fluorescent diagnosis, the curing laser beam is emitted.

The fluorescent image of the treatment portion obtained by the fluorescent image processing apparatus 1424 is used to determine the range or the state of the treatment of the diseased portion. Furthermore, a laser beam emission control signal is transmitted in accordance with the state of the fluorescent image to control the emission of the curing laser apparatus 1430.

The fluorescent diagnosis enables the range of the diseased portion to be confirmed and the range is cured by the irradiation with the laser beams. At this time, the diseased portion is gradually reduced due to the irradiation with the laser beams such that the red portion is reduced and black and white portion indicating the portions (the coagulated portions and the perspirated portions) that are irradiated with the laser beams are enlarged in the fluorescent image displayed on the monitor 1429. When all diseased portions have been irradiated with the laser beams, the red portions indicating the diseased portion disappear. In this embodiment, if a red portion (that is, a diseased portion) is present in the fluorescent image, the fluorescent image processing apparatus 1424 transmits the signal for controlling the emission of the laser beams to the curing laser apparatus 1430 in accordance with the fact that a signal indicating a diseased portion is present. The curing laser apparatus 1430 emits the curing laser beam. When the red portions have disappeared in the fluorescent image and the signal for controlling the emission of the laser beams has been turned off due to the disappear of the signal indicating the diseased portion, the curing laser apparatus 1430 inhibits the emission of the curing laser beams.

As described above, the emission of the curing laser beam is controlled in accordance with the state of the fluorescent image. Therefore, the irradiation with laser beams can automatically be performed while discriminating the diseased portion in accordance with the displayed fluorescent image. As a result, the required and minimum irradiation with laser beams can be performed to cure the diseased portion with the laser beam. Consequently, a safe and efficient cure by the irradiation with laser beams can be performed.

The other operations and effects are the same as those obtainable from those of the example shown in FIG. 69.

Figure 71:
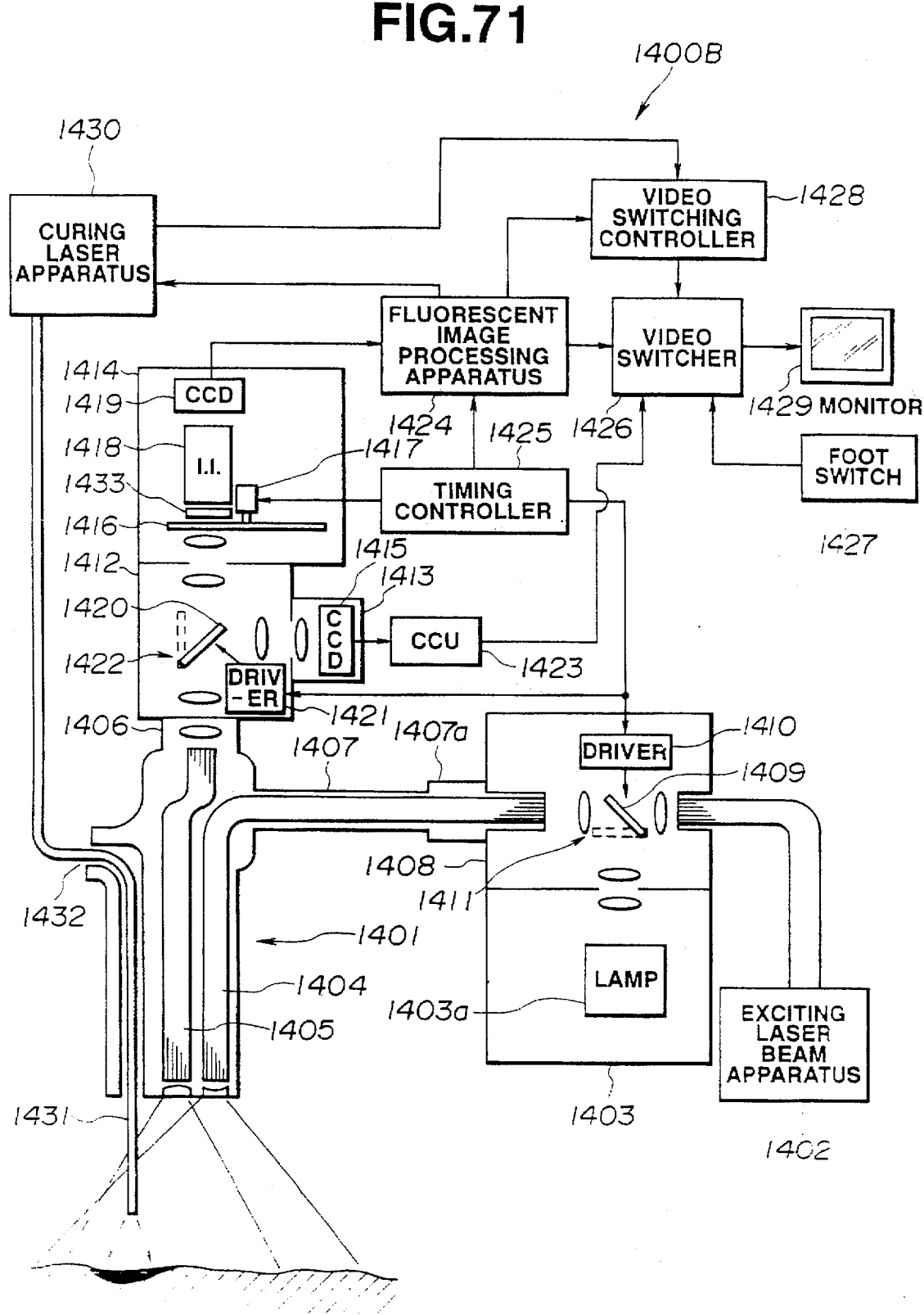
FIG. 71 illustrates another structure of the fluorescent diagnosing and curing endoscope apparatus.

FIG. 71 illustrates the structure of another example of a fluorescent diagnosing and curing apparatus that is capable of simultaneously performing the fluorescent observation and the laser curing operation. In addition to the structure of the example shown in FIG. 70, a function for controlling switching between a fluorescent image and a normal image in accordance with the state of emission of the curing fluorescent light is provided.

That is, a fluorescent diagnosing and curing apparatus 1400B according to this example has an arrangement that the curing laser apparatus 1430 for emitting the curing laser beam is also connected to the video switching controller 1428 so that a laser beam emission signal is transmitted from the curing laser apparatus 1430 to the video switching controller 1428. The other structures are the same as those of the example shown in FIG. 69 and their descriptions are omitted.

When the laser beam irradiation cure is performed by emitting the curing laser beam by the curing laser apparatus 1430 while performing the fluorescent observation and diagnosis, this example has an arrangement in which the laser beam emission signal is transmitted by the curing laser apparatus 1430 to the video switching controller 1428 when the laser beams are emitted so that switching of the image to be observed, which is displayed on the monitor 1429, is controlled. When the video switching controller 1428 has received the laser beam emission signal, it controls switching of the video switcher 1426 to fix the image signal to be transmitted to the monitor 1429 to a normal image which is a visible image. Thus, a normal image is displayed on the monitor 1429 and the fluorescent image is turned off. That is, the portion to be cured is observed on the normal image during the period in which laser beam irradiation cure is being performed.

At this time, the state of treatment (the change in the range of the diseased portion) is recognized in accordance with the fluorescent image obtained by the fluorescent image processing apparatus 1424 similarly to the example shown in FIG. 70. When the signal representing the diseased portion has disappeared, the signal for controlling the emission of the laser beam to be transmitted to the curing laser apparatus 1430 is turned off so that the emission of the curing laser beam is inhibited.

As described above, switching between the fluorescent image and the normal image is controlled in accordance with the state of the emission of the curing laser beam. Thus, the normal image, which is a visible image when the curing laser beam is emitted, is displayed on the monitor to enable the portion to be cured to be observed simultaneously with the naked-eye observation. In addition, a risk of the introduction of the curing laser beam into the observed image can be eliminated. Therefore, the operator is able to safely and reliably perform the laser beam irradiation cure.

Note that the foregoing embodiments may be combined, for example, partially to constitute a different structure.

Although the invention has been described in its preferred form with a certain degree of particularity, it is understood that the present disclosure of the preferred form can be changed in the details of construction and the combination and arrangement of parts may be resorted to without departing from the spirit and the scope of the invention as hereinafter claimed.

What is claimed is:

1. A fluorescent endoscope apparatus, comprising:
   an endoscope including a light guide for transmitting light with which a subject portion to be observed is irradiated and an image guide for transmitting an image obtainable from the subject portion to be observed that has been irradiated with light transmitted through said guide;
   a normal observation light source apparatus for emitting normal light for performing normal light endoscope observation;
   at least one fluorescent observation light source apparatus for emitting excitation light for performing fluorescent light observation;
   an introduced-light switching apparatus for selectively introducing, to said light guide of said endoscope, normal light emitted by said normal observation light source apparatus or excitation light emitted by said fluorescent observation light source apparatus, said introduced-light switching apparatus having a housing provided with an endoscope connection portion to which said light guide of said endoscope is connected, a normal light receiving portion for receiving said normal light emitted by said normal observation light source apparatus, and an excitation light receiving portion for receiving said excitation light emitted by said fluorescent observation light source apparatus;
   an externally-attached-type camera including a rotative filter that selectively transmits a normal light image obtained due to irradiation of the subject portion to be observed with normal light or excitation light and transmitted through said image guide of said endoscope or a fluorescent image obtained due to irradiation with excitation light to form on one solid-state image sensing device, said externally-attached-type camera being attached to an ocular portion of said endoscope;
   a timing controller for synchronizing said image selectively sensed by said externally-attached type camera with light which is introduced from said introduced-light switching apparatus to said light guide of said endoscope;
   an image processing apparatus for converting said image synchronized by said timing controller and formed on said image sensing device of said externally-attached-type camera into video data for the normal observation and converting said fluorescent image formed on said image sensing device and obtained due to the irradiation with excitation light into video data with which fluorescent diagnosis can be performed to determine whether or not the subject portion to be observed is normal,
   wherein said image processing apparatus comprises sensitivity improving means for improving sensitivity of the fluorescent image obtained due to the irradiation with excitation light,
   wherein said sensitivity improving means comprises a two-dimensional lock-in amplifier for calculating a difference and for integrating the fluorescent image obtained due to the irradiation with excitation light,
   wherein said two-dimensional lock-in amplifier comprises:
   an A/D converter for converting an image signal into digital data;
   a multiplexor for distributing image data converted by said A/D converter;
   two frame memories for storing data distributed by said multiplexor;
   a difference-calculating circuit for canceling a noise component by calculating difference of data in said two frame memories; and an integrating circuit for accumulating image data from which the noise component has been canceled by said difference-calculating circuit, wherein the number of integration operations performed by said integrating circuit is changed in accordance with the brightness of the fluorescent image transmitted through said image guide of said endoscope and obtained due to the irradiation with excitation light so that S/N ratio is improved; and display switch means for switching display between a mode in which normal observation video data and fluorescent observation video data processed by said image processing apparatus are simultaneously displayed and a mode in which they are displayed in a time-divided manner.

2. A fluorescent endoscope apparatus comprising:

an endoscope including a light guide for transmitting light with which a subject portion to be observed is irradiated and an image guide for transmitting an image obtainable from the subject portion to be observed that has been irradiated with light transmitted through said guide;

a normal observation light source apparatus for emitting normal light for performing normal light endoscope observation;

at least one fluorescent observation light source apparatus for emitting excitation light for performing fluorescent light observation;

an introduced-light switching apparatus for selectively introducing, to said light guide of said endoscope, normal light emitted by said normal observation light source apparatus or excitation light emitted by said fluorescent observation light source apparatus, said introduced-light switching apparatus having a housing provided with an endoscope connection portion to which said light guide of said endoscope is connected, a normal light receiving portion for receiving said normal light emitted by said normal observation light source apparatus, and an excitation light receiving portion for receiving said excitation light emitted by said fluorescent observation light source apparatus;

an externally-attached-type camera including a rotative filter that selectively transmits a normal light image obtained due to irradiation of the subject portion to be observed with normal light or excitation light and transmitted through said image guide of said endoscope or a fluorescent image obtained due to irradiation with excitation light to form on one solid-state image sensing device, said externally-attached-type camera being attached to an ocular portion of said endoscope, wherein said externally-attached-type camera includes a driver for operating said image sensing device at high speed;

a timing controller for synchronizing said image selectively sensed by said externally-attached type camera with light which is introduced from said introduced-light switching apparatus to said light guide of said endoscope;

an image processing apparatus for converting said image synchronized by said timing controller and formed on said image sensing device of said externally-attached-type camera into video data for the normal observation and converting said fluorescent image formed on said image sensing device and obtained due to the irradiation with excitation light into video data with which fluorescent diagnosis can be performed to determine whether or not the subject portion to be observed is normal;

display switch means for switching display between a mode in which normal observation video data and fluorescent observation video data processed by said image processing apparatus are simultaneously displayed and a mode in which they are displayed in a time-divided manner; and an integration circuit wherein a number of integration operations of the fluorescent image and the normal image performed by said integration circuit is changed in accordance with a brightness level of the fluorescent image and that of the normal image so that S/N ratio is improved.

3. A fluorescent endoscope apparatus, comprising:

an endoscope including a light guide for transmitting light with which a subject portion to be observed is irradiated and an image guide for transmitting an image obtainable from the subject portion to be observed that has been irradiated with light transmitted through said guide;

a normal observation light source apparatus for emitting normal light for performing normal light endoscope observation;

at least one fluorescent observation light source apparatus for emitting excitation light for performing fluorescent light observation;

an introduced-light switching apparatus for selectively introducing, to said light guide of said endoscope, normal light emitted by said normal observation light source apparatus or excitation light emitted by said fluorescent observation light source apparatus, said introduced-light switching apparatus having housing provided with an endoscope connection portion to which said light guide of said endoscope is connected, a normal light receiving portion for receiving said normal light emitted by said normal observation light source apparatus, and an excitation light receiving portion for receiving said excitation light emitted by said fluorescent observation light source apparatus;

an externally-attached-type camera including a rotative filter that selectively transmits a normal light image obtained due to irradiation of the subject portion to be observed with normal light or excitation light and transmitted through said image guide of said endoscope or a fluorescent image obtained due to irradiation with excitation light to form on one solid-state image sensing device, said externally-attached-type camera being attached to an ocular portion of said endoscope;

a timing controller for synchronizing said image selectively sensed by said externally-attached type camera with light which is introduced from said introduced-light switching apparatus to said light guide of said endoscope;

an image processing apparatus for converting said image synchronized by said timing controller and formed on said image sensing device of said externally-attached-type camera into video data for the normal observation and converting said fluorescent image formed on said image sensing device and obtained due to the irradiation with excitation light into video data with which fluorescent diagnosis can be performed to determine whether or not the subject portion to be observed is normal; and display switch means for switching display between a mode in which normal observation video data and fluorescent observation video data processed by said image processing apparatus are simultaneously displayed and a mode in which they are displayed in a time-divided manner, wherein wavelength characteristics of optical fibers comprising said image guide of said endoscope are such that red color region optical fibers are increased in a peripheral portion as compared with those in a central portion.

4. A fluorescent endoscope apparatus according to claim 3, wherein said optical fibers composing said image guide of said endoscope and disposed in the central portion and those in the peripheral portion have different outer diameters such that said optical fibers disposed in the central portion each have a smaller diameter than that of each of said optical fibers disposed in the peripheral portion.

5. A fluorescent endoscope apparatus according to claim 4, wherein said optical fibers disposed in the central portion have a diameter less than 8 µm and those disposed in the peripheral portion have a diameter of 8 µm or larger.

6. A fluorescent endoscope apparatus according to claim 3, wherein an optical axis changing device is disposed in front of a leading surface of said image guide.

* * * * *